US008420890B2

(12) United States Patent
Gan et al.

(10) Patent No.: US 8,420,890 B2
(45) Date of Patent: Apr. 16, 2013

(54) USE OF NAP GENE TO MANIPULATE LEAF SENESCENCE IN PLANTS

(75) Inventors: Susheng Gan, Ithaca, NY (US); Yongfeng Guo, Ann Arbor, MI (US)

(73) Assignee: Cornell Research Foundation, Inc., Ithaca, NY (US)

( * ) Notice: Subject to any disclaimer, the term of this patent is extended or adjusted under 35 U.S.C. 154(b) by 392 days.

(21) Appl. No.: 12/294,593

(22) PCT Filed: Mar. 28, 2007

(86) PCT No.: PCT/US2007/065321
§ 371 (c)(1),
(2), (4) Date: Nov. 6, 2008

(87) PCT Pub. No.: WO2007/112430
PCT Pub. Date: Oct. 4, 2007

(65) Prior Publication Data
US 2009/0288218 A1 Nov. 19, 2009

Related U.S. Application Data

(60) Provisional application No. 60/786,602, filed on Mar. 28, 2006.

(51) Int. Cl.
C12N 15/82 (2006.01)
C12N 5/10 (2006.01)
C12N 15/113 (2010.01)
A01H 5/10 (2006.01)
A01H 5/00 (2006.01)

(52) U.S. Cl.
USPC ........... 800/285; 800/286; 800/305; 800/306; 800/294; 800/323.1; 800/290

(58) Field of Classification Search .................... 800/276
See application file for complete search history.

(56) References Cited

U.S. PATENT DOCUMENTS

| | | | |
|---|---|---|---|
| 5,177,307 | A | 1/1993 | Houck et al. |
| 6,531,647 | B1 | 3/2003 | Baulcombe et al. |
| 6,693,185 | B2 | 2/2004 | Babiychuk et al. |
| 6,787,684 | B2 | 9/2004 | Descenzo et al. |
| 6,844,486 | B1 | 1/2005 | Xie et al. |
| 7,109,033 | B2 | 9/2006 | Harper et al. |
| 7,141,721 | B2 | 11/2006 | Li et al. |
| 7,164,058 | B2 | 1/2007 | Hanson et al. |
| 7,169,966 | B2 | 1/2007 | Klessig et al. |
| 7,345,217 | B2 | 3/2008 | Zhang et al. |
| 7,820,882 | B2 | 10/2010 | Dubcovsky et al. |
| 2002/0169297 | A1 | 11/2002 | Gan et al. |
| 2003/0172404 | A1 | 9/2003 | John et al. |
| 2003/0224939 | A1 | 12/2003 | Miles |
| 2003/0226173 | A1* | 12/2003 | Ratcliffe et al. ............ 800/281 |
| 2003/0229920 | A1 | 12/2003 | Baulcombe et al. |
| 2003/0233670 | A1 | 12/2003 | Edgerton et al. |
| 2004/0006787 | A1 | 1/2004 | Martin et al. |
| 2004/0016025 | A1 | 1/2004 | Budworth et al. |
| 2004/0093635 | A1 | 5/2004 | Van Enckevort et al. |
| 2004/0128704 | A1 | 7/2004 | Babiychuk et al. |
| 2004/0138176 | A1 | 7/2004 | Miles |
| 2005/0005333 | A1 | 1/2005 | Ruezinsky et al. |
| 2005/0044585 | A1 | 2/2005 | Good et al. |
| 2005/0050584 | A1 | 3/2005 | Gallie et al. |
| 2005/0054837 | A1 | 3/2005 | Brenneman et al. |
| 2005/0144669 | A1 | 6/2005 | Reinhart et al. |
| 2005/0160493 | A9 | 7/2005 | Ratcliffe et al. |
| 2005/0257293 | A1 | 11/2005 | Mascia |
| 2006/0041961 | A1 | 2/2006 | Abad et al. |
| 2006/0162006 | A9 | 7/2006 | Sherman et al. |
| 2006/0183137 | A1 | 8/2006 | Harper et al. |
| 2006/0253926 | A1 | 11/2006 | Harvell et al. |
| 2007/0039066 | A1 | 2/2007 | Mascia |

FOREIGN PATENT DOCUMENTS

| | | |
|---|---|---|
| EP | 1033405 A2 | 9/2000 |
| EP | 1033405 A3 | 9/2000 |
| EP | 1059354 A2 | 12/2000 |
| EP | 1586645 A2 | 10/2005 |
| EP | 1586645 A3 | 10/2005 |
| EP | 1586652 A1 | 10/2005 |
| WO | WO 91/01323 A1 | 2/1991 |
| WO | WO 99/15668 A2 | 4/1999 |
| WO | WO 99/58659 A2 | 11/1999 |
| WO | WO 00/52168 A1 | 9/2000 |
| WO | WO 00/52169 A1 | 9/2000 |
| WO | WO 00/52171 A1 | 9/2000 |
| WO | WO 00/52172 A1 | 9/2000 |
| WO | WO 00/61771 A2 | 10/2000 |
| WO | WO 01/18061 A2 | 3/2001 |
| WO | WO 01/26459 A2 | 4/2001 |
| WO | WO 01/30990 A2 | 5/2001 |

(Continued)

OTHER PUBLICATIONS

Lehner et al. How to use RNA interference (2004) Brief. in Func. Genomics 3: 68-83.*

(Continued)

Primary Examiner — David T Fox
Assistant Examiner — Steven Bernacki
(74) Attorney, Agent, or Firm — LeClairRyan, a Professional Corporation

(57) ABSTRACT

The present invention discloses transgenic plants having an altered level of NAP protein compared to that of a non-transgenic plant, where the transgenic plants display an altered leaf senescence phenotype relative to a non-transgenic plant, as well as mutant plants comprising an inactivated NAP gene, where mutant plants display a delayed leaf senescence phenotype compared to that of a non-mutant plant. The present invention also discloses methods for delaying leaf senescence in a plant, as well as methods of making a mutant plant having a decreased level of NAP protein compared to that of a non-mutant plant, where the mutant plant displays a delayed leaf senescence phenotype relative to a non-mutant plant. Methods for causing precocious leaf senescence or promoting leaf senescence in a plant are also disclosed. Also disclosed are methods of identifying a candidate plant suitable for breeding that displays a delayed leaf senescence and/or enhanced yield phenotype.

29 Claims, 14 Drawing Sheets

FOREIGN PATENT DOCUMENTS

| | | |
|---|---|---|
| WO | WO 02/22675 A2 | 3/2002 |
| WO | WO 02/077185 A2 | 10/2002 |
| WO | WO 03/000898 A1 | 1/2003 |
| WO | WO 03/014327 A2 | 2/2003 |
| WO | WO 2004/027038 A2 | 4/2004 |
| WO | WO 2004/031349 A2 | 4/2004 |
| WO | WO 2005/001050 A2 | 1/2005 |
| WO | WO 2006/005023 A2 | 1/2006 |
| WO | WO 2006/046861 A2 | 5/2006 |
| WO | WO 2006/124752 A2 | 11/2006 |
| WO | WO 2006/130156 A2 | 12/2006 |
| WO | WO 2006/133461 A1 | 12/2006 |

OTHER PUBLICATIONS

Miao et al. Targets of the WRKY53 transcription factor and its role durring leaf senescence in *Arabidopsis* (2004) Plant Mol. Biol. 55: 853-867.*

Ooka et al. Comprehensice analysis of NAC family genes in *Oryza sativa* and *Arabidopsis thaliana* (2003) DNA Research. 10:239-247.*

Breeze et al. Gene expression patterns to define stages of post-harvest senescence in Alstroemeria petals (2004) Plant Biotechnol. J. 2: 155-168.*

Schupp et al. Effect of Aminoethoxyvinylglycine (AVG) on preharvest drop, fruit quality, and maturation of 'McIntosh' apples. I. concentration and timing of dilute applications of AVG (2004) HortScience 395: 1030-1035.*

Delessert et al., "The Transcription Factor ATAF2 Represses the Expression of Pathogenesis-Related Genes in *Arabidopsis*," *Plant J.* 43(5):745-57 (2005).

Fujita et al., "A Dehydration-Induced NAC Protein, RD26, is Involved in a Novel ABA-Dependent Stress-Signaling Pathway," *Plant J.* 39(6):863-76 (2004).

Gregersen & Holm, "Transcriptome Analysis of Senescence in the Flag Leaf of Wheat (*Triticum aestivum* L.)," *Plant Biotechnol. J.* 5(1):192-206 (2007).

Guo & Gan, "AtNAP, a NAC Family Transcription Factor, Has an Important Role in Leaf Senescence," *Plant Journal* 46(4):601-12 (2006).

Guo & Gan, "Transcriptional Regulation of Plant Senescence," *Dissertation Abstracts Int'l.* 66(10B):5266 (2006).

Kandasamy et al., "Silencing the Nuclear Actin-Related Protein AtARP4 in *Arabidopsis* Has Multiple Effects on Plant Development, Including Early Flowering and Delayed Floral Senescence," *Plant J.* 41(6):845-58 (2005).

Lin & Wu, "Molecular Events in Senescing *Arabidopsis* Leaves," *Plant J.* 39(4):612-28 (2004).

Rezende et al., "Litter Deposition and Disappearance in *Brachiaria* Pastures in the Atlantic Forest Region of the South of Bahia, Brazil," *Nutrient Cycling in Agroecosystems* 54(2):99-112 (1999).

Steinberg et al., "Wheat Response to Differences in Water and Nutritional Status Between Zeoponic and Hydroponic Growth Systems," *Agronomy J.* 92(2):353-60 (2000).

Uauy et al., "A NAC Gene Regulating Senescence Improves Grain Protein, Zinc, and Iron Content in Wheat," *Science* 314(5803):1298-1301 (2006).

Wabiko & Yasuda, "Isolation of the Leaf Senescence-Associated NAC-Family Gene From Rice," Poster Presentation at the Annual Meeting of the American Society of Plant Biologists on Plant Biology (Aug. 4, 2002) (Abstract), available at http://abstracts.aspb.org/pb2002/public/P46/0227.html (last visited Feb. 23, 2009).

Wang et al., "Transcriptomic Adaptations in Rice Suspension Cells Under Sucrose Starvation," *Plant Mol. Biol.* 63(4):441-63(2007).

Way et al., "The Aster Leafhopper (Homoptera: Cicadellidae) in California Rice: Herbicide Treatment Affects Population Density and Induced Infestations Reduce Grain Yield," *J. Econ. Entomol.* 77(4):936-42 (1984).

Xie et al., "GRAB Proteins, Novel Members of the NAC Domain Family, Isolated by Their Interaction with a Geminivirus Protein," *Plant Mol. Biol.* 39(4):647-56 (1999).

Yunovitz et al., "Unconjugated $Man_5GlcNAc$ Occurs in Vegetative Tissues of Tomato," *Phytochemistry* 42(3):607-10 (1996).

Sablowski et al. 'A Homolog of NO APICAL MERISTEM is an Immediate Target of the Floral Homeotic Genes APETALA3/PISTILLATA', Cell 92:93-103 (1998).

Guo et al. 'Transcriptome of *Arabidopsis* Leaf Senescence', Plant, Cell and Environment 27:521-549 (2004).

Ahn et al., "Silencing of NbNAP1 Encoding a Plastidic SufB-like Protein Affects Chloroplast Development in *Nicotiana benthamiana*," Molecules and Cells 20(1):112-8 (2005).

Buchanan-Wollaston et al., "Comparative Transcriptome Analysis Reveals Significant Differences in Gene Expression and Signalling Pathways Between Developmental and Dark/Starvation-Induced Senescence in *Arabidopsis*," The Plant Journal 42:567-85 (2005).

He et al., "AtNAC2, a Transcription Factor Downstream of Ethylene and Auxin Signaling Pathways, is Involved in Salt Stress Response and Lateral Root Development," The Plant Journal 44:903-16 (2005).

Li et al., "*Arabidopsis* NAP and PIR Regulate Actin-Based Cell Morphogenesis and Multiple Developmental Processes," Plant Physiology 136:3616-27 (2004).

Lim et al., "Molecular Genetics of Leaf Senescence in *Arabidopsis*," Trends in Plant Science 8(6):272-8 (2003).

Miao et al., "Targets of the WRKY53 Transcription Factor and Its Role During Leaf Senescence in *Arabidopsis*," Plant Molecular Biology 55:853-67 (2004).

Olsen et al., "NAC Transcription Factors: Structurally distinct, Functionally Diverse," Trends in Plan tScience 10 (2):79-87 (2005).

Supplementary European Search Report for International Patent Application No. EP07759538 (Aug. 17, 2009).

Wabiko et al., "Isolation of the Leaf Senescence-Associated NAC-Family Gene from Rice," The American Society of Plant Biologist, (Printed Aug. 12, 2009) (Abstract).

First Office Action for corresponding Chinese Patent Application No. 200780019749.9 (May 25, 2011).

Second Office Action for corresponding Chinese Patent Application No. 200780019749.9 (Jun. 6, 2012).

Examination Report for corresponding European Patent Application No. 07759538.7 (Jan. 20, 2012).

Wabiko et al. "Isolation of the Leaf Senescence-associated NAC-Family Gene from Rice," American Society of Plant Biologists, Poster: Developmental Patterning, Abstract # 345 (2002).

Alonso et al., "Genome-Wide Insertional Mutagenesis of *Arabidopsis thaliana*," Science 301:653-657 (2003).

Examination Report for corresponding European Patent Application No. 07759538.7 (Aug. 29, 2012).

GenBank Accession No. BH171933.1 (2001).

GenBank Accession No. CC792958.1 (2003).

Examination Report for corresponding European Patent Application No. 07 759 538.7 (Sep. 30, 2010).

Examination Report for corresponding European Patent Application No. 07 759 538.7 (Aug. 11, 2011).

International Search Report for PCT/US2007/065321 (Jun. 3, 2008).

Written Opinion for PCT/US2007/065321 (Jun. 3, 2008).

* cited by examiner

CLUSTAL W (1.82) multiple sequence alignment of NAP proteins

```
Kidney bean    --MDATTPS---------------ELPPGFRFHPTDEELIVYYLCNQATSKPCPASII 41
Medicago       --MESSASS---------------ELPPGFRFHPTDEELIVHYLCNQATSKPCPASII 41
Soybean        --MENRTSS---------------VLPPGFRFHPTDEELIVYYLCNQASSRPCPASII 41
Populus        -----TNSE---------------QLPPGFRFHPTDEELIMYYLRNQATSRPCPASII 38
Nightshade     --MVGKISS---------------DLPPGFRFHPTDEELIMYYLRYQATSRPCPVSII 41
Arabidopsis    --MEVTSQS---------------TLPPGFRFHPTDEELIVYYLRNQTMSKPCPVSII 41
Wheat          MPMGSSAAMP--------------ALPPGFRFHPTDEELIVHYLRRQAASMPSPVPII 44
Rice           --MVLSNPA---------------MLPPGFRFHPTDEELIVHYLRNRAASSPCPVSII 41
Maize          --MVMANPD---------------MLPPGFRFHPTDEELILHYLRNRAANAPCPVAII 41
Peach          --MESTDSSTASQQQQQQQPQPPPQPNLPPGFRFHPTDEELVVHYLKKKVTSAPLPVAII 58
Tomato         --MESTDSSTGTRH----------QPQLPPGFRFHPTDEELIVHYLKKRVAGAPIPVDII 48
Petunia        --MTTAELQ-----------------LPPGFRFHPTDEELVMHYLCRKCASQPIAVPII 40
Potato         --MGVQEKYP-----------LLQLSLPPGFRFYPTDEELLVQYLCKKVAGHDFPLQII 46
                                       ****** ****:** ::  **   :   .   **

Kidney bean    PEVDLYKFDPWELPDKTEFGENEWYFFSPRDRKYPNGVRPNRATVSGYWKATGTDKAIYS 101
Medicago       PEVDIYKFDPWELPDKSEFEENEWYFFSPRERKYPNGVRPNRATLSGYWKATGTDKAIKS 101
Soybean        PEVDIYKFDPWELPDKTDFGEKEWYFFSPRERKYPNGVRPNRATVSGYWKATGTDKAIYS 101
Populus        PEVDIYKFDPWQLPEKADFGENEWYFFTPLDRKYPNGVRPNRATVSGYWKATGTDKAIHS 98
Nightshade     PEIDVYKFDPWELPEKAEFGENEWYFFTPRDRKYPNGVRPNRAAVSGYWKATGTDKAIYS 101
Arabidopsis    PEVDIYKFDPWQLPEKTEFGENEWYFFSPRERKYPNGVRPNRAAVSGYWKATGTDKAIHS 101
Wheat          AEVNIYKCNPWDLPGKALFGENEWYFFSPRDRKYPNGARPNRAAGSGYWKATGTDKAILS 104
Rice           ADVDIYKFDPWDLPSKENYGDREWYFFSPRDRKYPNGIRPNRAAGSGYWKATGTDKPIHS 101
Maize          ADVDIYKFDPWDLP-RAAYGDKEWYFFSPRDRKYPNGIRPNRAAGSGYWKATGTDKPIHS 100
Peach          AEIELYKFDPWELPAKATFGEQEWYFFSPRDRKYPNGARPNRAATSGYWKATGTDKPVLT 118
Tomato         GEIDLYKFDPWELPAKAIFGEQEWFFFSPRDRKYPNGARPNRAATSGYWKATGTDKPVFT 108
Petunia        AEIDLYKYDPWDLPDLALYGEKEWYFFSPRDRKYPNGSRPNRAAGTGYWKATGADKPIGH 100
Potato         GEIDLYKFDPWVLPSKATFGEKEWYFFSPRDRKYPNGSRPNRVAGSGYWKATGTDKIITS 106
               ::::** :** **         : :.**:**:*  :****  ****  :  :********:** :

Kidney bean    -----GSKLVGVKKSLVFYKGRPPKGDKTDWIMHEYRLAESKQPVN---------RKIGS 147
Medicago       -----GSKQIGVKKSLVFYKGRPPKGVKTDWIMHEYRLIGSQKQTS---------KHIGS 147
Soybean        -----GSKHVGVKKALVFYKGKPPKGLKTDWIMHEYRLIGSRRQAN---------RQVGS 147
Populus        -----GSKYVGVKKALVFYKGRPPKGTKTDWIMQEYRLNDSNKPAS---------KQNGS 144
Nightshade     -----ANKYVGIKKLVFYKGKPPKGVKTDWIMHEYRLSDSKSQTYS---------KQSGS 148
Arabidopsis    -----GSSNVGVKKALVFYKGRPPKGIKTDWIMHEYRLHDSRKAST---------KRNGS 147
Wheat          T---PANESIGVKKALVFYRGKPPKGVKTDWIMHEYRLTAADNRTTK--------RRGSS 153
Rice           SGGAATNESVGVKKALVFYKGRPPKGTKTNWIMHEYRLAAADAHAANTYRP--MKFRNTS 159
Maize          S---TTAGESVGVKKALVFYEGRPPKGTKTNWIMHEYRLAA-DAQAAHAYRP--MKFRNAS 155
Peach          SG---GTQKVGVKKALVFYGGKPPKGIKTNWIMHEYRLADSKTSNKPPGCD--LGNKKNS 173
Tomato         SG---GTQKVGVKKALVFYGGKPPKGVKTNWIMHEYRVVENKTNNKPLGCDNIVANKKGS 165
Petunia        ------PKAVGIKKALVFYAGKAPKGEKTNWIMHEYRLADVDRSAR---------KNNNS 145
Potato         -----QGRKVGIKKALVFYVGKAPKGSKTNWIMHEYRLFESSKKNN-----------GS 149
                :*:**:****  *: .***  ** **:*** :***:

Kidney bean    MRLDDWVLCRIYKKK----NTGKT-LEHK----------ETHPKVQMTNLIA-------- 184
Medicago       MRLDDWVLCRIYKKK----HMGKT-LQQK----------EDYSTHQFNDSII-------- 184
Soybean        MRLDDWVLCRIYKKK----NIGKS-MEAK----------EDYPIAQINLTPA-------- 184
Populus        MRL---VLCRIYRKK----HAIRH-LEEK----------TENPVHAHLDVTP-------- 178
Nightshade     MRLDDWVLCRIYKKK----NLGKT-IEMMK--------VEEEELEAQNVSIN-------- 187
Arabidopsis    MRLDEWVLCRIYKKR----GASKL-LNEQEGFMDEVLMEDETKVVVNEAERR-------- 194
Wheat          MRLDDWVLCRIHKKCGNLPNFSSS-DQEQEHEQESSTVEDSQNNHTVSSPKSEAFDG--- 209
Rice           MRLDDWVLCRIYKKSSHASPLAVPPLSDHEQDEPCALEENAPLYAPSSSSAASMILQGAA 219
Maize          MRVRRTLL---------------------------------------------------- 163
Peach          LRLDDWVLCRIYKKNNSHRPMDLEREDSMEDMMGPLMPPSISHVGHHQNMNLHLPKSNTN 233
Tomato         LRLDDWVLCRIYKKNNTQR-----SIDDLHDMLG-----SIPQN--VPNSILQGIKP-SN 212
```

Figure 1

```
Petunia      LRLDDWVLCRIYNKKG---SIEKNQLNNKK--------IMNTSYMDMTVSSEE-------- 187
Potato       SKLDEWVLCRIYKKNSSGPKPLMSGLHSSNEYSHGSSTSSSSQFDDMLESLP-------- 201

Kidney bean  ------ANND--EQKMMNLPRTWSLTYLLDMNYLGP-----------ILSDGS-------- 218
Medicago     ------TNNDDGELEMMNLTRSCSLTYLLDMNYFGP-----------ILSDG--------- 219
Soybean      ------NNNS--EQELVKFPRTSSLTHLLEMDYLGPI--------SHILPDAS-------- 221
Populus      ------DNDAR-EQQMMKISGTCSLSRLLEMEYLGSI--------SQLLSGDT-------- 216
Nightshade   ------NAIEVGGPQTMKLPRICSLSHLLELDYFGSI--------PQLLSDNL-------- 226
Arabidopsis  ------TEEEIMMMTSMKLPRTCSLAHLLEMDYMGP-----------VSHID-------- 229
Wheat        ---DGDDHLQLQQFRPMAIAKSCSLTDLLNTVDYAAL--------SHLLLDGAGASSSDA 258
Rice         AGAFPSLHAAAAATQRTAMQKIPSISDLLNEYSLSQLFDDGGAAAAAPLQEMARQPDHHH 279
Maize        ------------------------------------------------------------
Peach        YGPPFIENDQIIFDGIMSSTDGSASLSN-GTSQLPLK----RSIVPSLYRNDQEDDQTAG 288
Tomato       YGTILLENESNMYDGIMNNTNDIINNNNRSIPQISSK----RTMHGGLYWNNDEATTTTT 268
Petunia      ------DRKPEILPPLPPQPAPQQQQVYNDFFYLDPS------DSVPKIHSDSSCS----- 231
Potato       ----EMDDRFSNLPRLNSLKTEKLNLERLDSANFDWAILAGLKPMPELRPANQAPG---- 253

Kidney bean  ---------------------------YCSTFDFQISNA-NIGIDPFVNSQPVEMANNYVSDS 253
Medicago     ---------------------------STLDFQINNS-NIGIDPYVKPQPVEMTNHYEADS 252
Soybean      ---------------------------YNSTFDFQINTA-NGGIDPFVKPQLVEIP--YATDS 254
Populus      ---------------------------YNSDFDSQ-------------------------- 224
Nightshade   ---------------------------LYDDQSYTMNNVSNTSNVDQVSSQQQNTNNITSNNC 262
Arabidopsis  ---------------------------NFSQFDHLHQPDSESSWFGDLQFNQDEILNHHRQAM 265
Wheat        GADYQLPPE------NPLIYSQPFWQQTLHYNNNNGYVNNETIDVPQLPEARVDDYGMNG 312
Rice         HQQQQHALFGHPVMNHFIANNSMVQLAHLDPSSSAAASTSAGAVVEPPAVTGKRKRSSDG 339
Maize        ------------------------------------------------------------
Peach        ------ASSSK---------RVVQLHQLDSGTNNS----VAANNNSTSIANLLSQLPQT 328
Tomato       TIDRNHSPNTK----------RFLVENNEDDGLNMNNISRITNHEQSSSIANFLSQFPQN 318
Petunia      ---------------------EHVVSPEFTCEREVQSEAKLSEWEKAALDLPFNYMDATT 270
Potato       -------------------VQGQGQAQGNVNNHNNNNMNFLNDVYAHPTTNFRGNTKVE 293

Kidney bean  GKY--------------------------------------------------------- 256
Medicago     HSSIT------NQP------IFVKQMHNYLA----------------------------- 271
Soybean      GKYQV------KQNSTINPTIFVNQVYDQRG----------------------------- 279
Populus      ------------------------------------------------------------
Nightshade   NIFFN------YQQP------LFVNPTFQSQ----------------------------- 281
Arabidopsis  FKF--------------------------------------------------------- 268
Wheat        DKYNG------MKRKRSSGSLYCSQLQLPADQYSGMLIHPFLSQQLHM------------ 354
Rice         GEPTIQALPPAAAAAKKPNGSCVGATFQIGSALQGSSLGLSHQMLLHSNMGMN--- 392
Maize        ------------------------------------------------------------
Peach        PPLHQH-----AMLGSLGDG-LFRTPY-QLFGMNWFSESNLG------------------ 363
Tomato       PSIQQQQQQEEVLGSLNDGVVFRQPYNQVTGMNWYS----------------------- 355
Petunia      GATTLDNSLLGSQFQSSYQMSPLQDMFMHLHKPF------------------------- 304
Potato       SINLDEEVESGNRNRRIDQSSYFQQSLNGFSQAYTNSVDQFGIQCPNQTLNLGFRQ 349
```

Figure 1 (cont'd)

(a)
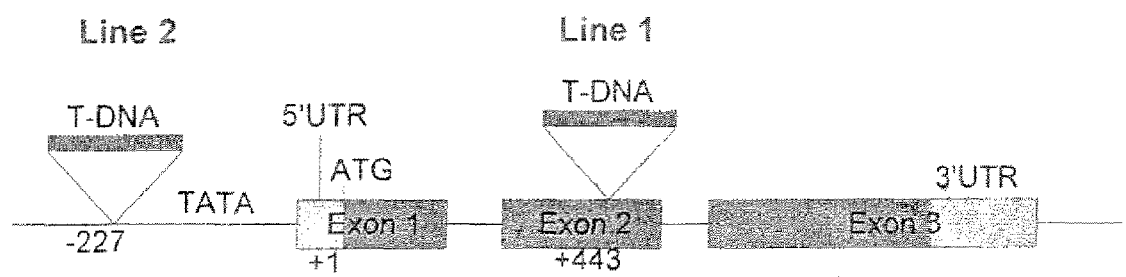
(b)
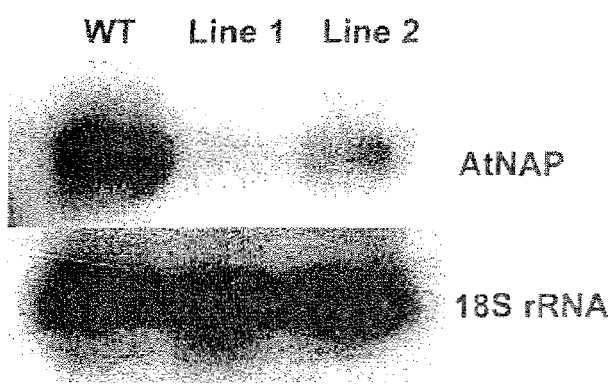
Figure 4

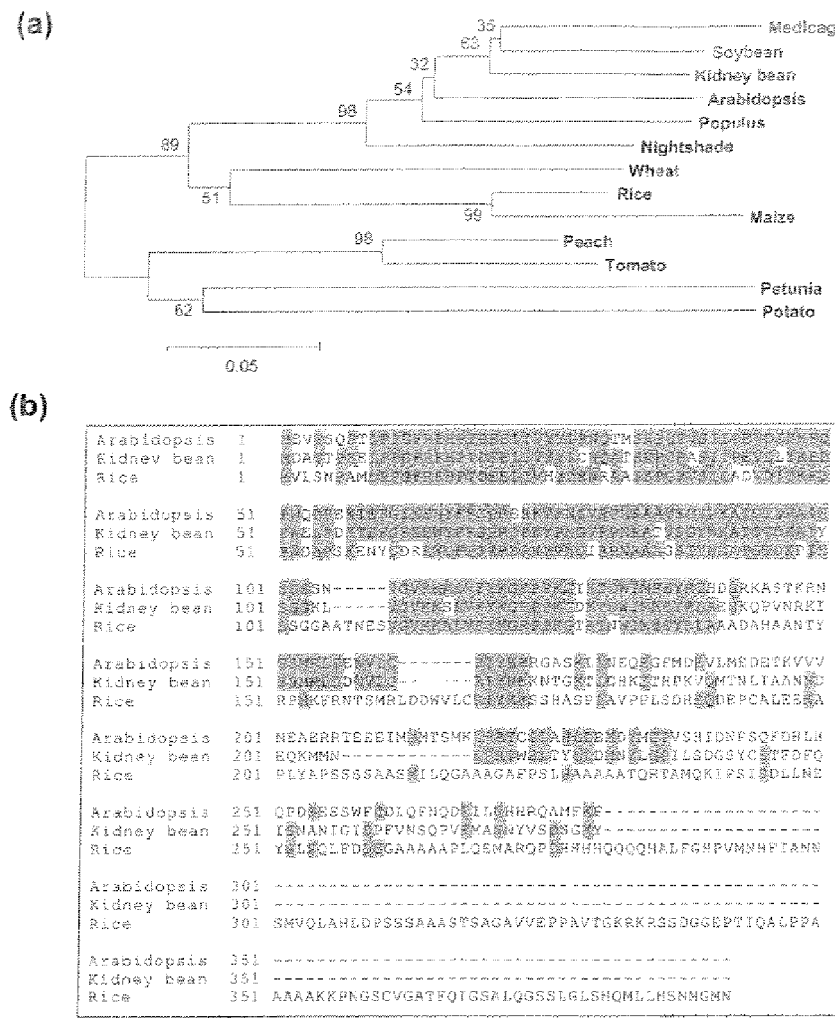
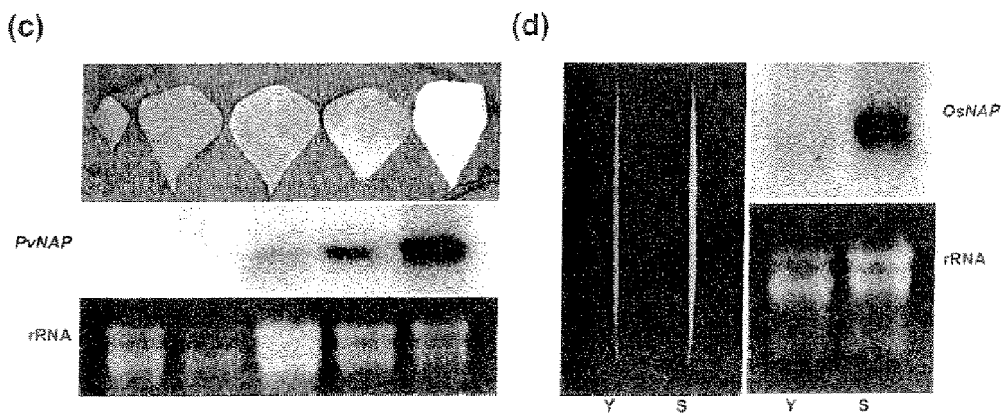
Figure 9

(a)
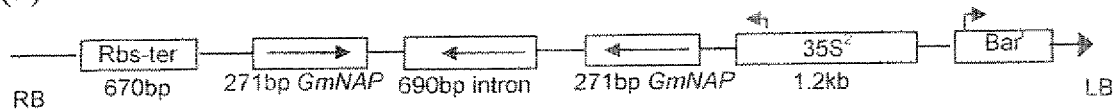
(b)
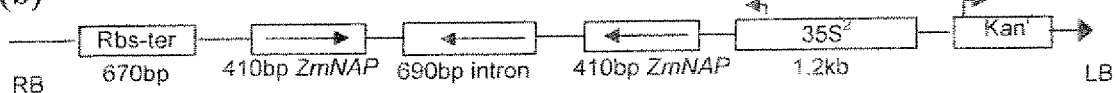
Figure 11

(a)
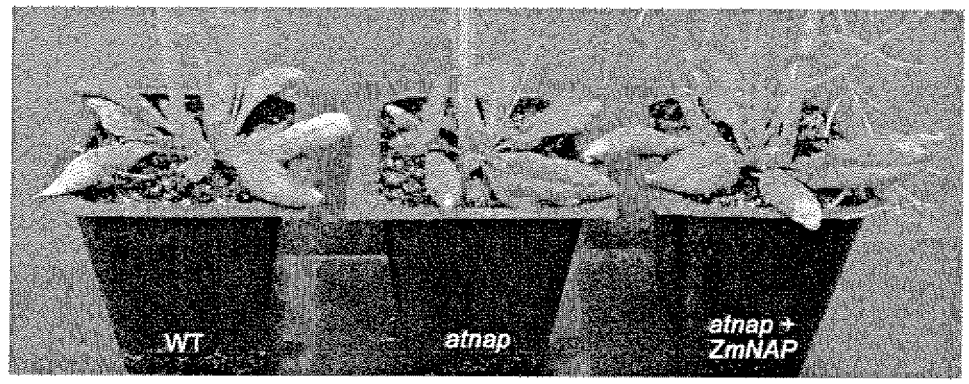
(b)
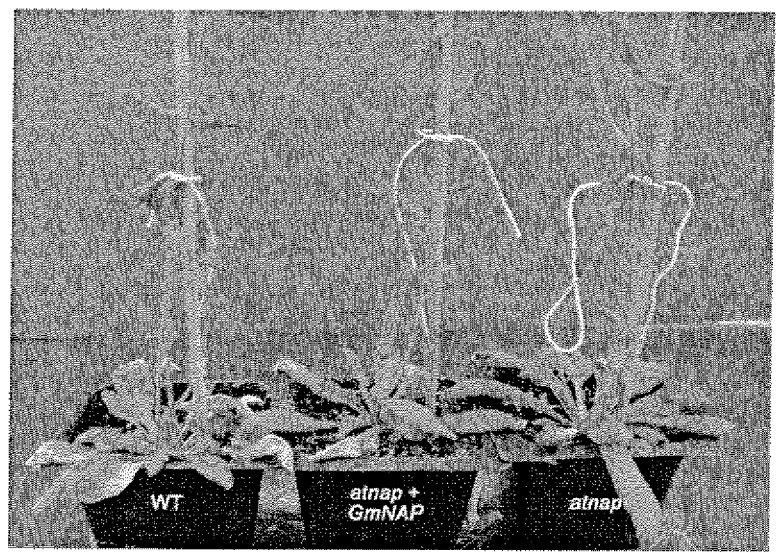
Figure 12

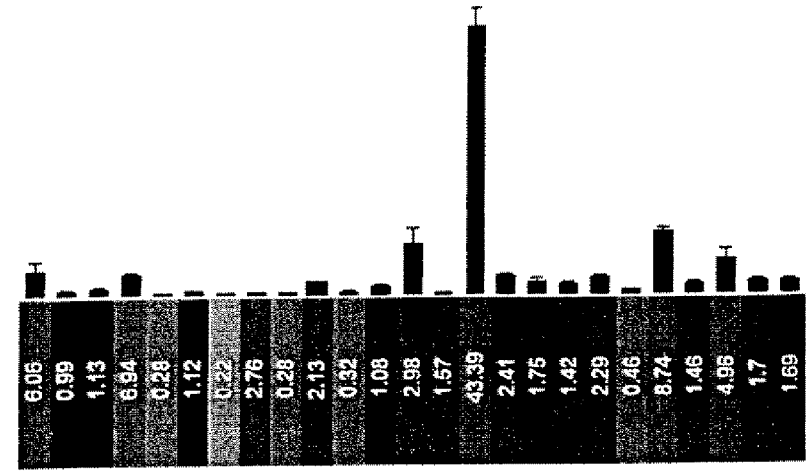
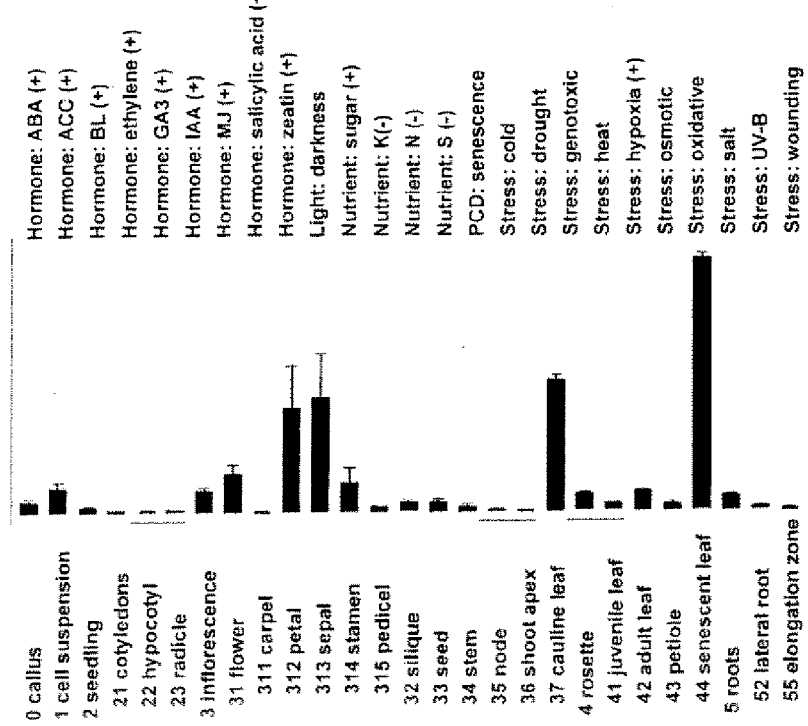
Figure 13

SEQUENCE LISTING

```
<160> NUMBER OF SEQ ID NOS: 45

<210> SEQ ID NO 1
<211> LENGTH: 256
<212> TYPE: PRT
<213> ORGANISM: Phaseolus vulgaris

<400> SEQUENCE: 1

Met Asp Ala Thr Thr Pro Ser Glu Leu Pro Pro Gly Phe Arg Phe His
1               5                   10                  15

Pro Thr Asp Glu Glu Leu Ile Val Tyr Tyr Leu Cys Asn Gln Ala Thr
            20                  25                  30

Ser Lys Pro Cys Pro Ala Ser Ile Ile Pro Glu Val Asp Leu Tyr Lys
        35                  40                  45

Phe Asp Pro Trp Glu Leu Pro Asp Lys Thr Glu Phe Gly Glu Asn Glu
    50                  55                  60

Trp Tyr Phe Phe Ser Pro Arg Asp Arg Lys Tyr Pro Asn Gly Val Arg
65                  70                  75                  80

Pro Asn Arg Ala Thr Val Ser Gly Tyr Trp Lys Ala Thr Gly Thr Asp
                85                  90                  95

Lys Ala Ile Tyr Ser Gly Ser Lys Leu Val Gly Val Lys Lys Ser Leu
            100                 105                 110

Val Phe Tyr Lys Gly Arg Pro Pro Lys Gly Asp Lys Thr Asp Trp Ile
        115                 120                 125

Met His Glu Tyr Arg Leu Ala Glu Ser Lys Gln Pro Val Asn Arg Lys
    130                 135                 140

Ile Gly Ser Met Arg Leu Asp Asp Trp Val Leu Cys Arg Ile Tyr Lys
145                 150                 155                 160

Lys Lys Asn Thr Gly Lys Thr Leu Glu His Lys Glu Thr His Pro Lys
                165                 170                 175

Val Gln Met Thr Asn Leu Ile Ala Ala Asn Asn Asp Glu Gln Lys Met
            180                 185                 190

Met Asn Leu Pro Arg Thr Trp Ser Leu Thr Tyr Leu Leu Asp Met Asn
        195                 200                 205

Tyr Leu Gly Pro Ile Leu Ser Asp Gly Ser Tyr Cys Ser Thr Phe Asp
    210                 215                 220

Phe Gln Ile Ser Asn Ala Asn Ile Gly Ile Asp Pro Phe Val Asn Ser
225                 230                 235                 240

Gln Pro Val Glu Met Ala Asn Asn Tyr Val Ser Asp Ser Gly Lys Tyr
                245                 250                 255

<210> SEQ ID NO 2
<211> LENGTH: 271
<212> TYPE: PRT
<213> ORGANISM: Medicago truncatula

<400> SEQUENCE: 2
```

```
Met Glu Ser Ser Ala Ser Ser Glu Leu Pro Pro Gly Phe Arg Phe His
1               5                   10                  15

Pro Thr Asp Glu Glu Leu Ile Val His Tyr Leu Cys Asn Gln Ala Thr
            20                  25                  30

Ser Lys Pro Cys Pro Ala Ser Ile Ile Pro Glu Val Asp Ile Tyr Lys
        35                  40                  45

Phe Asp Pro Trp Glu Leu Pro Asp Lys Ser Glu Phe Glu Glu Asn Glu
50                  55                  60

Trp Tyr Phe Phe Ser Pro Arg Glu Arg Lys Tyr Pro Asn Gly Val Arg
65                  70                  75                  80

Pro Asn Arg Ala Thr Leu Ser Gly Tyr Trp Lys Ala Thr Gly Thr Asp
                85                  90                  95

Lys Ala Ile Lys Ser Gly Ser Lys Gln Ile Gly Val Lys Lys Ser Leu
                100                 105                 110

Val Phe Tyr Lys Gly Arg Pro Pro Lys Gly Val Lys Thr Asp Trp Ile
            115                 120                 125

Met His Glu Tyr Arg Leu Ile Gly Ser Gln Lys Gln Thr Ser Lys His
130                 135                 140

Ile Gly Ser Met Arg Leu Asp Asp Trp Val Leu Cys Arg Ile Tyr Lys
145                 150                 155                 160

Lys Lys His Met Gly Lys Thr Leu Gln Gln Lys Glu Asp Tyr Ser Thr
                165                 170                 175

His Gln Phe Asn Asp Ser Ile Ile Thr Asn Asn Asp Asp Gly Glu Leu
            180                 185                 190

Glu Met Met Asn Leu Thr Arg Ser Cys Ser Leu Thr Tyr Leu Leu Asp
                195                 200                 205

Met Asn Tyr Phe Gly Pro Ile Leu Ser Asp Gly Ser Thr Leu Asp Phe
210                 215                 220

Gln Ile Asn Asn Ser Asn Ile Gly Ile Asp Pro Tyr Val Lys Pro Gln
225                 230                 235                 240

Pro Val Glu Met Thr Asn His Tyr Glu Ala Asp Ser His Ser Ser Ile
                245                 250                 255

Thr Asn Gln Pro Ile Phe Val Lys Gln Met His Asn Tyr Leu Ala
            260                 265                 270

<210> SEQ ID NO 3
<211> LENGTH: 279
<212> TYPE: PRT
<213> ORGANISM: Glycine max

<400> SEQUENCE: 3

Met Glu Asn Arg Thr Ser Ser Val Leu Pro Pro Gly Phe Arg Phe His
1               5                   10                  15

Pro Thr Asp Glu Glu Leu Ile Val Tyr Tyr Leu Cys Asn Gln Ala Ser
            20                  25                  30

Ser Arg Pro Cys Pro Ala Ser Ile Ile Pro Glu Val Asp Ile Tyr Lys
        35                  40                  45

Phe Asp Pro Trp Glu Leu Pro Asp Lys Thr Asp Phe Gly Glu Lys Glu
50                  55                  60

Trp Tyr Phe Phe Ser Pro Arg Glu Arg Lys Tyr Pro Asn Gly Val Arg
65                  70                  75                  80

Pro Asn Arg Ala Thr Val Ser Gly Tyr Trp Lys Ala Thr Gly Thr Asp
                85                  90                  95

Lys Ala Ile Tyr Ser Gly Ser Lys His Val Gly Val Lys Lys Ala Leu
                100                 105                 110
```

```
Val Phe Tyr Lys Gly Lys Pro Pro Lys Gly Leu Lys Thr Asp Trp Ile
    115                 120                 125

Met His Glu Tyr Arg Leu Ile Gly Ser Arg Arg Gln Ala Asn Arg Gln
130                 135                 140

Val Gly Ser Met Arg Leu Asp Asp Trp Val Leu Cys Arg Ile Tyr Lys
145                 150                 155                 160

Lys Lys Asn Ile Gly Lys Ser Met Glu Ala Lys Glu Asp Tyr Pro Ile
                165                 170                 175

Ala Gln Ile Asn Leu Thr Pro Ala Asn Asn Ser Glu Gln Glu Leu
            180                 185                 190

Val Lys Phe Pro Arg Thr Ser Ser Leu Thr His Leu Leu Glu Met Asp
        195                 200                 205

Tyr Leu Gly Pro Ile Ser His Ile Leu Pro Asp Ala Ser Tyr Asn Ser
    210                 215                 220

Thr Phe Asp Phe Gln Ile Asn Thr Ala Asn Gly Gly Ile Asp Pro Phe
225                 230                 235                 240

Val Lys Pro Gln Leu Val Glu Ile Pro Tyr Ala Thr Asp Ser Gly Lys
                245                 250                 255

Tyr Gln Val Lys Gln Asn Ser Thr Ile Asn Pro Thr Ile Phe Val Asn
            260                 265                 270

Gln Val Tyr Asp Gln Arg Gly
        275

<210> SEQ ID NO 4
<211> LENGTH: 224
<212> TYPE: PRT
<213> ORGANISM: Populus trichocarpa

<400> SEQUENCE: 4

Thr Asn Ser Glu Gln Leu Pro Pro Gly Phe Arg Phe His Pro Thr Asp
1               5                   10                  15

Glu Glu Leu Ile Met Tyr Tyr Leu Arg Asn Gln Ala Thr Ser Arg Pro
            20                  25                  30

Cys Pro Ala Ser Ile Ile Pro Glu Val Asp Ile Tyr Lys Phe Asp Pro
        35                  40                  45

Trp Gln Leu Pro Glu Lys Ala Asp Phe Gly Glu Asn Glu Trp Tyr Phe
    50                  55                  60

Phe Thr Pro Leu Asp Arg Lys Tyr Pro Asn Gly Val Arg Pro Asn Arg
65                  70                  75                  80

Ala Thr Val Ser Gly Tyr Trp Lys Ala Thr Gly Thr Asp Lys Ala Ile
                85                  90                  95

His Ser Gly Ser Lys Tyr Val Gly Val Lys Lys Ala Leu Val Phe Tyr
            100                 105                 110

Lys Gly Arg Pro Pro Lys Gly Thr Lys Thr Asp Trp Ile Met Gln Glu
        115                 120                 125

Tyr Arg Leu Asn Asp Ser Asn Lys Pro Ala Ser Lys Gln Asn Gly Ser
    130                 135                 140

Met Arg Leu Val Leu Cys Arg Ile Tyr Arg Lys Arg His Ala Ile Arg
145                 150                 155                 160

His Leu Glu Glu Lys Thr Glu Asn Pro Val His Ala His Leu Asp Val
                165                 170                 175

Thr Pro Asp Asn Asp Ala Arg Glu Gln Gln Met Met Lys Ile Ser Gly
            180                 185                 190

Thr Cys Ser Leu Ser Arg Leu Leu Glu Met Glu Tyr Leu Gly Ser Ile
        195                 200                 205
```

Ser Gln Leu Leu Ser Gly Asp Thr Tyr Asn Ser Asp Phe Asp Ser Gln
        210                 215                 220

<210> SEQ ID NO 5
<211> LENGTH: 281
<212> TYPE: PRT
<213> ORGANISM: Solanum demissum

<400> SEQUENCE: 5

Met Val Gly Lys Ile Ser Ser Asp Leu Pro Gly Phe Arg Phe His
1               5                   10                  15

Pro Thr Asp Glu Glu Leu Ile Met Tyr Tyr Leu Arg Tyr Gln Ala Thr
                20                  25                  30

Ser Arg Pro Cys Pro Val Ser Ile Ile Pro Glu Ile Asp Val Tyr Lys
            35                  40                  45

Phe Asp Pro Trp Glu Leu Pro Glu Lys Ala Glu Phe Gly Glu Asn Glu
        50                  55                  60

Trp Tyr Phe Phe Thr Pro Arg Asp Arg Lys Tyr Pro Asn Gly Val Arg
65                  70                  75                  80

Pro Asn Arg Ala Ala Val Ser Gly Tyr Trp Lys Ala Thr Gly Thr Asp
                85                  90                  95

Lys Ala Ile Tyr Ser Ala Asn Lys Tyr Val Gly Ile Lys Lys Ala Leu
            100                 105                 110

Val Phe Tyr Lys Gly Lys Pro Pro Lys Gly Val Lys Thr Asp Trp Ile
        115                 120                 125

Met His Glu Tyr Arg Leu Ser Asp Ser Lys Ser Gln Thr Tyr Ser Lys
    130                 135                 140

Gln Ser Gly Ser Met Arg Leu Asp Asp Trp Val Leu Cys Arg Ile Tyr
145                 150                 155                 160

Lys Lys Lys Asn Leu Gly Lys Thr Ile Glu Met Met Lys Val Glu Glu
                165                 170                 175

Glu Glu Leu Glu Ala Gln Asn Val Ser Ile Asn Asn Ala Ile Glu Val
            180                 185                 190

Gly Gly Pro Gln Thr Met Lys Leu Pro Arg Ile Cys Ser Leu Ser His
        195                 200                 205

Leu Leu Glu Leu Asp Tyr Phe Gly Ser Ile Pro Gln Leu Leu Ser Asp
    210                 215                 220

Asn Leu Leu Tyr Asp Asp Gln Ser Tyr Thr Met Asn Asn Val Ser Asn
225                 230                 235                 240

Thr Ser Asn Val Asp Gln Val Ser Ser Gln Gln Asn Thr Asn Asn
                245                 250                 255

Ile Thr Ser Asn Asn Cys Asn Ile Phe Phe Asn Tyr Gln Gln Pro Leu
            260                 265                 270

Phe Val Asn Pro Thr Phe Gln Ser Gln
        275                 280

<210> SEQ ID NO 6
<211> LENGTH: 268
<212> TYPE: PRT
<213> ORGANISM: Arabidopsis thaliana

<400> SEQUENCE: 6

Met Glu Val Thr Ser Gln Ser Thr Leu Pro Pro Gly Phe Arg Phe His
1               5                   10                  15

Pro Thr Asp Glu Glu Leu Ile Val Tyr Tyr Leu Arg Asn Gln Thr Met
                20                  25                  30

Ser Lys Pro Cys Pro Val Ser Ile Ile Pro Glu Val Asp Ile Tyr Lys

```
                 35                  40                  45
Phe Asp Pro Trp Gln Leu Pro Glu Lys Thr Glu Phe Gly Glu Asn Glu
 50                  55                  60

Trp Tyr Phe Phe Ser Pro Arg Glu Arg Lys Tyr Pro Asn Gly Val Arg
 65                  70                  75                  80

Pro Asn Arg Ala Ala Val Ser Gly Tyr Trp Lys Ala Thr Gly Thr Asp
                 85                  90                  95

Lys Ala Ile His Ser Gly Ser Asn Val Gly Val Lys Lys Ala Leu
                100                 105                 110

Val Phe Tyr Lys Gly Arg Pro Pro Lys Gly Ile Lys Thr Asp Trp Ile
                115                 120                 125

Met His Glu Tyr Arg Leu His Asp Ser Arg Lys Ala Ser Thr Lys Arg
130                 135                 140

Asn Gly Ser Met Arg Leu Asp Glu Trp Val Leu Cys Arg Ile Tyr Lys
145                 150                 155                 160

Lys Arg Gly Ala Ser Lys Leu Leu Asn Glu Gln Glu Gly Phe Met Asp
                165                 170                 175

Glu Val Leu Met Glu Asp Glu Thr Lys Val Val Val Asn Glu Ala Glu
                180                 185                 190

Arg Arg Thr Glu Glu Glu Ile Met Met Met Thr Ser Met Lys Leu Pro
                195                 200                 205

Arg Thr Cys Ser Leu Ala His Leu Leu Glu Met Asp Tyr Met Gly Pro
210                 215                 220

Val Ser His Ile Asp Asn Phe Ser Gln Phe Asp His Leu His Gln Pro
225                 230                 235                 240

Asp Ser Glu Ser Ser Trp Phe Gly Asp Leu Gln Phe Asn Gln Asp Glu
                245                 250                 255

Ile Leu Asn His His Arg Gln Ala Met Phe Lys Phe
                260                 265

<210> SEQ ID NO 7
<211> LENGTH: 354
<212> TYPE: PRT
<213> ORGANISM: Triticum aestivum

<400> SEQUENCE: 7

Met Pro Met Gly Ser Ser Ala Ala Met Pro Ala Leu Pro Pro Gly Phe
 1               5                  10                  15

Arg Phe His Pro Thr Asp Glu Glu Leu Ile Val His Tyr Leu Arg Arg
                20                  25                  30

Gln Ala Ala Ser Met Pro Ser Pro Val Pro Ile Ile Ala Glu Val Asn
                35                  40                  45

Ile Tyr Lys Cys Asn Pro Trp Asp Leu Pro Gly Lys Ala Leu Phe Gly
 50                  55                  60

Glu Asn Glu Trp Tyr Phe Phe Ser Pro Arg Asp Arg Lys Tyr Pro Asn
 65                  70                  75                  80

Gly Ala Arg Pro Asn Arg Ala Ala Gly Ser Gly Tyr Trp Lys Ala Thr
                 85                  90                  95

Gly Thr Asp Lys Ala Ile Leu Ser Thr Pro Ala Asn Glu Ser Ile Gly
                100                 105                 110

Val Lys Lys Ala Leu Val Phe Tyr Arg Gly Lys Pro Pro Lys Gly Val
                115                 120                 125

Lys Thr Asp Trp Ile Met His Glu Tyr Arg Leu Thr Ala Ala Asp Asn
130                 135                 140

Arg Thr Thr Lys Arg Arg Gly Ser Ser Met Arg Leu Asp Asp Trp Val
```

```
                145                 150                 155                 160
Leu Cys Arg Ile His Lys Lys Cys Gly Asn Leu Pro Asn Phe Ser Ser
                                165                 170                 175

Ser Asp Gln Glu Gln Glu His Glu Gln Glu Ser Ser Thr Val Glu Asp
                180                 185                 190

Ser Gln Asn Asn His Thr Val Ser Ser Pro Lys Ser Glu Ala Phe Asp
            195                 200                 205

Gly Asp Gly Asp Asp His Leu Gln Leu Gln Gln Phe Arg Pro Met Ala
        210                 215                 220

Ile Ala Lys Ser Cys Ser Leu Thr Asp Leu Leu Asn Thr Val Asp Tyr
225                 230                 235                 240

Ala Ala Leu Ser His Leu Leu Leu Asp Gly Ala Gly Ala Ser Ser Ser
                245                 250                 255

Asp Ala Gly Ala Asp Tyr Gln Leu Pro Pro Glu Asn Pro Leu Ile Tyr
            260                 265                 270

Ser Gln Pro Pro Trp Gln Gln Thr Leu His Tyr Asn Asn Asn Asn Gly
        275                 280                 285

Tyr Val Asn Asn Glu Thr Ile Asp Val Pro Gln Leu Pro Glu Ala Arg
    290                 295                 300

Val Asp Asp Tyr Gly Met Asn Gly Asp Lys Tyr Asn Gly Met Lys Arg
305                 310                 315                 320

Lys Arg Ser Ser Gly Ser Leu Tyr Cys Ser Gln Leu Gln Leu Pro Ala
                325                 330                 335

Asp Gln Tyr Ser Gly Met Leu Ile His Pro Phe Leu Ser Gln Gln Leu
            340                 345                 350

His Met

<210> SEQ ID NO 8
<211> LENGTH: 392
<212> TYPE: PRT
<213> ORGANISM: Oryza sativa

<400> SEQUENCE: 8

Met Val Leu Ser Asn Pro Ala Met Leu Pro Pro Gly Phe Arg Phe His
1               5                   10                  15

Pro Thr Asp Glu Glu Leu Ile Val His Tyr Leu Arg Asn Arg Ala Ala
                20                  25                  30

Ser Ser Pro Cys Pro Val Ser Ile Ile Ala Asp Val Asp Ile Tyr Lys
            35                  40                  45

Phe Asp Pro Trp Asp Leu Pro Ser Lys Glu Asn Tyr Gly Asp Arg Glu
        50                  55                  60

Trp Tyr Phe Phe Ser Pro Arg Asp Arg Lys Tyr Pro Asn Gly Ile Arg
65                  70                  75                  80

Pro Asn Arg Ala Ala Gly Ser Gly Tyr Trp Lys Ala Thr Gly Thr Asp
                85                  90                  95

Lys Pro Ile His Ser Ser Gly Gly Ala Ala Thr Asn Glu Ser Val Gly
            100                 105                 110

Val Lys Lys Ala Leu Val Phe Tyr Lys Gly Arg Pro Pro Lys Gly Thr
        115                 120                 125

Lys Thr Asn Trp Ile Met His Glu Tyr Arg Leu Ala Ala Ala Asp Ala
    130                 135                 140

His Ala Ala Asn Thr Tyr Arg Pro Met Lys Phe Arg Asn Thr Ser Met
145                 150                 155                 160

Arg Leu Asp Asp Trp Val Leu Cys Arg Ile Tyr Lys Lys Ser Ser His
                165                 170                 175
```

```
Ala Ser Pro Leu Ala Val Pro Pro Leu Ser Asp His Glu Gln Asp Glu
            180                 185                 190

Pro Cys Ala Leu Glu Glu Asn Ala Pro Leu Tyr Ala Pro Ser Ser Ser
            195                 200                 205

Ser Ala Ser Met Ile Leu Gln Gly Ala Ala Gly Ala Phe Pro
            210                 215                 220

Ser Leu His Ala Ala Ala Ala Thr Gln Arg Thr Ala Met Gln Lys
225                 230                 235                 240

Ile Pro Ser Ile Ser Asp Leu Leu Asn Glu Tyr Ser Leu Ser Gln Leu
                245                 250                 255

Phe Asp Asp Gly Gly Ala Ala Ala Ala Pro Leu Gln Glu Met Ala
            260                 265                 270

Arg Gln Pro Asp His His His Gln Gln Gln Gln His Ala Leu Phe
            275                 280                 285

Gly His Pro Val Met Asn His Phe Ile Ala Asn Asn Ser Met Val Gln
            290                 295                 300

Leu Ala His Leu Asp Pro Ser Ser Ser Ala Ala Ala Ser Thr Ser Ala
305                 310                 315                 320

Gly Ala Val Val Glu Pro Ala Val Thr Gly Lys Arg Lys Arg Ser
            325                 330                 335

Ser Asp Gly Gly Glu Pro Thr Ile Gln Ala Leu Pro Pro Ala Ala Ala
            340                 345                 350

Ala Ala Lys Lys Pro Asn Gly Ser Cys Val Gly Ala Thr Phe Gln Ile
            355                 360                 365

Gly Ser Ala Leu Gln Gly Ser Ser Leu Gly Leu Ser His Gln Met Leu
            370                 375                 380

Leu His Ser Asn Met Gly Met Asn
385                 390

<210> SEQ ID NO 9
<211> LENGTH: 163
<212> TYPE: PRT
<213> ORGANISM: Zea mays

<400> SEQUENCE: 9

Met Val Met Ala Asn Pro Asp Met Leu Pro Pro Gly Phe Arg Phe His
1               5                   10                  15

Pro Thr Asp Glu Glu Leu Ile Leu His Tyr Leu Arg Asn Arg Ala Ala
            20                  25                  30

Asn Ala Pro Cys Pro Val Ala Ile Ala Asp Val Asp Ile Tyr Lys
            35                  40                  45

Phe Asp Pro Trp Asp Leu Pro Arg Ala Ala Tyr Gly Asp Lys Glu Trp
 50                 55                  60

Tyr Phe Phe Ser Pro Arg Asp Arg Lys Tyr Pro Asn Gly Ile Arg Pro
 65                 70                  75                  80

Asn Arg Ala Ala Gly Ser Gly Tyr Trp Lys Ala Thr Gly Thr Asp Lys
                85                  90                  95

Pro Ile His Ser Ser Thr Thr Ala Gly Glu Ser Val Gly Val Lys Lys
            100                 105                 110

Ala Leu Val Phe Tyr Glu Gly Arg Pro Pro Lys Gly Thr Lys Thr Asn
            115                 120                 125

Trp Ile Met His Glu Tyr Arg Leu Ala Ala Asp Ala Gln Ala Ala His
            130                 135                 140

Ala Tyr Arg Pro Met Lys Phe Arg Asn Ala Ser Met Arg Val Arg Arg
145                 150                 155                 160
```

Thr Leu Leu

<210> SEQ ID NO 10
<211> LENGTH: 363
<212> TYPE: PRT
<213> ORGANISM: Prunus persica

<400> SEQUENCE: 10

```
Met Glu Ser Thr Asp Ser Ser Thr Ala Ser Gln Gln Gln Gln Gln
1               5                   10                  15

Gln Pro Gln Pro Pro Gln Pro Asn Leu Pro Pro Gly Phe Arg Phe
            20                  25                  30

His Pro Thr Asp Glu Glu Leu Val Val His Tyr Leu Lys Lys Val
            35                  40                  45

Thr Ser Ala Pro Leu Pro Val Ala Ile Ile Ala Glu Ile Glu Leu Tyr
        50                  55                  60

Lys Phe Asp Pro Trp Glu Leu Pro Ala Lys Ala Thr Phe Gly Glu Gln
65                  70                  75                  80

Glu Trp Tyr Phe Phe Ser Pro Arg Asp Arg Lys Tyr Pro Asn Gly Ala
                85                  90                  95

Arg Pro Asn Arg Ala Ala Thr Ser Gly Tyr Trp Lys Ala Thr Gly Thr
            100                 105                 110

Asp Lys Pro Val Leu Thr Ser Gly Thr Gln Lys Val Gly Val Lys
            115                 120                 125

Lys Ala Leu Val Phe Tyr Gly Gly Lys Pro Pro Lys Gly Ile Lys Thr
130                 135                 140

Asn Trp Ile Met His Glu Tyr Arg Leu Ala Asp Ser Lys Thr Ser Asn
145                 150                 155                 160

Lys Pro Pro Gly Cys Asp Leu Gly Asn Lys Lys Asn Ser Leu Arg Leu
                165                 170                 175

Asp Asp Trp Val Leu Cys Arg Ile Tyr Lys Lys Asn Asn Ser His Arg
            180                 185                 190

Pro Met Asp Leu Glu Arg Glu Asp Ser Met Glu Asp Met Met Gly Pro
            195                 200                 205

Leu Met Pro Pro Ser Ile Ser His Val Gly His His Gln Asn Met Asn
210                 215                 220

Leu His Leu Pro Lys Ser Asn Thr Asn Tyr Gly Pro Pro Phe Ile Glu
225                 230                 235                 240

Asn Asp Gln Ile Ile Phe Asp Gly Ile Met Ser Ser Thr Asp Gly Ser
                245                 250                 255

Ala Ser Leu Ser Asn Gly Thr Ser Gln Leu Pro Leu Lys Arg Ser Ile
            260                 265                 270

Val Pro Ser Leu Tyr Arg Asn Asp Gln Glu Asp Asp Gln Thr Ala Gly
            275                 280                 285

Ala Ser Ser Ser Lys Arg Val Val Gln Leu His Gln Leu Asp Ser Gly
            290                 295                 300

Thr Asn Asn Ser Val Ala Ala Asn Asn Ser Thr Ser Ile Ala Asn
305                 310                 315                 320

Leu Leu Ser Gln Leu Pro Gln Thr Pro Pro Leu His Gln His Ala Met
                325                 330                 335

Leu Gly Ser Leu Gly Asp Gly Leu Phe Arg Thr Pro Tyr Gln Leu Pro
            340                 345                 350

Gly Met Asn Trp Phe Ser Glu Ser Asn Leu Gly
            355                 360
```

```
<210> SEQ ID NO 11
<211> LENGTH: 355
<212> TYPE: PRT
<213> ORGANISM: Lycopersicon esculentum

<400> SEQUENCE: 11

Met Glu Ser Thr Asp Ser Ser Thr Gly Thr Arg His Gln Pro Gln Leu
1               5                   10                  15

Pro Pro Gly Phe Arg Phe His Pro Thr Asp Glu Glu Leu Ile Val His
            20                  25                  30

Tyr Leu Lys Lys Arg Val Ala Gly Ala Pro Ile Pro Val Asp Ile Ile
        35                  40                  45

Gly Glu Ile Asp Leu Tyr Lys Phe Asp Pro Trp Glu Leu Pro Ala Lys
50                  55                  60

Ala Ile Phe Gly Glu Gln Glu Trp Phe Phe Phe Ser Pro Arg Asp Arg
65                  70                  75                  80

Lys Tyr Pro Asn Gly Ala Arg Pro Asn Arg Ala Ala Thr Ser Gly Tyr
            85                  90                  95

Trp Lys Ala Thr Gly Thr Asp Lys Pro Val Phe Thr Ser Gly Gly Thr
        100                 105                 110

Gln Lys Val Gly Val Lys Lys Ala Leu Val Phe Tyr Gly Gly Lys Pro
    115                 120                 125

Pro Lys Gly Val Lys Thr Asn Trp Ile Met His Glu Tyr Arg Val Val
130                 135                 140

Glu Asn Lys Thr Asn Asn Lys Pro Leu Gly Cys Asp Asn Ile Val Ala
145                 150                 155                 160

Asn Lys Lys Gly Ser Leu Arg Leu Asp Asp Trp Val Leu Cys Arg Ile
            165                 170                 175

Tyr Lys Lys Asn Asn Thr Gln Arg Ser Ile Asp Asp Leu His Asp Met
        180                 185                 190

Leu Gly Ser Ile Pro Gln Asn Val Pro Asn Ser Ile Leu Gln Gly Ile
    195                 200                 205

Lys Pro Ser Asn Tyr Gly Thr Ile Leu Leu Glu Asn Glu Ser Asn Met
210                 215                 220

Tyr Asp Gly Ile Met Asn Asn Thr Asn Asp Ile Ile Asn Asn Asn Asn
225                 230                 235                 240

Arg Ser Ile Pro Gln Ile Ser Ser Lys Arg Thr Met His Gly Gly Leu
            245                 250                 255

Tyr Trp Asn Asn Asp Glu Ala Thr Thr Thr Thr Thr Ile Asp Arg
        260                 265                 270

Asn His Ser Pro Asn Thr Lys Arg Phe Leu Val Glu Asn Asn Glu Asp
    275                 280                 285

Asp Gly Leu Asn Met Asn Asn Ile Ser Arg Ile Thr Asn His Glu Gln
290                 295                 300

Ser Ser Ser Ile Ala Asn Phe Leu Ser Gln Phe Pro Gln Asn Pro Ser
305                 310                 315                 320

Ile Gln Gln Gln Gln Gln Gln Glu Glu Val Leu Gly Ser Leu Asn
            325                 330                 335

Asp Gly Val Val Phe Arg Gln Pro Tyr Asn Gln Val Thr Gly Met Asn
            340                 345                 350

Trp Tyr Ser
        355

<210> SEQ ID NO 12
<211> LENGTH: 304
```

```
<212> TYPE: PRT
<213> ORGANISM: Petunia x hybrida

<400> SEQUENCE: 12

Met Thr Thr Ala Glu Leu Gln Leu Pro Pro Gly Phe Arg Phe His Pro
1               5                   10                  15

Thr Asp Glu Glu Leu Val Met His Tyr Leu Cys Arg Lys Cys Ala Ser
            20                  25                  30

Gln Pro Ile Ala Val Pro Ile Ala Glu Ile Asp Leu Tyr Lys Tyr
        35                  40                  45

Asp Pro Trp Asp Leu Pro Asp Leu Ala Leu Tyr Gly Glu Lys Glu Trp
        50                  55                  60

Tyr Phe Phe Ser Pro Arg Asp Arg Lys Tyr Pro Asn Gly Ser Arg Pro
65                  70                  75                  80

Asn Arg Ala Ala Gly Thr Gly Tyr Trp Lys Ala Thr Gly Ala Asp Lys
                85                  90                  95

Pro Ile Gly His Pro Lys Ala Val Gly Ile Lys Lys Ala Leu Val Phe
            100                 105                 110

Tyr Ala Gly Lys Ala Pro Lys Gly Glu Lys Thr Asn Trp Ile Met His
        115                 120                 125

Glu Tyr Arg Leu Ala Asp Val Asp Arg Ser Ala Arg Lys Asn Asn Asn
    130                 135                 140

Ser Leu Arg Leu Asp Asp Trp Val Leu Cys Arg Ile Tyr Asn Lys Lys
145                 150                 155                 160

Gly Ser Ile Glu Lys Asn Gln Leu Asn Asn Lys Lys Ile Met Asn Thr
                165                 170                 175

Ser Tyr Met Asp Met Thr Val Ser Ser Glu Glu Asp Arg Lys Pro Glu
            180                 185                 190

Ile Leu Pro Pro Leu Pro Pro Gln Pro Ala Pro Gln Gln Gln Gln Val
        195                 200                 205

Tyr Asn Asp Phe Phe Tyr Leu Asp Pro Ser Asp Ser Val Pro Lys Ile
    210                 215                 220

His Ser Asp Ser Ser Cys Ser Glu His Val Val Ser Pro Glu Phe Thr
225                 230                 235                 240

Cys Glu Arg Glu Val Gln Ser Glu Ala Lys Leu Ser Glu Trp Glu Lys
                245                 250                 255

Ala Ala Leu Asp Leu Pro Phe Asn Tyr Met Asp Ala Thr Thr Gly Ala
            260                 265                 270

Thr Thr Leu Asp Asn Ser Leu Leu Gly Ser Gln Phe Gln Ser Ser Tyr
        275                 280                 285

Gln Met Ser Pro Leu Gln Asp Met Phe Met His Leu His Lys Pro Phe
    290                 295                 300

<210> SEQ ID NO 13
<211> LENGTH: 349
<212> TYPE: PRT
<213> ORGANISM: Solanum tuberosum

<400> SEQUENCE: 13

Met Gly Val Gln Glu Lys Tyr Pro Leu Leu Gln Leu Ser Leu Pro Pro
1               5                   10                  15

Gly Phe Arg Phe Tyr Pro Thr Asp Glu Glu Leu Leu Val Gln Tyr Leu
            20                  25                  30

Cys Lys Lys Val Ala Gly His Asp Phe Pro Leu Gln Ile Ile Gly Glu
        35                  40                  45

Ile Asp Leu Tyr Lys Phe Asp Pro Trp Val Leu Pro Ser Lys Ala Thr
```

```
                50                  55                  60
Phe Gly Glu Lys Glu Trp Tyr Phe Phe Ser Pro Arg Asp Arg Lys Tyr
 65                  70                  75                  80

Pro Asn Gly Ser Arg Pro Asn Arg Val Ala Gly Ser Gly Tyr Trp Lys
                 85                  90                  95

Ala Thr Gly Thr Asp Lys Ile Ile Thr Ser Gln Gly Arg Lys Val Gly
                100                 105                 110

Ile Lys Lys Ala Leu Val Phe Tyr Val Gly Lys Ala Pro Lys Gly Ser
                115                 120                 125

Lys Thr Asn Trp Ile Met His Glu Tyr Arg Leu Phe Glu Ser Ser Lys
                130                 135                 140

Lys Asn Asn Gly Ser Ser Lys Leu Asp Glu Trp Val Leu Cys Arg Ile
145                 150                 155                 160

Tyr Lys Lys Asn Ser Ser Gly Pro Lys Pro Leu Met Ser Gly Leu His
                165                 170                 175

Ser Ser Asn Glu Tyr Ser His Gly Ser Ser Thr Ser Ser Ser Ser Gln
                180                 185                 190

Phe Asp Asp Met Leu Glu Ser Leu Pro Glu Met Asp Asp Arg Phe Ser
                195                 200                 205

Asn Leu Pro Arg Leu Asn Ser Leu Lys Thr Glu Lys Leu Asn Leu Glu
210                 215                 220

Arg Leu Asp Ser Ala Asn Phe Asp Trp Ala Ile Leu Ala Gly Leu Lys
225                 230                 235                 240

Pro Met Pro Glu Leu Arg Pro Ala Asn Gln Ala Pro Gly Val Gln Gly
                245                 250                 255

Gln Gly Gln Ala Gln Gly Asn Val Asn His Asn Asn Asn Asn Asn Met
                260                 265                 270

Asn Phe Leu Asn Asp Val Tyr Ala His Pro Thr Thr Asn Phe Arg Gly
                275                 280                 285

Asn Thr Lys Val Glu Ser Ile Asn Leu Asp Glu Val Glu Ser Gly
                290                 295                 300

Asn Arg Asn Arg Arg Ile Asp Gln Ser Ser Tyr Phe Gln Gln Ser Leu
305                 310                 315                 320

Asn Gly Phe Ser Gln Ala Tyr Thr Asn Ser Val Asp Gln Phe Gly Ile
                325                 330                 335

Gln Cys Pro Asn Gln Thr Leu Asn Leu Gly Phe Arg Gln
                340                 345

<210> SEQ ID NO 14
<211> LENGTH: 22
<212> TYPE: DNA
<213> ORGANISM: Artificial
<220> FEATURE:
<223> OTHER INFORMATION: Primer

<400> SEQUENCE: 14
gcgtggaccg cttgctgcaa ct                                              22

<210> SEQ ID NO 15
<211> LENGTH: 23
<212> TYPE: DNA
<213> ORGANISM: Artificial
<220> FEATURE:
<223> OTHER INFORMATION: Primer

<400> SEQUENCE: 15
atcatggaag taacttccca atc                                             23
```

```
<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
ttcagttctt ctctctgctt c                                          21

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
ggccattttc tacgctacct                                            20

<210> SEQ ID NO 18
<211> LENGTH: 25
<212> TYPE: DNA
<213> ORGANISM: Artificial
<220> FEATURE:
<223> OTHER INFORMATION: Primer

<400> SEQUENCE: 18
cttccatggt tttcagacaa tttag                                      25

<210> SEQ ID NO 19
<211> LENGTH: 29
<212> TYPE: DNA
<213> ORGANISM: Artificial
<220> FEATURE:
<223> OTHER INFORMATION: Primer

<400> SEQUENCE: 19
tagtcgacag ttcctgttct attagattg                                  29

<210> SEQ ID NO 20
<211> LENGTH: 27
<212> TYPE: DNA
<213> ORGANISM: Artificial
<220> FEATURE:
<223> OTHER INFORMATION: Primer

<400> SEQUENCE: 20
tatcatgaac ttaaacatcg cttgacg                                    27

<210> SEQ ID NO 21
<211> LENGTH: 25
<212> TYPE: DNA
<213> ORGANISM: Artificial
<220> FEATURE:
<223> OTHER INFORMATION: Primer

<400> SEQUENCE: 21
cactagttcc tgttctatta gattg                                      25

<210> SEQ ID NO 22
<211> LENGTH: 25
<212> TYPE: DNA
<213> ORGANISM: Artificial
<220> FEATURE:
<223> OTHER INFORMATION: Primer
```

-continued

```
<400> SEQUENCE: 22
gctgcagtaa cttttcaagc acatc                                          25

<210> SEQ ID NO 23
<211> LENGTH: 24
<212> TYPE: DNA
<213> ORGANISM: Artificial
<220> FEATURE:
<223> OTHER INFORMATION: Primer

<400> SEQUENCE: 23
gcgtcatctc atcctaatcc tcat                                           24

<210> SEQ ID NO 24
<211> LENGTH: 23
<212> TYPE: DNA
<213> ORGANISM: Artificial
<220> FEATURE:
<223> OTHER INFORMATION: Primer

<400> SEQUENCE: 24
cgtgacttcg tcttatcatg ctg                                            23

<210> SEQ ID NO 25
<211> LENGTH: 31
<212> TYPE: DNA
<213> ORGANISM: Artificial
<220> FEATURE:
<223> OTHER INFORMATION: Primer

<400> SEQUENCE: 25
ttctgcagcg tcatctcatc ctaatcctca t                                   31

<210> SEQ ID NO 26
<211> LENGTH: 29
<212> TYPE: DNA
<213> ORGANISM: Artificial
<220> FEATURE:
<223> OTHER INFORMATION: Primer

<400> SEQUENCE: 26
gttacttcca tggttttcag acaatttag                                      29

<210> SEQ ID NO 27
<211> LENGTH: 22
<212> TYPE: DNA
<213> ORGANISM: Artificial
<220> FEATURE:
<223> OTHER INFORMATION: Primer

<400> SEQUENCE: 27
ttccatggtt ctgtcgaacc cg                                             22

<210> SEQ ID NO 28
<211> LENGTH: 26
<212> TYPE: DNA
<213> ORGANISM: Artificial
<220> FEATURE:
<223> OTHER INFORMATION: Primer

<400> SEQUENCE: 28
gatctagacg aagaacgagc tatcag                                         26

<210> SEQ ID NO 29
<211> LENGTH: 35
<212> TYPE: DNA
```

-continued

<213> ORGANISM: Artificial
<220> FEATURE:
<223> OTHER INFORMATION: Primer

<400> SEQUENCE: 29
aagtcgacga ttttcagaca atttagaaaa caatc					35

<210> SEQ ID NO 30
<211> LENGTH: 28
<212> TYPE: DNA
<213> ORGANISM: Artificial
<220> FEATURE:
<223> OTHER INFORMATION: Primer

<400> SEQUENCE: 30
aagtcgacat ggatgctacc acaccctc					28

<210> SEQ ID NO 31
<211> LENGTH: 26
<212> TYPE: DNA
<213> ORGANISM: Artificial
<220> FEATURE:
<223> OTHER INFORMATION: Primer

<400> SEQUENCE: 31
gatctagatg gacgaagctt atcgtc					26

<210> SEQ ID NO 32
<211> LENGTH: 18
<212> TYPE: DNA
<213> ORGANISM: Artificial
<220> FEATURE:
<223> OTHER INFORMATION: Primer

<400> SEQUENCE: 32
cagctgcgga tgttgttg					18

<210> SEQ ID NO 33
<211> LENGTH: 19
<212> TYPE: DNA
<213> ORGANISM: Artificial
<220> FEATURE:
<223> OTHER INFORMATION: Primer

<400> SEQUENCE: 33
ccactttctc cccattttg					19

<210> SEQ ID NO 34
<211> LENGTH: 18
<212> TYPE: DNA
<213> ORGANISM: Artificial
<220> FEATURE:
<223> OTHER INFORMATION: Primer

<400> SEQUENCE: 34
gcaaccaaag gagccatg					18

<210> SEQ ID NO 35
<211> LENGTH: 19
<212> TYPE: DNA
<213> ORGANISM: Artificial
<220> FEATURE:
<223> OTHER INFORMATION: Primer

<400> SEQUENCE: 35
gtttggccaa ctagtctgc					19

```
<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
agtaatggct tcctctatgc                                                  20

<210> SEQ ID NO 37
<211> LENGTH: 20
<212> TYPE: DNA
<213> ORGANISM: Artificial
<220> FEATURE:
<223> OTHER INFORMATION: Primer

<400> SEQUENCE: 37
ggcttgtagg caatgaaact                                                  20

<210> SEQ ID NO 38
<211> LENGTH: 18
<212> TYPE: DNA
<213> ORGANISM: Artificial
<220> FEATURE:
<223> OTHER INFORMATION: Primer

<400> SEQUENCE: 38
atcccttcca tttccgac                                                    18

<210> SEQ ID NO 39
<211> LENGTH: 18
<212> TYPE: DNA
<213> ORGANISM: Artificial
<220> FEATURE:
<223> OTHER INFORMATION: Primer

<400> SEQUENCE: 39
ctgggtcttg tgcagaat                                                    18

<210> SEQ ID NO 40
<211> LENGTH: 22
<212> TYPE: DNA
<213> ORGANISM: Artificial
<220> FEATURE:
<223> OTHER INFORMATION: Primer

<400> SEQUENCE: 40
tctagaggca aaagaggact ac                                               22

<210> SEQ ID NO 41
<211> LENGTH: 24
<212> TYPE: DNA
<213> ORGANISM: Artificial
<220> FEATURE:
<223> OTHER INFORMATION: Primer

<400> SEQUENCE: 41
ggatcctggt acttccctga atct                                             24

<210> SEQ ID NO 42
<211> LENGTH: 30
<212> TYPE: DNA
<213> ORGANISM: Artificial
<220> FEATURE:
<223> OTHER INFORMATION: Primer
```

```
<400> SEQUENCE: 42
taggccttga tgcatgttgt caatcaattg                                        30

<210> SEQ ID NO 43
<211> LENGTH: 20
<212> TYPE: DNA
<213> ORGANISM: Artificial
<220> FEATURE:
<223> OTHER INFORMATION: Primer

<400> SEQUENCE: 43
tctagacgga gctgttcaac                                                   20

<210> SEQ ID NO 44
<211> LENGTH: 21
<212> TYPE: DNA
<213> ORGANISM: Artificial
<220> FEATURE:
<223> OTHER INFORMATION: Primer

<400> SEQUENCE: 44
aagcttagag tgaagcggca t                                                 21

<210> SEQ ID NO 45
<211> LENGTH: 25
<212> TYPE: DNA
<213> ORGANISM: Artificial
<220> FEATURE:
<223> OTHER INFORMATION: Primer

<400> SEQUENCE: 45
ggaattcgcc cggggatctc ctttg                                             25
```

USE OF NAP GENE TO MANIPULATE LEAF SENESCENCE IN PLANTS

This application is a national state application under 35 U.S.C. §371 of PCT/US2007/065321, filed Mar. 28, 2007, which claims the benefit of U.S. Provisional Patent Application Ser. No. 60/786,602, filed Mar. 28, 2006, each of which is hereby incorporated by reference in its entirety.

This invention was made with government support under Grant No. DE-FG02-02ER15341 awarded by the U.S. Department of Energy Basic Energy Sciences and Grant No. IS-3645-04 awarded by the U.S.-Israel Binational Agricultural Research and Development (BARD) Fund. The U.S. Government has certain rights in this invention.

FIELD OF THE INVENTION

The present invention relates to transgenic plants having an altered level of NAP protein compared to that of a non-transgenic plant, where the transgenic plants display an altered leaf senescence phenotype relative to a non-transgenic plant. The present invention also relates to mutant plants comprising an inactivated NAP gene, where mutant plants display a delayed leaf senescence phenotype compared to that of a non-mutant plant. In addition, the present invention relates to methods for delaying leaf senescence in a plant, as well as methods for causing precocious leaf senescence or promoting leaf senescence in a plant. The present invention also relates to methods of identifying a candidate plant suitable for breeding that displays a delayed leaf senescence and/or enhanced yield phenotype.

BACKGROUND OF THE INVENTION

The transition from a functional photosynthetic organ to an actively degenerating and nutrient-recycling tissue in a leaf's life history represents the onset of leaf senescence. This onset is a developmental switch that involves dramatic differential gene expression. Differential gene expression is believed to play an important role in leaf senescence. In a senescing leaf, many genes that are expressed in green leaves, including those genes involved in photosynthesis, are down-regulated, while a subset of genes, generally referred to as senescence-associated genes (SAGs), are up-regulated. Leaf senescence is under direct nuclear control, and SAG expression is required for senescence to proceed. Inhibitors of transcription or translation prevent leaves from senescing (Buchanan-Wollaston et al., "The Molecular Analysis of Leaf Senescence—A Genomics Approach," *Plant Biotechnology Journal* 1:3-22 (2003); Guo et al., "Leaf Senescence: Signals, Execution, and Regulation," *Current Topics in Developmental Biology* 71:82-112 (2005); Hadfield et al., "Programmed Senescence of Plant Organs," *Cell Death Differ.* 4:662-670 (1997); Lim et al., "The Molecular and Genetic Control of Leaf Senescence and Longevity in *Arabidopsis*," *Current Topics in Developmental Biology* 67:49-83 (2005); Smart, "Gene Expression During Leaf Senescence," *New Phytologist* 126:419-448 (1994)). For the past decade, much effort has been made to isolate SAGs, and hundreds of SAGs have been cloned from various plant species including *Arabidopsis*, barley, *Brassica*, maize, cucumber, rice, tobacco, radish, asparagus and soybean (Buchanan-Wollaston et al., "The Molecular Analysis of Leaf Senescence—A Genomics Approach," *Plant Biotechnology Journal* 1:3-22 (2003); Gepstein et al., "Large-Scale Identification of Leaf Senescence-Associated Genes," *Plant Journal* 36:629-642 (2003); He et al., "Molecular Characteristics of Leaf Senescence," In *Recent Research Developments in Plant Molecular Biology*, Kerala, India: Research Signpost, pp. 1-17 (2003)). Recent application of genomics approaches has led to the identification of thousands of potential SAGs (Andersson et al., "A Transcriptional Timetable of Autumn Senescence," *Genome Biology* 5:R24 (2004); Bhalerao et al., "Gene Expression in Autumn Leaves," *Plant Physiology* 131:430-442 (2003); Buchanan-Wollaston et al., "The Molecular Analysis of Leaf Senescence—A Genomics Approach," *Plant Biotechnology Journal* 1:3-22 (2003); Buchanan-Wollaston et al., "Comparative Transcriptome Analysis Reveals Significant Differences in Gene Expression and Signalling Pathways Between Developmental and Dark/Starvation-Induced Senescence in *Arabidopsis*," *The Plant Journal* 42:567-585 (2005); Guo et al., "Transcriptome of *Arabidopsis* Leaf Senescence," *Plant Cell and Environment* 27:521-549 (2004); Lin et al., "Molecular Events in Senescing *Arabidopsis* Leaves," *Plant Journal* 39:612-628 (2004); Zentgraf et al., "Senescence—Related Gene Expression Profiles of Rosette Leaves of *Arabidopsis Thaliana*: Leaf Age Versus Plant Age," *Plant Biology* 6:178-183 (2004)). Analysis of a leaf senescence EST database (dbEST) indicated that approximately 10% (approximately 2500) of the *Arabidopsis* genes are expressed in senescent leaves (Guo et al., "Transcriptome of *Arabidopsis* Leaf Senescence," *Plant Cell and Environment* 27:521-549 (2004)). Microarray analysis of the global gene expression changes during developmental leaf senescence in *Arabidopsis* has led to the identification of more than 800 genes that show a reproducible increase in transcript abundance (Buchanan-Wollaston et al., "Comparative Transcriptome Analysis Reveals Significant Differences in Gene Expression and Signalling Pathways Between Developmental and Dark/Starvation-Induced Senescence in *Arabidopsis*," *The Plant Journal* 42:567-585 (2005)).

Changes of gene expression are often regulated by transcription factors that bind to specific cis elements of target gene promoters, resulting in the activation and/or suppression of the target genes. There are approximately 1500 transcription factor genes in the *Arabidopsis* genome that belong to more than 30 gene families based on their DNA-binding domains (Riechmann et al., "*Arabidopsis* Transcription Factors: Genome-Wide Comparative Analysis Among Eukaryotes," *Science* 290:2105-2110 (2000)). Microarray analysis has identified 96 transcription factor genes with at least a threefold upregulation during leaf senescence (Buchanan-Wollaston et al., "Comparative Transcriptome Analysis Reveals Significant Differences in Gene Expression and Signalling Pathways Between Developmental and Dark/Starvation-Induced Senescence in *Arabidopsis*," *The Plant Journal* 42:567-585 (2005)), and analysis of the leaf senescence dbEST revealed 134 unique genes that encode transcription factors representing 20 different gene families (Guo et al., "Transcriptome of *Arabidopsis* Leaf Senescence," *Plant Cell and Environment* 27:521-549 (2004)). Among the largest transcription factor groups are NAC, WRKY, C2H2 type zinc finger, AP2/EREBP, and MYB proteins (Buchanan-Wollaston et al., "Comparative Transcriptome Analysis Reveals Significant Differences in Gene Expression and Signalling Pathways Between Developmental and Dark/Starvation-Induced Senescence in *Arabidopsis*," *The Plant Journal* 42:567-585 (2005); Chen et al., "Expression Profile Matrix of *Arabidopsis* Transcription Factor Genes Suggests Their Putative Functions in Response to Environmental Stresses," *Plant Cell* 14:559-574 (2002); Guo et al., "Transcriptome of *Arabidopsis* Leaf Senescence," *Plant Cell and Environment* 27:521-549 (2004); Lin et al., "Molecular Events in Senescing *Arabidopsis* Leaves," *Plant Journal* 39:612-628 (2004)). Two WRKY transcription factor genes have been studied: WRKY53 plays an important role in controlling leaf senescence (Hinderhofer et al., "Identification of a Transcription Factor Specifically Expressed at the Onset of Leaf Senescence," *Planta* 213:469-473 (2001); Miao et al., "Targets of the WRKY53 Transcription Factor and Its Role During Leaf Senescence in *Arabidopsis*," *Plant Mol Biol* 55:853-867 (2004); Robatzek et al., "Targets of AtWRKY6 Regulation During Plant Senescence and Pathogen Defense," *Genes Dev* 16:1139-1149 (2002)), while suppression of WRKY6 expression has little effect on either the onset or the progression of leaf senescence (Hinderhofer et al., "Identification of a Transcription Factor Specifically Expressed at the Onset of Leaf Senescence," *Planta* 213:469-473 (2001); Miao et al., "Targets of the WRKY53 Transcription Factor and Its Role During Leaf Senescence in *Arabidopsis*," *Plant Mol Biol* 55:853-867 (2004); Robatzek et al., "Targets of AtWRKY6 Regulation During Plant Senescence and Pathogen Defense," *Genes Dev* 16:1139-1149 (2002)). The potential functions of the majority of the leaf senescence-associated transcription factors remain to be elucidated.

A total of 20 genes encoding NAC transcription factors are in the leaf senescence dbEST (Guo et al., "Transcriptome of *Arabidopsis* Leaf Senescence," *Plant Cell and Environment* 27:521-549 (2004)), representing almost one-fifth of all the predicted 109 members of the NAC superfamily in *Arabidopsis* (Riechmann et al., "*Arabidopsis* Transcription Factors: Genome-Wide Comparative Analysis Among Eukaryotes," *Science* 290:2105-2110 (2000)). The NAC domain was originally defined by the highly conserved N-termini of the petunia NAM (NO APICAL MERISTEM) and *Arabidopsis* ATAF1 and CUC2 (CUP-SHAPED COTYLEDON2) genes. It exists widely in plants but not in other eukaryotes. Roles of the NAC family genes include embryo and shoot meristem development, lateral root formation, auxin signaling, defense, and abiotic stress response (Olsen et al., "NAC Transcription Factors: Structurally Distinct, Functionally Diverse," *Trends Plant Sci* 10:79-87 (2005)). Expression of the NAC family genes in senescing leaves has been reported by several groups (Andersson et al., "A Transcriptional Timetable of Autumn Senescence," *Genome Biology* 5 (2004); Buchanan-Wollaston et al., "Comparative Transcriptome Analysis Reveals Significant Differences in Gene Expression and Signalling Pathways Between Developmental and Dark/Starvation-Induced Senescence in *Arabidopsis*," *The Plant Journal* 42:567-585 (2005); Guo et al., "Transcriptome of *Arabidopsis* Leaf Senescence," *Plant Cell and Environment* 27:521-549 (2004); John et al., "Cloning and Characterization of Tomato Leaf Senescence-Related cDNAs," *Plant Molecular Biology* 33:641-651 (1997); Lin et al., "Molecular Events in Senescing *Arabidopsis* Leaves," *Plant Journal* 39:612-628 (2004)), but whether these genes play a part in leaf senescence is unknown.

The present invention is directed to overcoming these deficiencies in the art.

SUMMARY OF THE INVENTION

The present invention relates to a transgenic plant having an altered level of NAP protein capable of causing leaf senescence in a plant, compared to that of a non-transgenic plant, where the transgenic plant displays an altered leaf senescence phenotype, relative to a non-transgenic plant.

Another aspect of the present invention relates to a mutant plant comprising an inactivated NAP gene, where the mutant plant displays a delayed leaf senescence phenotype, relative to a non-mutant plant.

The present invention also relates to a method for delaying leaf senescence in a plant. The method involves providing a transgenic plant or plant seed transformed with a nucleic acid construct effective in silencing expression of a NAP protein capable of causing leaf senescence in a plant. Then, the transgenic plant or the plant grown from the transgenic plant seed is grown under conditions effective to delay leaf senescence in the transgenic plant or the plant grown from the transgenic plant seed.

Another aspect of the present invention relates to a method for delaying leaf senescence in a plant. The method involves transforming a plant cell with a nucleic acid molecule encoding a NAP protein capable of causing leaf senescence in a plant operably associated with a promoter to obtain a transformed plant cell, where expression of the nucleic acid molecule in the plant cell causes delayed leaf senescence by a form of post-transcriptional gene silencing. Then, a plant is regenerated from the transformed plant cell under conditions effective to delay leaf senescence in the plant.

Another aspect of the present invention relates to a method of making a mutant plant having a decreased level of NAP protein compared to that of a non-mutant plant, where the mutant plant displays a delayed leaf senescence phenotype relative to a non-mutant plant. The method involves providing at least one cell of a non-mutant plant containing a gene encoding a functional NAP protein. Next, the at least one cell of a non-mutant plant is treated under conditions effective to inactivate the gene, thereby yielding at least one mutant plant cell containing an inactivated NAP gene. Then, the at least one mutant plant cell is propagated into a mutant plant, where the mutant plant has a decreased level of NAP protein compared to that of the non-mutant plant and displays a delayed leaf senescence phenotype relative to a non-mutant plant.

Another aspect of the present invention relates to a method for causing precocious leaf senescence or promoting leaf senescence in a plant. The method involves transforming a plant cell with a nucleic acid molecule encoding a NAP protein capable of causing leaf senescence in a plant operably associated with a promoter to obtain a transformed plant cell. Next, a plant is regenerated from the transformed plant cell. Then, the promoter is induced under conditions effective to cause premature or precocious leaf senescence in the plant.

The present invention also relates to a method of identifying a candidate plant suitable for breeding that displays a delayed leaf senescence and/or enhanced yield phenotype. The method involves analyzing the candidate plant for the presence, in its genome, of an inactivated NAP gene.

Leaf senescence is a unique developmental process that is characterized by massive programmed cell death and nutrient recycling. During leaf senescence, chlorophyll and other macromolecules such as proteins, lipids, and nucleic acids are degraded, resulting in a sharp decrease in leaf photosynthetic activity. Leaf senescence may therefore substantially limit crop yield and forest biomass accumulation. Occurrence of senescence after harvest devaluates vegetable crops and ornamental plants during postharvest storage, transportation, and on shelves. Techniques that delay leaf senescence are of agricultural significance. The underlying molecular regulatory mechanisms of leaf senescence are not well understood.

The present application describes the functional analysis of AtNAP, a gene encoding a NAC family transcription factor. Expression of this gene is closely associated with the senescence process of *Arabidopsis* rosette leaves. Leaf senescence in two T-DNA insertion lines of this gene is significantly delayed. The T-DNA knockout plants are otherwise normal. The mutant phenotype can be restored to wild type by the intact AtNAP, as well as by its homologs in rice, kidney bean, soybean, and maize that are also upregulated during leaf senescence. Furthermore, inducible overexpression of AtNAP causes precocious senescence. These data strongly suggest that AtNAP and its homologs play an important role in leaf senescence in *Arabidopsis* and in other plant species.

BRIEF DESCRIPTION OF THE DRAWINGS

FIG. 1 shows the CLUSTAL W (1.82) multiple sequence alignment of NAP proteins from various plants, i.e., kidney bean (SEQ ID NO: 1), *Medicago* (SEQ ID NO: 2), soybean (SEQ ID NO: 3), *Populus* (SEQ ID NO: 4), nightshade (SEQ ID NO: 5), *Arabidopsis* (SEQ ID NO: 6), wheat (SEQ ID NO: 7), rice (SEQ ID NO: 8), maize (SEQ ID NO: 9), peach (SEQ ID NO: 10), tomato (SEQ ID NO: 11), petunia (SEQ ID NO: 12), and potato (SEQ ID NO: 13).

FIG. 2(a) depicts AtNAP expression in leaves at different developmental stages. YL, a young leaf with half the size of fully expanded leaf; NS, a fully expanded, non-senescent leaf; ES, an early senescent leaf, with less than 25% leaf area yellowing; LS, a late senescent leaf, with more than 50% leaf area yellowing. FIG. 2(b) depicts AtNAP expression in leaves 1-12 of a 30-day-old plant. Leaves are counted from the bottom of the rosette. FIG. 2(c) depicts AtNAP expression in different part of a senescing leaf. B, base; M, middle; T, tip. The 18S rRNA autoradiographs (FIGS. 2(a) and 2(c)) and ethidium bromide-stained gel (FIG. 2(b)) indicate the relative amount of total RNA loaded in respective lanes.

FIGS. 3(a) and 3(b) are fluorescent images of the GFP-AtNAP fusion proteins expressed in living onion epidermal cells. FIGS. 3(c) and 3(d) depict the DAPI (4',6'-diamidino 2-phenylindole) staining of the same images to show the positions of the nuclei (indicated by arrows).

FIGS. 4(a)-(b) illustrate the expression of AtNAP in two T-DNA insertion lines. FIG. 4(a) depicts the gene structure of AtNAP and locations of T-DNA inserts. FIG. 4(b) shows the RNA gel blot analysis of AtNAP expression in senescing leaves (approximately 50% yellowing) of wild type, line 1, and line 2 plants.

FIG. 5(a) shows the early stages of plant development in the null mutant (line 1) and WT plants. FIGS. 5(b) and 5(c) show senescence in the mutant lines and WT plants (note: the null plants are otherwise developmentally normal). FIG. 5(d) shows leaves excised from age-matched plants in FIG. 5(c). Leaves were numbered from bottom to top. Under the disclosed growth conditions, an adult *Arabidopsis* (accession Columbia) plant typically produces 12 rosette leaves.

FIG. 6(a) depicts leaf survival curves (combination of leaves 9 and 10) of wild-type (WT, n=27) and line 1 (n=22). FIGS. 6(b)-6(d) show the chlorophyll content (FIG. 6(b)), $F_v/F_m$ ratio (FIG. 6(c)), and ion leakage (FIG. 6(d)) in individual rosette leaves of age-matched WT and line 1 plants. FIG. 6(e) shows the RNA gel blot analysis of SAG12 and RBCS in the 12 rosette leaves of age-matched WT and line 1 plants.

FIG. 7(a) shows the RT-PCR analysis of expression of AtNAP (left lanes), OsNAP (middle lanes), and PvNAP (right lanes) in wild-type (WT), atnap null mutant, and atnap null mutant transformed with AtNAP, OsNAP, or PvNAP. 18s rRNA serves as an internal standard of equal loading. FIG. 7(b) shows the phenotype of detached leaves of WT, null mutant, and various complementation lines. The leaves were kept in darkness for 4 days. FIG. 7(c) depicts the $F_v/F_m$ ratios of leaves shown in FIG. 7(b). FIG. 7(d) shows leaf senescence in intact plants of WT, null mutant, and various complementation lines. The plants were grown side by side in an *Arabidopsis* growth chamber.

FIG. 8(a) depicts the modified glucocorticoid-inducible gene expression system consisting of pTA7001 and pGL1167. pTA7001 provides the recombinant transcription factor GVG (GAL4 binding domain +VP16 activation domain+GR or glucocorticoid receptor), and pGL1167 contains the GAL4 cis elements and the AtNAP coding region. FIG. 8(b) shows the phenotypes of WT and transgenic plants harboring different constructs. The picture was taken 4 days after treatment with 30 μDEX inducer. FIG. 8(c) depicts the $F_v/F_m$ ratios of leaves from different plants that were treated with or without DEX. FIG. 8(d) shows the RNA gel blot analysis of the expression of AtNAP, SAG12, SAG13, and RBCS in leaves of plants that were treated with or without DEX. C, no treatment control; D, DEX treatment.

FIGS. 9(a)-(d) show homologs of AtNAP in kidney bean (*Phaseolus vulgaris*) and rice (*Oryza sativa* japonica cultivar group) and their senescence-specific expression patterns. FIG. 9(a) shows a phylogenetic tree of NAP proteins from different plant species. FIG. 9(b) is an alignment of amino acid sequences of NAP proteins from *Arabidopsis*, kidney bean, and rice. FIG. 9(c) shows the expression of PvNAP in senescing leaves of kidney bean. FIG. 9(d) shows the expression of OsNAP in senescing leaves of rice. Y, young leaf, S, senescing leaf.

FIGS. 11(a)-(b) depict the RNAi constructs used for suppression of GmNAP (FIG. 11(a)) and ZmNAP (FIG. 11(b)).

FIGS. 12(a)-(b) illustrate the complementation of *Arabidopsis* atnap null plants with ZmNAP (maize) and GmNAP (soybean). FIG. 12(a) shows leaf senescence in intact plants of WT, atnap null mutant, and atnap null mutant transformed with ZmNAP, while FIG. 12(b) shows leaf senescence in intact plants of WT, atnap null mutant, and atnap null mutant transformed with GmNAP.

FIGS. 13(a)-(b) show the microarray analysis of expression profile of AtNAP. FIG. 13(a) shows the expression levels of AtNAP in different plant tissues. The highest value shown in "44 senescent leaf" is 21790±391. FIG. 13(b) illustrates the effect of various treatments on the AtNAP expression. Ratios of expression change (numbers in shaded squares) and expression levels after different treatments are presented. The highest value shown in "PCD: senescence" is 26597±1957. The data were extracted from the Genevestigator microarray database (Zimmermann et al., "GENEVESTIGATOR. *Arabidopsis* Microarray Database and Analysis Toolbox," *Plant Physiol* 136:2621-2632 (2004), which is hereby incorporated by reference in its entirety).

DETAILED DESCRIPTION OF THE INVENTION

Figure 2:
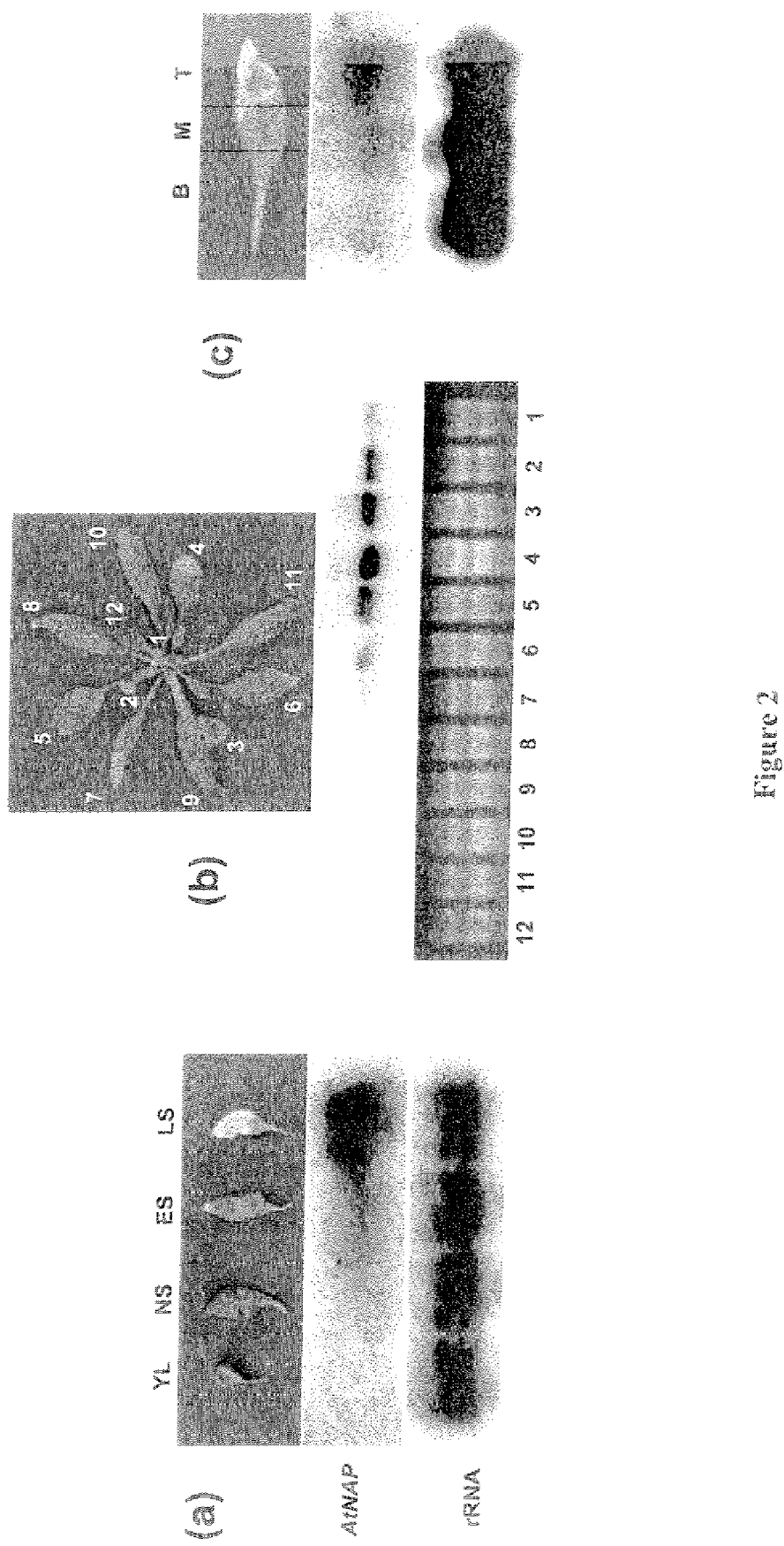
FIGS. 2(a)-(c) show RNA gel blot analysis of AtNAP expression during leaf senescence in *Arabidopsis*.
Figure 3:
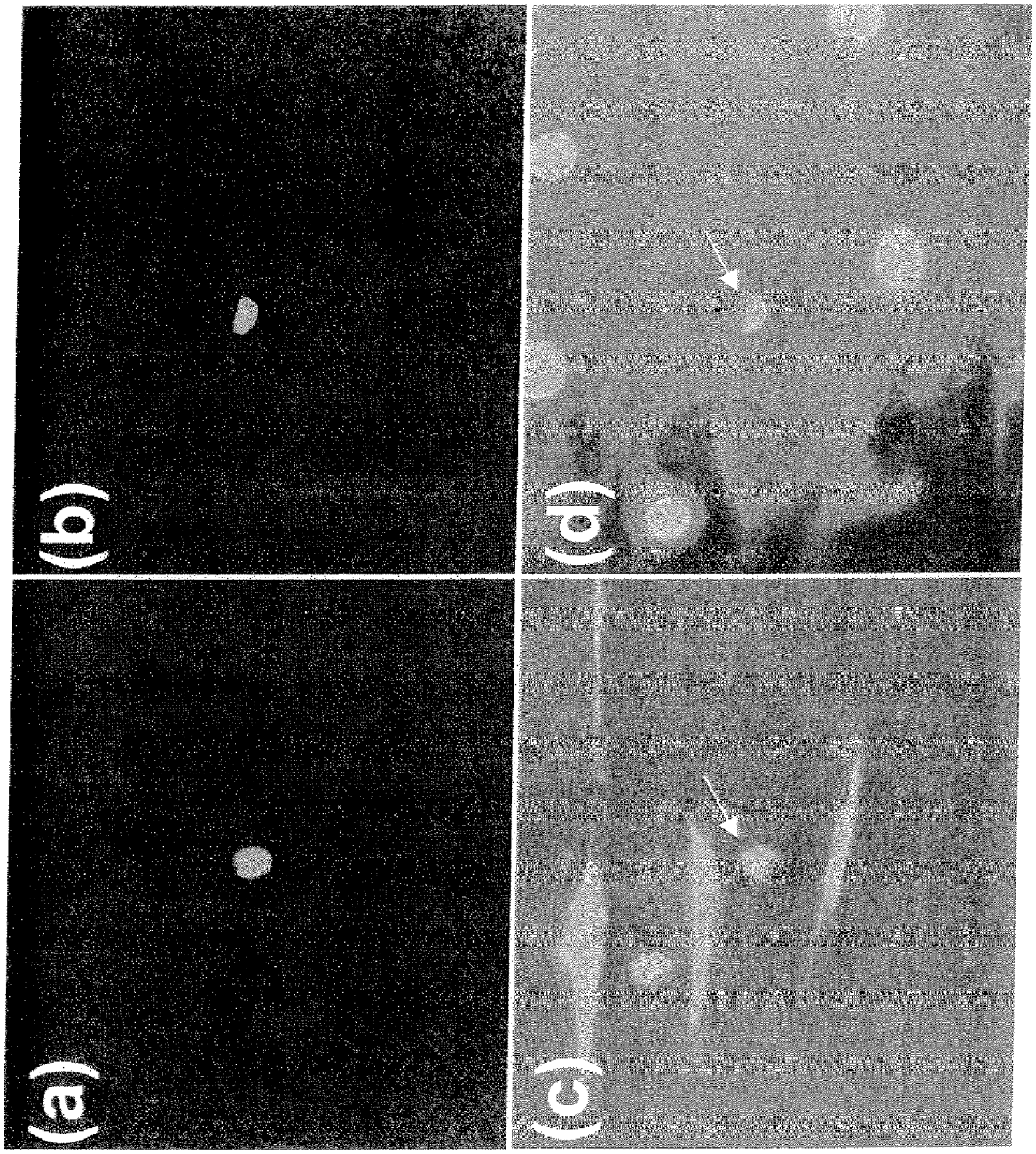
FIGS. 3(a)-(d) illustrate the nuclear localization of GFP-AtNAP fusion proteins.
Figure 5:
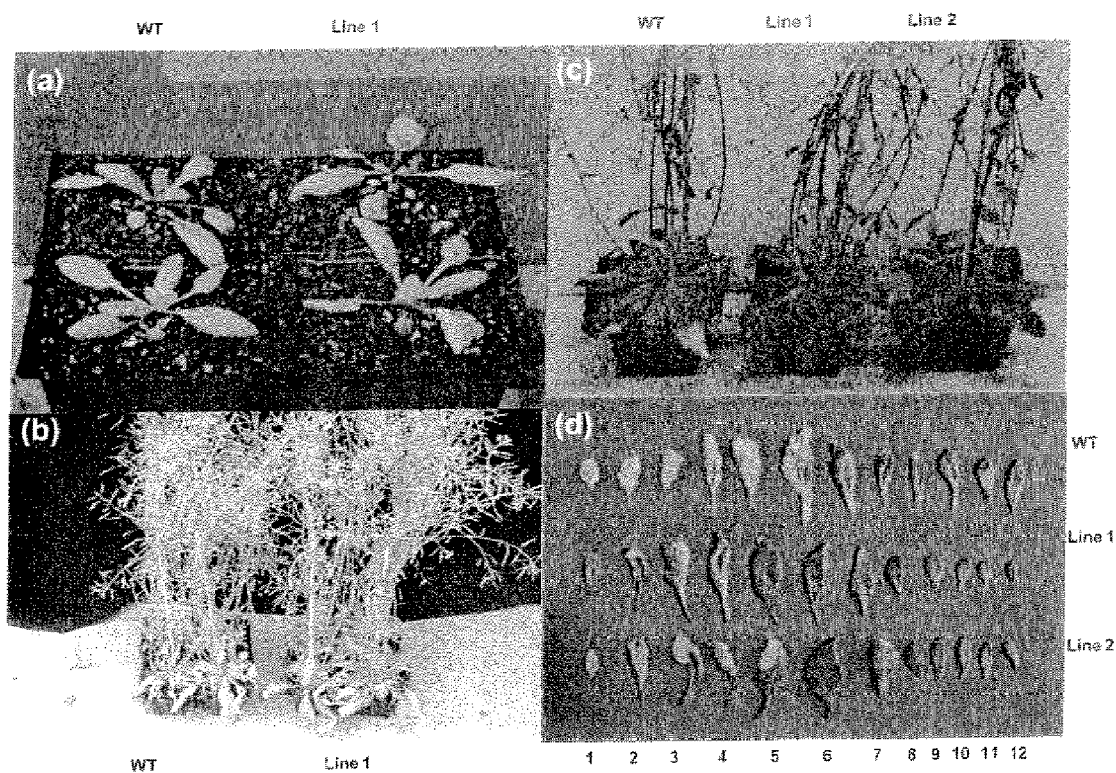
FIGS. 5(a)-(d) illustrate the delayed leaf senescence phenotype of the T-DNA insertion lines compared with that of age-matched wild-type (WT) plants.

The present invention relates to a transgenic plant having an altered level of NAP protein capable of causing leaf senescence in a plant, compared to that of a non-transgenic plant, where the transgenic plant displays an altered leaf senescence phenotype, relative to a non-transgenic plant.

In one embodiment of the present invention, the transgenic plant has a reduced level of NAP protein and displays a delayed leaf senescence phenotype. The plant can be transformed with a nucleic acid construct including a nucleic acid molecule configured to silence NAP protein expression.

In another embodiment (as described in more detail infra), the transgenic plant is transformed with a nucleic acid construct including a nucleic acid molecule that includes a dominant negative mutation and encodes a non-functional NAP protein. This construct is suitable in suppression or interference of endogenous mRNA encoding the NAP protein.

In another embodiment (as described in more detail infra), the transgenic plant is transformed with a nucleic acid construct including a nucleic acid molecule that is positioned in the nucleic acid construct to result in suppression or interference of endogenous mRNA encoding the NAP protein.

In another embodiment (as described in more detail infra), the transgenic plant is transformed with a nucleic acid construct including a nucleic acid molecule that encodes the NAP protein and is in sense orientation.

In still another embodiment (as described in more detail infra), the transgenic plant is transformed with a nucleic acid construct including a nucleic acid molecule that is an antisense form of a NAP protein encoding nucleic acid molecule.

In still another embodiment (as described in more detail infra), the transgenic plant is transformed with first and second of the nucleic acid constructs with the first nucleic acid construct encoding the NAP protein in sense orientation and the second nucleic acid construct encoding the NAP protein in antisense form.

In yet another embodiment (as described in more detail infra), the transgenic plant is transformed with a nucleic acid construct including a nucleic acid molecule including a first segment encoding the NAP protein, a second segment in an antisense form of a NAP protein encoding nucleic acid molecule, and a third segment linking the first and second segments.

In another embodiment of the present invention, the transgenic plant has an increased level of NAP protein and displays a premature or precocious leaf senescence phenotype. The plant can be transformed with a nucleic acid construct configured to overexpress NAP protein. In another embodiment (as described in more detail infra), the nucleic acid construct can include a plant specific promoter, such as an inducible plant promoter. The present invention further relates to seeds produced from the transgenic plant of the present invention.

Another aspect of the present invention relates to a mutant plant comprising an inactivated NAP gene, where the mutant plant displays a delayed leaf senescence phenotype, relative to a non-mutant plant. The present invention further relates to mutant plant seeds produced by growing the mutant plant of the present invention under conditions effective to cause the mutant plant to produce seed.

The transgenic plants and mutant plants of the present invention can be any plant with a NAP gene, including crop plants and ornamental plants. Suitable crop plants include, but are not limited to, alfalfa, rice, wheat, barley, rye, cotton, sunflower, peanut, corn, potato, sweet potato, kidney bean, pea, chicory, lettuce, endive, cabbage, bok choy, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, peach, strawberry, grape, raspberry, pineapple, soybean, *Medicago*, tobacco, tomato, sorghum, and sugarcane.

Suitable ornamental plants include, but are not limited to, *Arabidopsis thaliana, Saintpaulia, Populus*, petunia, pelargonium, poinsettia, chrysanthemum, carnation, zinnia, turfgrass, lily, and nightshade.

The present invention also relates to a method for delaying leaf senescence in a plant. The method involves providing a transgenic plant or plant seed transformed with a nucleic acid construct effective in silencing expression of a NAP protein capable of causing leaf senescence in a plant. Then, the transgenic plant or the plant grown from the transgenic plant seed is grown under conditions effective to delay leaf senescence in the transgenic plant or the plant grown from the transgenic plant seed. Leaf senescence can be delayed in the plant either before or after harvest.

In one embodiment, the above step of providing includes providing a nucleic acid construct having a nucleic acid molecule configured to silence NAP protein expression. The construct also includes a 5' DNA promoter sequence and a 3' terminator sequence. The nucleic acid molecule, the promoter, and the terminator are operatively coupled to permit expression of the nucleic acid molecule. A plant cell is then transformed with the nucleic acid construct. The method can further involve propagating plants from the transformed plant cell. Suitable methods for transforming the plant can include, for example, *Agrobacterium*-mediated transformation, vacuum infiltration, biolistic transformation, electroporation, micro-injection, chemical-mediated transformation (e.g., polyethylene-mediated transformation), and/or laser-beam transformation. The various aspects of this method are described in more detail infra.

In one aspect of the present invention, the nucleic acid construct results in suppression or interference of NAP protein expression by the nucleic acid molecule of the construct containing a dominant negative mutation and encoding a non-functional NAP protein.

In another aspect of the present invention, the nucleic acid construct results in interference of NAP protein expression by sense or co-suppression in which the nucleic acid molecule of the construct is in a sense (5'→3') orientation. Co-suppression has been observed and reported in many plant species and may be subject to a transgene dosage effect or, in another model, an interaction of endogenous and transgene transcripts that results in aberrant mRNAs (Senior, "Uses of Plant Gene Silencing," *Biotechnology and Genetic Engineering Reviews* 15:79-119 (1998); Waterhouse et al., "Exploring Plant Genomes by RNA-Induced Gene Silencing," *Nature Review: Genetics* 4:29-38 (2003), which are hereby incorporated by reference in their entirety). A construct with the nucleic acid molecule in the sense orientation may also give sequence specificity to RNA silencing when inserted into a vector along with a construct of both sense and antisense nucleic acid orientations as described infra (Wesley et al., "Construct Design for Efficient, Effective and High-Throughput Gene Silencing in Plants," *Plant Journal* 27(6) 581-590 (2001), which is hereby incorporated by reference in its entirety).

In another embodiment of the present invention, the nucleic acid construct results in interference of NAP protein expression by the use of antisense suppression in which the nucleic acid molecule of the construct is an antisense (3'→5') orientation. The use of antisense RNA to down-regulate the expression of specific plant genes is well known (van der Krol et al., *Nature,* 333:866-869 (1988) and Smith et al., *Nature,* 334:724-726 (1988), which are hereby incorporated by reference in their entirety). Antisense nucleic acids are DNA or RNA molecules that are complementary to at least a portion of a specific mRNA molecule (Weintraub, "Antisense RNA and DNA," *Scientific American* 262:40 (1990), which is hereby incorporated by reference in its entirety). In the target cell, the antisense nucleic acids hybridize to a target nucleic acid and interfere with transcription, and/or RNA processing, transport, translation, and/or stability. The overall effect of such interference with the target nucleic acid function is the disruption of protein expression (Baulcombe, "Mechanisms of Pathogen-Derived Resistance to Viruses in Transgenic Plants," *Plant Cell* 8:1833-44 (1996); Dougherty, et al., "Transgenes and Gene Suppression: Telling us Something New?," *Current Opinion in Cell Biology* 7:399-05 (1995); Lomonossoff, "Pathogen-Derived Resistance to Plant Viruses," *Ann. Rev. Phytopathol.* 33:323-43 (1995), which are hereby incorporated by reference in their entirety). Accordingly, one aspect of the present invention involves a nucleic acid construct which contains the NAP protein encoding nucleic acid molecule being inserted into the construct in antisense orientation.

Interference of NAP protein expression is also achieved in the present invention by the generation of double-stranded RNA ("dsRNA") through the use of inverted-repeats, segments of gene-specific sequences oriented in both sense and antisense orientations. In one embodiment of this aspect of the present invention, sequences in the sense and antisense orientations are linked by a third segment, and inserted into a suitable expression vector having the appropriate 5' and 3' regulatory nucleotide sequences operably linked for transcription. The expression vector having the modified nucleic acid molecule is then inserted into a suitable host cell or subject. In the present invention, the third segment linking the two segments of sense and antisense orientation may be any nucleotide sequence such as a fragment of the β-glucuronidase ("GUS") gene. In another embodiment of this aspect of the present invention, a functional (splicing) intron of the NAP gene may be used for the third (linking) segment, or, in yet another aspect of the present invention, other nucleotide sequences without complementary components in the NAP gene may be used to link the two segments of sense and antisense orientation (Chuang et al., "Specific and Heritable Genetic Interference by Double-Stranded RNA in *Arabidopsis thaliana*," *Proc. Nat'l Academy of Sciences USA* 97(9): 4985-4990 (2000); Smith et al., "Total Silencing by Intron-Spliced Hairpin RNAs," *Nature* 407:319-320 (2000); Waterhouse et al., "Exploring Plant Genomes by RNA-Induced Gene Silencing," *Nature Review: Genetics* 4:29-38 (2003); Wesley et al., "Construct Design for Efficient, Effective and High-Throughput Gene Silencing in Plants," *Plant Journal* 27(6):581-590 (2001), which are hereby incorporated by reference in their entirety). In any of the embodiments with inverted repeats of NAP protein, the sense and antisense segments may be oriented either head-to-head or tail-to-tail in the construct.

Another aspect of the present invention involves using hairpin RNA ("hpRNA") which may also be characterized as dsRNA. This involves RNA hybridizing with itself to form a hairpin structure that comprises a single-stranded loop region and a base-paired stem. Though a linker may be used between the inverted repeat segments of sense and antisense sequences to generate hairpin or double-stranded RNA, the use of intron-free hpRNA can also be used to achieve silencing of NAP protein expression.

Alternatively, in another aspect of the present invention, a plant may be transformed with constructs encoding both sense and antisense orientation molecules having separate promoters and no third segment linking the sense and antisense sequences (Chuang et al., "Specific and Heritable Genetic Interference by Double-Stranded RNA in *Arabidopsis thaliana*," *Proc. Nat'l Academy of Sciences USA* 97(9): 4985-4990 (2000); Waterhouse et al., "Exploring Plant Genomes by RNA-Induced Gene Silencing," *Nature Review: Genetics* 4:29-38 (2003); Wesley et al., "Construct Design for Efficient, Effective and High-Throughput Gene Silencing in Plants," *Plant Journal* 27(6):581-590 (2001), which are hereby incorporated by reference in their entirety).

The NAP nucleotide sequences used in the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pG-Cha, p35S-Cha, pBR322, pBR325, pACYC177, pACYC1084, pUC8, pUC9, pUC18, pUC19, pLG339, pR290, pKC37, pKC11, SV 40, pBluescript II SK+/– or KS+/– (see "Stratagene Cloning Systems" Catalog (1993) from Stratagene, La Jolla, Calif., which is hereby incorporated by reference in its entirety), pQE, pIH821, pGEX, pET series (see Studier et. al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor, N.Y.:Cold Spring Harbor Press (1989), and Ausubel et al., *Current Protocols in Molecular Biology*, New York, N.Y.:John Wiley & Sons (1989), which are hereby incorporated by reference in their entirety.

In preparing a nucleic acid construct for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soil-borne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.*

12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Molec. Biol.* 27:405-409 (1995), which is hereby incorporated by reference in its entirety). Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. Tissue-specific and organ-specific promoters can also be used.

A constitutive promoter is a promoter that directs expression of a gene throughout the development and life of an organism. Examples of some constitutive promoters that are widely used for inducing expression of transgenes include the nopaline synthase (NOS) gene promoter, from *Agrobacterium tumefaciens* (U.S. Pat. No. 5,034,322 to Rogers et al., which is hereby incorporated by reference in its entirety), the cauliflower mosaic virus (CaMV) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11:605-612 (1997); McNellis et al., "Glucocorticoid-Inducible Expression of a Bacterial Avirulence Gene in Transgenic *Arabidopsis* Induces Hypersensitive Cell Death, *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific or developmentally regulated promoters include seed, flower, fruit, or root specific promoters as are well known in the field (U.S. Pat. No. 5,750,385 to Shewmaker et al., which is hereby incorporated by reference in its entirety).

A number of tissue- and organ-specific promoters have been developed for use in genetic engineering of plants (Potenza et al., "Targeting Transgene Expression in Research, Agricultural, and Environmental Applications: Promoters used in Plant Transformation," *In Vitro Cell. Dev. Biol. Plant* 40:1-22 (2004), which is hereby incorporated by reference in its entirety). Examples of such promoters include those that are floral-specific (Annadana et al., "Cloning of the Chrysanthemum UEP1 Promoter and Comparative Expression in Florets and Leaves of *Dendranthema grandiflora*," *Transgenic Res.* 11:437-445 (2002), which is hereby incorporated by reference in its entirety), seed-specific (Kluth et al., "5' Deletion of a gbss1 Promoter Region Leads to Changes in Tissue and Developmental Specificities," *Plant Mol. Biol.* 49:669-682 (2002), which is hereby incorporated by reference in its entirety), root-specific (Yamamoto et al., "Characterization of cis-acting Sequences Regulating Root-Specific Gene Expression in Tobacco," *Plant Cell* 3:371-382 (1991), which is hereby incorporated by reference in its entirety), fruit-specific (Fraser et al., "Evaluation of Transgenic Tomato Plants Expressing an Additional Phytoene Synthase in a Fruit-Specific Manner," *Proc. Natl. Acad. Sci. USA* 99:1092-1097 (2002), which is hereby incorporated by reference in its entirety), and tuber/storage organ-specific (Visser et al., "Expression of a Chimaeric Granule-Bound Starch Synthase-GUS gene in transgenic Potato Plants," *Plant Mol. Biol.* 17:691-699 (1991), which is hereby incorporated by reference in its entirety). Targeted expression of an introduced gene (transgene) is necessary when expression of the transgene could have detrimental effects if expressed throughout the plant. On the other hand, silencing a gene throughout a plant could also have negative effects. However, this problem could be avoided by localizing the silencing to a region by a tissue-specific promoter.

The nucleic acid construct used in the present invention also includes an operable 3' regulatory region, selected from among those which are capable of providing correct transcription termination and polyadenylation of mRNA for expression in the host cell of choice, operably linked to a modified trait nucleic acid molecule of the present invention. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313 (6005):810-812 (1985), which is hereby incorporated by reference in its entirety). Virtually any 3' regulatory region known to be operable in plants would be suitable for use in conjunction with the present invention.

The different components described above can be ligated together to produce the expression systems which contain the nucleic acid constructs used in the present invention, using well known molecular cloning techniques as described in Sambrook et al., *Molecular Cloning: A Laboratory Manual*, Second Edition Cold Spring Harbor, N.Y.:Cold Spring Harbor Press (1989), and Ausubel et al. *Current Protocols in Molecular Biology*, New York, N.Y:John Wiley & Sons (1989), which are hereby incorporated by reference in their entirety.

Once the nucleic acid construct has been prepared, it is ready to be incorporated into a host cell. Basically, this method is carried out by transforming a host cell with the nucleic acid construct under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells are plant cells. Methods of transformation may result in transient or stable expression of the nucleic acid under control of the promoter. Preferably, the nucleic acid construct of the present invention is stably inserted into the genome of the recombinant plant cell as a result of the transformation, although transient expression can serve an important purpose, particularly when the plant under investigation is slow-growing.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 µm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., *Proc. Natl. Acad. Sci. USA* 79:1859-63 (1982), which is hereby incorporated by reference in its entirety). The nucleic acid molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include chemical-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures*, Vol. 1, New York, N.Y.:MacMillan Publishing Co. (1983); Vasil, ed., *Cell Culture and Somatic Cell Genetics of Plants*, Vol. I (1984) and Vol. III (1986), Orlando:Acad. Press; and Fitch et al., "Somatic Embryogenesis and Plant Regeneration from Immature Zygotic Embryos of Papaya (*Carica papaya* L.)," *Plant Cell Rep.* 9:320 (1990), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the neomycin phosphotransferae II ("nptII") gene which confers kanamycin resistance (Fraley et al., *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, N.Y.:Cold Spring Harbor Press (1989), which is hereby incorporated by reference in its entirety).

After the fusion gene containing a nucleic acid construct is stably incorporated in transgenic plants, the transgene can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds are recovered from the transgenic plants. These seeds can then be planted in the soil and cultivated using conventional procedures to produce transgenic plants.

An example of NAP protein that is encoded by the nucleic acid molecule used in the present invention is a NAP protein from kidney bean having an amino acid sequence of SEQ ID NO: 1, as shown in FIG. 1. In addition, other examples of NAP proteins include NAP proteins from *Medicago*, soybean, *Populus*, nightshade, *Arabidopsis*, wheat, rice, maize, peach, tomato, petunia, and potato having amino acid sequences of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13, respectively, as shown in FIG. 1.

The method of the present invention can be utilized in conjunction with plant cells from a wide variety of plants, as described supra. The present invention also relates to plants produced by the method of the present invention, described supra.

Another aspect of the present invention relates to a method for delaying leaf senescence in a plant. The method involves transforming a plant cell with a nucleic acid molecule encoding a NAP protein capable of causing leaf senescence in a plant operably associated with a promoter to obtain a transformed plant cell, where expression of the nucleic acid molecule in the plant cell causes delayed leaf senescence by a form of post-transcriptional gene silencing. Then, a plant is regenerated from the transformed plant cell under conditions effective to delay leaf senescence in the plant.

In the aspect of the present invention in which delay of leaf senescence is desired, the method of interfering with endogenous NAP protein expression may involve an RNA-based form of gene-silencing known as RNA interference (RNAi) (also known more recently as siRNA for short, interfering RNAs). RNAi is a form of post-transcriptional gene silencing (PTGS). PTGS is the silencing of an endogenous gene caused by the introduction of a homologous double-stranded RNA (dsRNA), transgene, or virus. In PTGS, the transcript of the silenced gene is synthesized, but does not accumulate because it is degraded. RNAi is a specific from of PTGS, in which the gene silencing is induced by the direct introduction of dsRNA. Numerous reports have been published on critical advances in the understanding of the biochemistry and genetics of both gene silencing and RNAi (Matzke et al., "RNA-Based Silencing Strategies in Plants," *Curr Opin Genet Dev* 11(2):221-227 (2001), Hammond et al., "Post-Transcriptional Gene Silencing by Double-Stranded RNA," *Nature Rev Gen* 2:110-119 (Abstract) (2001); Hamilton et al., "A Species of Small Antisense RNA in Posttranscriptional Gene Silencing in Plants," *Science* 286:950-952 (Abstract) (1999); Hammond et al., "An RNA-Directed Nuclease Mediates Post-Transcriptional Gene Silencing in *Drosophila* Cells," *Nature* 404:293-298 (2000); Hutvagner et al., "RNAi: Nature Abhors a Double-Strand," *Curr Opin Genetics & Development* 12:225-232 (2002), which are hereby incorporated by reference in their entirety). In iRNA, the introduction of double stranded RNA (dsRNA) into animal or plant cells leads to the destruction of the endogenous, homologous mRNA, phenocopying a null mutant for that specific gene. In siRNA, the dsRNA is processed to short interfering molecules of 21-, 22- or 23-nucleotide RNAs (siRNA), which are also called "guide RAs," (Hammond et al., "Post-Transcriptional Gene Silencing by Double-Stranded RNA," *Nature Rev Gen* 2:110-119 (Abstract) (2001); Sharp, P. A., "RNA Interference-2001," *Genes Dev* 15:485-490 (2001); Hutvagner et al., "RNAi: Nature Abhors a Double-Strand," *Curr Opin Genetics & Development* 12:225-232 (2002), which are hereby incorporated by reference in their entirety) in vivo by the Dicer enzyme, a member of the RNAse III-family of dsRNA-specific ribonucleases (Hutvagner et al., "RNAi: Nature Abhors a Double-Strand," *Curr Opin Genetics & Development* 12:225-232 (2002); Bernstein et al., "Role for a Bidentate Ribonuclease in the Initiation Step of RNA Interference," *Nature* 409:363-366 (2001); Tuschl, T., "RNA Interference and Small Interfering RNAs," *Chembiochem* 2:239-245 (2001); Zamore et al., "RNAi: Double Stranded RNA Directs the ATP-Dependent Cleavage of mRNA at 21 to 23 Nucleotide Intervals," *Cell* 101:25-3 (2000); U.S. Pat. No. 6,737, 512 to Wu et al., which are hereby incorporated by reference in their entirety). Successive cleavage events degrade the RNA to 19-21 bp duplexes, each with 2-nucleotide 3' overhangs (Hutvagner et al., "RNAi: Nature Abhors a Double-Strand," *Curr Opin Genetics & Development* 12:225-232 (2002); Bernstein et al., "Role for a Bidentate Ribonuclease in the Initiation Step of RNA Interference," *Nature* 409:363-366 (2001), which are hereby incorporated by reference in their entirety). The siRNAs are incorporated into an effector known as the RNA-induced silencing complex (RISC), which targets the homologous endogenous transcript by base pairing interactions and cleaves the mRNA approximately 12 nucleotides form the 3' terminus of the siRNA (Hammond et al., "Post-Transcriptional Gene Silencing by Double-Stranded RNA," *Nature Rev Gen* 2:110-119 (Abstract) (2001); Sharp, P. A., "RNA Interference-2001," *Genes Dev* 15:485-490 (2001); Hutvagner et al., "RNAi: Nature Abhors a Double-Strand," *Curr Opin Genetics & Development* 12:225-232 (2002); Nykanen et al., "ATP Requirements and Small Interfering RNA Structure in the RNA Interference Pathway," *Cell* 107:309-321 (2001), which are hereby incorporated by reference in their entirety).

There are several methods for preparing siRNA, including chemical synthesis, in vitro transcription, siRNA expression vectors, and PCR expression cassettes. In one aspect of the present invention, dsRNA for the nucleic acid molecule used in the present invention can be generated by transcription in vivo. This involves modifying the nucleic acid molecule for the production of dsRNA, inserting the modified nucleic acid molecule into a suitable expression vector having the appropriate 5' and 3' regulatory nucleotide sequences operably linked for transcription and translation, as described supra, and introducing the expression vector having the modified nucleic acid molecule into a suitable host or subject. Using siRNA for gene silencing is a rapidly evolving tool in molecular biology, and guidelines are available in the literature for designing highly effective siRNA targets and making antisense nucleic acid constructs for inhibiting endogenous protein (U.S. Pat. No. 6,737,512 to Wu et al.; Brown et al., "RNA Interference in Mammalian Cell Culture: Design, Execution, and Analysis of the siRNA Effect," Ambion *TechNotes* 9(1): 3-5(2002); Sui et al., "A DNA Vector-Based RNAi Technology to Suppress Gene Expression in Mammalian Cells," *Proc Natl Acad Sci USA* 99(8):5515-5520 (2002); Yu et al., "RNA Interference by Expression of Short-Interfering RNAs and Hairpin RNAs in Mammalian Cells," *Proc Natl Acad Sci USA* 99(9):6047-6052 (2002); Paul et al., "Effective Expression of Small Interfering RNA in Human Cells," *Nature Biotechnology* 20:505-508 (2002); Brummelkamp et al., "A System for Stable Expression of Short Interfering RNAs in Mammalian Cells," *Science* 296:550-553 (2002), which are hereby incorporated by reference in their entirety). There are also commercially available sources for custom-made siRNAs.

The present invention also relates to a method of making a mutant plant having a decreased level of NAP protein compared to that of a non-mutant plant, where the mutant plant displays a delayed leaf senescence phenotype relative to a non-mutant plant. The method involves providing at least one cell of a non-mutant plant containing a gene encoding a functional NAP protein. Next, the at least one cell of a non-mutant plant is treated under conditions effective to inactivate the gene, thereby yielding at least one mutant plant cell containing an inactivated NAP gene. The at least one mutant plant cell is then propagated into a mutant plant, where the mutant plant has a decreased level of NAP protein compared to that of the non-mutant plant and displays a delayed leaf senescence phenotype relative to a non-mutant plant.

In other embodiments of this method of making a mutant plant, the functional NAP protein can be any NAP protein from a wide variety of plants as described herein supra.

In another embodiment of this method of making a mutant plant, the treating step involves subjecting the at least one cell of the non-mutant plant to a chemical mutagenizing agent under conditions effective to yield at least one mutant plant cell containing an inactive NAP gene. Suitable chemical mutagenizing agents can include, for example, ethylmethanesulfonate.

In another embodiment of this method of making a mutant plant, the treating step involves subjecting the at least one cell of the non-mutant plant to a radiation source under conditions effective to yield at least one mutant plant cell containing an inactive NAP gene. Suitable radiation sources can include, for example, sources that are effective in producing ultraviolet rays, gamma rays, or fast neutrons.

In another embodiment of this method of making a mutant plant, the treating step involves inserting an inactivating nucleic acid molecule into the gene encoding the functional NAP protein or its promoter under conditions effective to inactivate the gene. Suitable inactivating nucleic acid molecules can include, for example, a transposable element. Examples of such transposable elements include, but are not limited to, an Activator (Ac) transposon, a Dissociator (Ds) transposon, or a Mutator (Mu) transposon.

In yet another embodiment of this method of making a mutant plant, the treating step involves subjecting the at least one cell of the non-mutant plant to *Agrobacterium* transformation under conditions effective to insert an *Agrobacterium* T-DNA sequence into the gene, thereby inactivating the gene. Suitable *Agrobacterium* T-DNA sequences can include, for example, those sequences that are carried on a binary transformation vector of pAC106, pAC161, pGABI1, pADIS1, pCSA110, pDAP101, derivatives of pBIN19, or pCAMBIA plasmid series.

In still another aspect of this method of making a mutant plant, the treating step involves subjecting the at least one cell of the non-mutant plant to site-directed mutagenesis of the NAP gene or its promoter under conditions effective to yield at least one mutant plant cell containing an inactive NAP gene. The treating step can also involve mutagenesis by homologous recombination of the NAP gene or its promoter, targeted deletion of a portion of the NAP gene sequence or its promoter, and/or targeted insertion of a nucleic acid sequence into the NAP gene or its promoter. The various plants that can be used in this method are the same as those described supra with respect to the transgenic plants and mutant plants. Other embodiments of the present invention relate to mutant plants produced by this method, as well as mutant plant seeds produced by growing the mutant plant under conditions effective to cause the mutant plant to produce seed.

The present invention also relates to a method for causing precocious leaf senescence or promoting leaf senescence in a plant. The method involves transforming a plant cell with a nucleic acid molecule encoding a NAP protein capable of causing leaf senescence in a plant operably associated with a promoter to obtain a transformed plant cell. Next, a plant is regenerated from the transformed plant cell. Then, the promoter is induced under conditions effective to cause premature or precocious leaf senescence in the plant. The method of the present invention can be utilized in conjunction with plant cells from a wide variety of plants, as described supra. Preferably, this method is used to cause premature or precocious leaf senescence in cotton. The present invention also relates to plants produced by this method of the present invention.

Another aspect of the present invention relates to a method of identifying a candidate plant suitable for breeding that displays a delayed leaf senescence and/or enhanced yield phenotype. The method involves analyzing the candidate plant for the presence, in its genome, of an inactivated NAP gene. In one embodiment of the present invention, the method identifies a candidate plant suitable for breeding that displays a delayed leaf senescence phenotype. In another embodiment of the present invention, the method identifies a candidate plant suitable for breeding that displays an enhanced yield phenotype. In yet another embodiment of the present invention, the method identifies a candidate plant suitable for breeding that displays a delayed leaf senescence and enhanced yield phenotype. Because NAP gene promotes leaf senescence, if any breeding line contains a mutated NAP gene, this line will display significantly delayed leaf senescence and/or an enhanced yield phenotype. If this line is used as a parental line for breeding purposes, the NAP gene can be used as a molecular marker for selecting progenies that contain the non-functional NAP gene. Accordingly, the NAP gene can be used as a molecular marker for breeding agronomic crops with a delayed senescence and enhanced yield. Alternatively, the NAP gene can be used as a molecular marker for breeding vegetables and flowers with delayed senescence (that do not necessarily have any concerns regarding yield).

EXAMPLES

The following examples are provided to illustrate embodiments of the present invention but are by no means intended to limit its scope.

Example 1

Plant Materials and Growth Conditions

*Arabidopsis* plants were grown at 23° C. with 60% relative humidity under constant light (150 µmol m$^{-2}$s$^{-1}$ light from a mixture of fluorescent and incandescent bulbs). Seeds were sown on Petri dishes containing one-half strength of Murashige and Skoog salts, 0.8% (w/v) phytoagar (Sigma, St. Louis, Mo.), and appropriate antibiotics. After imbibition, the seeds were kept at 4° C. overnight. Two-week-old seedlings were transplanted to Cornell mix soils (3 parts peat moss: 2 parts vermiculite: 1 part perlite; Tower Road Green house, Cornell University, Ithaca, N.Y.).

*Arabidopsis thaliana* ecotype Columbia-0 was used. The T-DNA insertion lines, the inducible overexpression lines, and the complementation lines were grown side by side with wild-type and other control lines unless indicated otherwise.

Example 2

Isolation of T-DNA Insertions within AtNAP

Two *Arabidopsis* lines for T-DNA insertions in AtNAP, SALK_005010 (line 1) and SALK_004077 (line 2) were obtained from the Salk T-DNA collection (Alonso et al., "Genome-Wide Insertional Mutagenesis of *Arabidopsis Thaliana*," *Science* 301:653-657 (2003), which is hereby incorporated by reference in its entirety). A PCR-based method was used to identify homozygous mutant plants. Genomic DNA was prepared from a small piece of leaf using a modified CTAB method (Murray et al., "Rapid Isolation of High Molecular Weight Plant DNA," *Nucleic Acids Res* 8:4321-4325 (1980), which is hereby incorporated by reference in its entirety). Briefly, 50-100 mg fresh leaf tissue was ground in a 1.5-ml microcentrifuge tube with a Craftsman 9-inch drill press (Sears, Roebuck and Co., Hoffman Estates, Ill.). The powdered samples were incubated at 55° C. for 30 min after 500 µl 2× extraction buffer (0.7 M NaCl, 1% w/v CTAB, 50 mM Tris (pH 8.0), 10 mM EDTA, 1% beta-ME added fresh) was added. After incubation, 500 µl chloroform:isoamyl alcohol 24:1 was added and mixed, and the samples were centrifuged for 10 min at 13,000 g. The aqueous phase (approximately 500 µl) was transferred to a new microfuge tube and 500 µl isopropanol was added to precipitate genomic DNA. PCR was used to amplify the genomic DNAs. The PCR conditions were as follows: 35 cycles with each cycle consisting of 94° C. for 30 sec, 55° C. for 30 sec, and 72° C. for 1 min. T-DNA left border primer G1099 (5'-GCGTGGAC CGC TTGCTGCAACT-3'; SEQ ID NO: 14) and gene-specific primers G1027 (5'-ATCAT GGAAG TAACTTC CCAATC-3'; SEQ ID NO: 15) and G1028 (5'-TTCAGTTCTTC TCTCTGCTTC-3'; SEQ ID NO: 16) for line 1, G1273 (5'-GGCCATTTTCTACGCT ACCT-3'; SEQ ID NO: 17) and G1123 (5'-CTTCCATGGTTTTCAGA-CAATTTAG-3'; SEQ ID NO: 18) for line 2 were used in the PCR reactions.

Example 3

Plasmid Construction

The GFP-AtNAP expression plasmid pGL1185 was generated by cloning AtNAP coding region into pRTL2-S65TGFP (Lin et al., "*Arabidopsis* FHY3/FAR1 Gene Family and Distinct Roles of Its Members in Light Control of *Arabidopsis* Development," *Plant Physiol.* 136:4010-4022 (2004), which is hereby incorporated by reference in its entirety). The coding region without the stop codon was amplified via PCR using primers G1526 (5'-TA GTCGACAGTTCCTG TTCTATTAGATTG-3'; SEQ ID NO: 19; the underlined section is an engineered SalI site) and G1527 (5'-TATCATGAACTTAAACATCGCTTGACG-3'; SEQ ID NO: 20; the underlined section is an engineered BspHI site). Pfu polymerase (Stratagene, La Jolla, Calif.) was used and the PCR product was sequenced. The PCR product cut with SalI and BspHI was cloned into pRTL2-S65TGFP at XhoI and NcoI sites.

For inducible overexpression of AtNAP, the 320 bp fragment of 6×GAL4 UAS and 35S TATA region from pTA7001 (Aoyama et al., "A Glucocorticoid-Mediated Transcriptional Induction System in Transgenic Plants," *Plant J* 11:605-612 (1997), which is hereby incorporated by reference in its entirety) was cloned into a binary vector called pPZP211 (Hajdukiewicz et al., "The Small, Versatile pPZP Family of *Agrobacterium* Binary Vectors For Plant Transformation," *Plant Mol Biol* 25:989-994 (1994), which is hereby incorporated by reference in its entirety) to form pGL1152. The full length cDNA of AtNAP (907 bp, including 43 bp 5' UTR region and 57 bp 3' UTR region) was amplified with primers G1100 (5'-CACTAGTTCCTGTTCTATTAGATTG-3'; SEQ ID NO: 21; the underlined section is an engineered SpeI site) and G1101 (5'-GCTGCAGTAACTTTTCAAGCACATC-3'; SEQ ID NO: 22; the underlined section is an engineered PstI site) using Pfu polymerase. The PCR product, after an A-tailing procedure described by the manufacturer (Promega, Madison, Wis.), was cloned into the pGEM-T vector (Promega) to form pGL1165. The plasmid was then sequenced. pGL1165 was digested with SpeI and PstI and the released AtNAP coding region was subcloned into pGL1152, resulting in pGL1167.

For the complementation test involving the *Arabidopsis* wild-type AtNAP, a 3166-bp genomic DNA containing the promoter (1961 bp) and coding region (1205 bp) of AtNAP was PCR amplified with primers G1628 (5'-GCGTCATC TCATCCTAATCCTCAT-3'; SEQ ID NO: 23) and G1629 (5'-CGTGACTTCGTCT TATCATGCTG-3'; SEQ ID NO: 24) using Pfu polymerase, and cloned into pGEM-T after A-tailing, to form pGL1186 that was subsequently sequenced. pGL1186 was digested with SacII, followed by treatment with T4 DNA polymerase (NEB, Beverly, Mass.) to remove the 3' overhangs to form blunt ends. The plasmid was further digested with SacI and the released AtNAP was cloned into the binary vector pPZP221 (Hajdukiewicz et al., "The Small, Versatile pPZP Family of *Agrobacterium* Binary Vectors For Plant Transformation," *Plant Mol Biol* 25:989-994 (1994), which is hereby incorporated by reference in its entirety) at the SacI and SmaI sites. The construct was named pGL1199.

When using the rice (*Oryza sativa*, japonica cultivar group) homolog of AtNAP (Os NAP) for complementation, primers G1807 (5'-TTCTGCAGCGTCAT CTCATCCTAATCCT-CAT-3'; SEQ ID NO: 25; the underlined section is an engineered PstI site) and G1808 (5'-GTTACTT CCATGGTTTTCAGACAATTTAG-3'; SEQ ID NO: 26; the underlined section is an engineered NcoI site) were used to PCR amplify the AtNAP promoter region. After an A-tailing procedure, the 2 kb PCR product was cloned into pGEM-T to form pGL1193. Genomic fragment containing the coding region of OsNAP (NP_912423) was PCR amplified using primers G1805 (5'-TTCCATGGTTCTGTCGAACCCG-3';

SEQ ID NO: 27; the underlined section is an engineered NcoI site) and G1666 (5'-GATCTAGACGAAGAACGAGC-TATCA G-3'; SEQ ID NO: 28). The 1.8 kb PCR product was cloned into pGEM-T to form pGL1191. The plasmids were sequenced. OsNAP released from pGL1191 upon NcoI digestion was then cloned into pGL1193 to form pGL1195. The 3.8 kb chimeric gene was then released from pGL1195 after digestion with SacI and ApaI (3' overhangs removed by T4 DNA polymerase treatment) and cloned into pZP221 at SacI and SmaI to form pGL1197. A nos terminator was added to the end of the chimeric gene in pGL1197 at the XbaI site to form pGL1800.

For complementation test involving the kidney bean (Phaseolus vulgaris) NAP homolog (PvNAP), primers G1807 (see above) and G1809 (5'-AA GTCGACGATTTTCAGACAATTTAGAAAACAATC-3'; SEQ ID NO: 29; the underlined section is an engineered SalI site) were used to PCR amplify the AtNAP promoter region. The 2 kb PCR product was cloned into pGEM-T to form pGL1194. The genomic fragment containing the coding region of PvNAP (AAK84884) was PCR amplified using primers G1806 (5'-AA GTCGACATGGATGCTACCACACCC TC-3'; SEQ ID NO: 30; the underlined section is an engineered SalI site) and G1668 (5'-GATCTAGATGGACGAAGCTTATCGTC-3'; SEQ ID NO: 31). The 1.3 kb PCR product was cloned into pGEM-T to form pGL1190. The plasmids were sequenced for sequence confirmation. The PvNAP coding region released from pGL1190 by SalI was then cloned into pGL1194 to form pGL1196. The 3.1 kb chimeric gene was released from pGL1196 by PstI and cloned into pPZP221, forming pGL1198. A nos terminator was added to the end of the chimeric gene in pGL1198 at the XbaI site to form pGL1801.

Example 4

*Agrobacterium* and Plant Transformation

The above constructs in binary vectors (pGL1167, pGL1199, pGL1800 and pGL1801) were transferred into *Agrobacterium tumefaciens* strain ABI as previously described in He et al., "A Gene Encoding an Acyl Hydrolase is Involved in Leaf Senescence in *Arabidopsis*," *Plant Cell* 14:805-815 (2002), which is hereby incorporated by reference in its entirety. Similarly, pTA7001 was transferred into *A. tumefaciens* strain LBA4404. The *Agrobacterium* cells containing the respective constructs were then used to transform *Arabidopsis* ecotype Columbia-0 or the atnap null mutant plants via vacuum infiltration (Bechtold et al., "In Planta *Agrobacterium*-Mediated Gene Transfer by Infiltration of Adult *Arabidopsis* Plants," *C. R. Acad. Sci. Paris* 316:1194-1199 (1993), which is hereby incorporated by reference in its entirety). Transgenic plants were selected on plates containing 50 mg/l kanamycin (for pGL1167 transformants), 80 mg/l gentamycin (PGL1199, pGL1800 and pGL1801 transformants) or 25 mg/l hygromycin (pTA7001 transformants). *Arabidopsis* plants harboring pGL1167 were crossed with plants harboring pTA7001 and the hybrids were selected on plates containing both kanamycin (50 mg/l) and hygromycin (25 mg/l).

Example 5

RNA Gel Blot and RT-PCR Analyses

Total RNA extraction from *Arabidopsis* leaves and RNA gel blot analysis were performed as described in He et al., "A Gene Encoding an Acyl Hydrolase is Involved in Leaf Senescence in *Arabidopsis*," *Plant Cell* 14:805-815 (2002), which is hereby incorporated by reference in its entirety. The hybridization was performed at 65° C. The Ambion RetroScript Kit (Ambion, Austin, Tex.) was used to perform RT-PCR analysis according the manufacturer's instruction. The Quantum-RNA™ Universal 18S Internal Standard Kit (Ambion) was used for equal loading control. DNA fragments for making related hybridization probes were PCR amplified using the following primers: G1027 and G1028 (see above) for AtNAP, G10 (5'-CAGCTGC GGATGTTGTTG-3'; SEQ ID NO: 32) and G246 (5'-CCACTTTCT CCCCATTTTG-3'; SEQ ID NO: 33) for SAG12, G9(5'-GCAACCAAAGGAGCCA TG-3'; SEQ ID NO: 34) and G16 (5'-GTTTGGCCAAC-TAGTCTGC-3'; SEQ ID NO: 35) for SAG13, G1148 (5'-AG TAATGGCTTCCTCTATGC-3'; SEQ ID NO: 36) and G1149 (5'-GGCTTGTAGGCAATGAAACT-3'; SEQ ID NO: 37) for RuBISCO small subunit gene RBCS, G1665 (5'-ATCCCT-TCCATTTCCG AC-3'; SEQ ID NO: 38) and G1666 (see above) for OsNAP, G1667 (5'-CTGGGTCTTGTG CAGAAT-3'; SEQ ID NO: 39) and G1668 (see above) for PvNAP. Some of the primers were also used for related RT-PCR analysis.

Example 6

Transient Gene Expression in Onion Epidermal Cells

Onion (*Allium cepa*) epidermal cells were transfected with pGL1185 using helium biolistic gun transformation system (Bio-Rad, Hercules, CA) as described in Lin et al., "*Arabidopsis* FHY3/FAR1 Gene Family and Distinct Roles of Its Members in Light Control of *Arabidopsis* Development," *Plant Physiol.* 136:4010-4022 (2004), which is hereby incorporated by reference in its entirety, and incubated in light or darkness for 24-48 h at 22° C. The subcellular localization of GFP fusion proteins was visualized with a fluorescence microscope.

Example 7

Glucocorticoid Treatments

The glucocorticoid treatments were performed as described by Aoyama et al., "A Glucocorticoid-Mediated Transcriptional Induction System in Transgenic Plants," *Plant J* 11:605-612 (1997), which is hereby incorporated by reference in its entirety. Two-week-old plants grown in pots were sprayed with 30 μM dexamethasone (DEX). The plants were sprayed once a day for 2 days and incubated for two additional days. $F_v/F_m$ ratios of leaves of these plants were measured, and leaves were harvested for molecular analysis.

Example 8

Dark-Induced Leaf Senescence

Leaf number 6 from a 3-week-old *Arabidopsis* plant was excised and placed on moisturized filter papers in Petri dishes with adaxial side facing up. The plates were kept in darkness at 23° C. for 4 days.

Example 9

Measurements of Chlorophyll Content, Fluorescence, and Ion Leakage

Chlorophyll was extracted and quantitated as described previously in He et al., "A Gene Encoding an Acyl Hydrolase is Involved in Leaf Senescence in *Arabidopsis*," *Plant Cell* 14:805-815 (2002), which is hereby incorporated by reference in its entirety. Fluorescence in leaves was measured using a portable modulated chlorophyll fluorometer (model: OS1-FL) according to the manufacturer's instructions (Opti-Sciences, Tyngsboro, Mass.). The ratio of variable fluorescence to maximal fluorescence ($F_v/F_m$) of each leaf was quantified directly using the fluorometer's test mode 1. For ion leakage, leaves were immersed into deionized distilled water, shaken in a 25° C. water bath for 30 min, and the conductivity was measured using a digital conductivity meter (Fisher Scientific Traceable, Hampton, NH). Samples were boiled for 10 min and then monitored for conductivity. The percentage of the first measurement over the second measurement was used as the membrane leakage indicator.

Example 10

Data Mining from the Genevestigator Microarray Database

The "Gene Atlas" program of the microarray database Genevestigator (www.genevestigator.ethz.ch) was used to search expression levels of AtNAP (Atlg69490) in different plant tissues. The program "Response Viewer" was used to search expression change and expression levels of AtNAP under different treatments. To run both programs, chip type "ATH1:22k array" for "wild type only" were used. When running "Response Viewer", chips from all sources were selected in "ATH1:22k array" for "wild type only" chip type.

Example 11

Molecular Phylogenetic Analyses

The amino acid sequence of AtNAP was used to search different genomic databases including GenBank (http://www.ncb.nlm.nih.gov/BLAST/for soybean, kidney bean, rice, nightshade, wheat, peach, tomato, petunia, and potato), the TIGR plant genome databases (http://www.tigr.org/plant-Projects.shtml for maize and *Medicago*), and *Populus*DB (http://www.populus.db.umu.se/for *Populus*). The NAC family genes with highest sequence similarity with AtNAP from different plant species including kidney bean (*Phaseolus vulgaris*) (AAK84884), rice (*Oryza sativa*) (NP_912423), soybean (*Glycine max*) (AAY46121), nightshade (*Solanum demissum*) (AAU90314), *Medicago truncatula* (AC140030_19.1), *Populus trichocarpa* (gene model gw1.X.1066.1), wheat (*Triticum aestivum*) (AAU08785), maize (*Zea mays*) (AZM5_18141), peach (*Prunus persica*) (CAG28971), tomato (*Lycopersicon esculentum*) (AAU43923), potato (*Solanum tuberosum*) (AAU12055), and petunia (*Petunia×hybrida*) (AAM34773), were used for molecular phylogenetic analyses. The kidney bean and rice NAP homologs, which were further studied for their expression patterns and used to transfer atnap mutant in heterogeneous complementation tests, are referred to, in the present application, as PvNAP, and OsNAP, respectively. Predicted amino acid sequences of AtNAP homologs from different plant species were first aligned using the alignment program CLUSTALW (Chenna et al., "Multiple Sequence Alignment With the Clustal Series of Programs," *Nucleic Acids Res* 31:3497-3500 (2003), which is hereby incorporated by reference in its entirety) with the default parameter values (alignment algorithm: full; CPU mode: single; Kimura correction: off; output: aln1; output order: aligned; score type: percent; ignore gaps in alignment: off; Number of sequences: 13; FIG. 1). The alignments were then used to produce the phylogeny using the phylogenetic analysis program MEGA3.1 (Kumar et al., "MEGA3:Integrated Software for Molecular Evolutionary Genetics Analysis and Sequence Alignment," *Brief Bioinform* 5:150-163 (2004), which is hereby incorporated by reference in its entirety). Parameters used in this analysis were: data type: amino acid; analysis: phylogeny reconstruction; method: neighbor-jointing method; gaps/missing data: complete deletion; model: amino:Poisson correction; substitutions to include: all; pattern among lineages: same (homogeneous). The bootstrap values for nodes in the phylogenetic tree are from 1000 replications.

Example 12

AtNAP is Upregulated During Leaf Senescence in *Arabidopsis*

Digital expression profile analysis of the *Arabidopsis* leaf senescence dbEST and microarray analysis (Buchanan-Wollaston et al., "Comparative Transcriptome Analysis Reveals Significant Differences in Gene Expression and Signalling Pathways Between Developmental and Dark/Starvation-Induced Senescence in *Arabidopsis*," *The Plant Journal* 42:567-585 (2005), which is hereby incorporated by reference in its entirety) revealed that AtNAP is one of the most abundantly transcribed transcription factor genes in senescing leaves (Guo et al., "Transcriptome of *Arabidopsis* Leaf Senescence," *Plant Cell and Environment* 27:521-549 (2004), which is hereby incorporated by reference in its entirety). RNA gel blot analysis showed that the expression of AtNAP in rosette leaves of *Arabidopsis* was closely associated with the progression of leaf senescence (FIGS. 2(*a*)-(*c*)). When leaves from the same phyllotactical position (leaf number 6 from the bottom of the plant) were studied, RNA messenger (mRNA) of AtNAP was detected only when the leaves started senescing (2-3 weeks after emergence; FIG. 2(*a*)). Leaf senescence in *Arabidopsis* grown under non-stressful conditions was age-dependent and progressed sequentially from the oldest leaf (the first leaf at the bottom of a plant) to the top young leaves. As shown in FIG. 2(*b*), AtNAP transcript was detected in the old, senescing leaves, but not in the young, green leaves. In a given leaf, senescence started from the leaf tip and progressed toward leaf base (petiole). The yellow tip showed stronger AtNAP expression than the proximal part of a leaf (FIG. 2(*c*)).

Example 13

AtNAP is Targeted to Nuclei

Although AtNAP is predicted to be a nuclear protein by PredictNLS (Cokol et al., "Finding Nuclear Localization Signals," *EMBO Rep* 1:411-415 (2000), which is hereby incorporated by reference in its entirety) and PSORT (Nakai et al., "A Knowledge Base for Predicting Protein Localization Sites in Eukaryotic Cells," *Genomics* 14:897-911 (1992), which is hereby incorporated by reference in its entirety), it does not have any obvious nuclear localization signal. To determine the subcellular localization of AtNAP, a chimeric gene containing a GFP-AtNAP construct driven by the 35S promoter was transiently expressed in onion (Allium cepa) epidermal cells using particle bombardment. Subcellular localization of the GFP fusion protein was visualized with a fluorescence microscope. DAPI (4',6'-diamidino 2-phenylindole) staining of DNA revealed GFP-AtNAP protein localization in the nuclei, suggesting that AtNAP is a nuclear protein (FIGS. 3(a)-(d)).

Example 14

The AtNAP Expression is Knocked Out in One T-DNA Line and Knocked Down in Another Line The AtNAP gene consists of three exons and encodes a protein with 268 amino acids (FIG. 4(a)). Two Salk T-DNA lines (Columbia background) were obtained from the *Arabidopsis* Biological Resource Center (ABRC) at Ohio State University (Alonso et al., "Genome-Wide Insertional Mutagenesis of *Arabidopsis Thaliana*," *Science* 301:653-657 (2003), which is hereby incorporated by reference in its entirety). Line 1 (SALK_005010) has a T-DNA insertion in the second exon, and line 2 (SALK_004077) has a T-DNA insertion in the promoter region (at −227 from the translation start site; FIG. 4(a)). RNA gel blot analysis showed that the AtNAP transcript in senescent leaves of the homozygous line 1 was not detectable, while AtNAP transcript levels in senescent leaves of line 2 plants was reduced to 5% of that in age-matched wild-type leaves (FIG. 4(b)). This suggested that line 1 was an atnap null mutant, while line 2 was a knockdown line.

Example 15

Leaf Senescence is Significantly Delayed in the AtNAP Null Mutant Plants

To compare any phenotypic changes in growth and development among line 1 (the atnap null mutant), line 2 (the atnap knockdown mutant) and wild type (Columbia accession), these plants were grown side by side in an *Arabidopsis* growth chamber. There were no visible differences in growth and development, except for the significantly delayed leaf senescence phenotype in the atnap null plants, and the less significantly retarded leaf senescence phenotype in the atnap knockdown plants (FIGS. 5(a)-(d)).

The atnap null mutant plants were further characterized. As shown in the mortality curves in FIG. 6(a), leaves of the atnap null mutant plants senesced later than those of wild-type plants. Consistent with a delayed visible yellowing phenotype (FIGS. 5(a)-(d)), chlorophyll levels in individual rosette leaves of the null line were generally higher than in counterpart leaves of the age-matched wild-type plants (FIG. 6(b)). The $F_v/F_m$ ratios in individual leaves of the null line were also higher than in counterpart leaves of the age-matched wild-type plants (FIG. 6(c)). The $F_v/F_m$ ratio reflects the photochemical quantum efficiency of photosystem II, as well as the photoreduction efficiency of the primary electron-accepting plastoquinone of photosystem II. In contrast, ion leakage in individual leaves of the null plants was less than that in wild-type plants (FIG. 6(d)). Ion leakage is an indicator of intactness of plasma membrane. The plasma membrane of a senescing cell becomes fragile and leaky.

Figure 6:
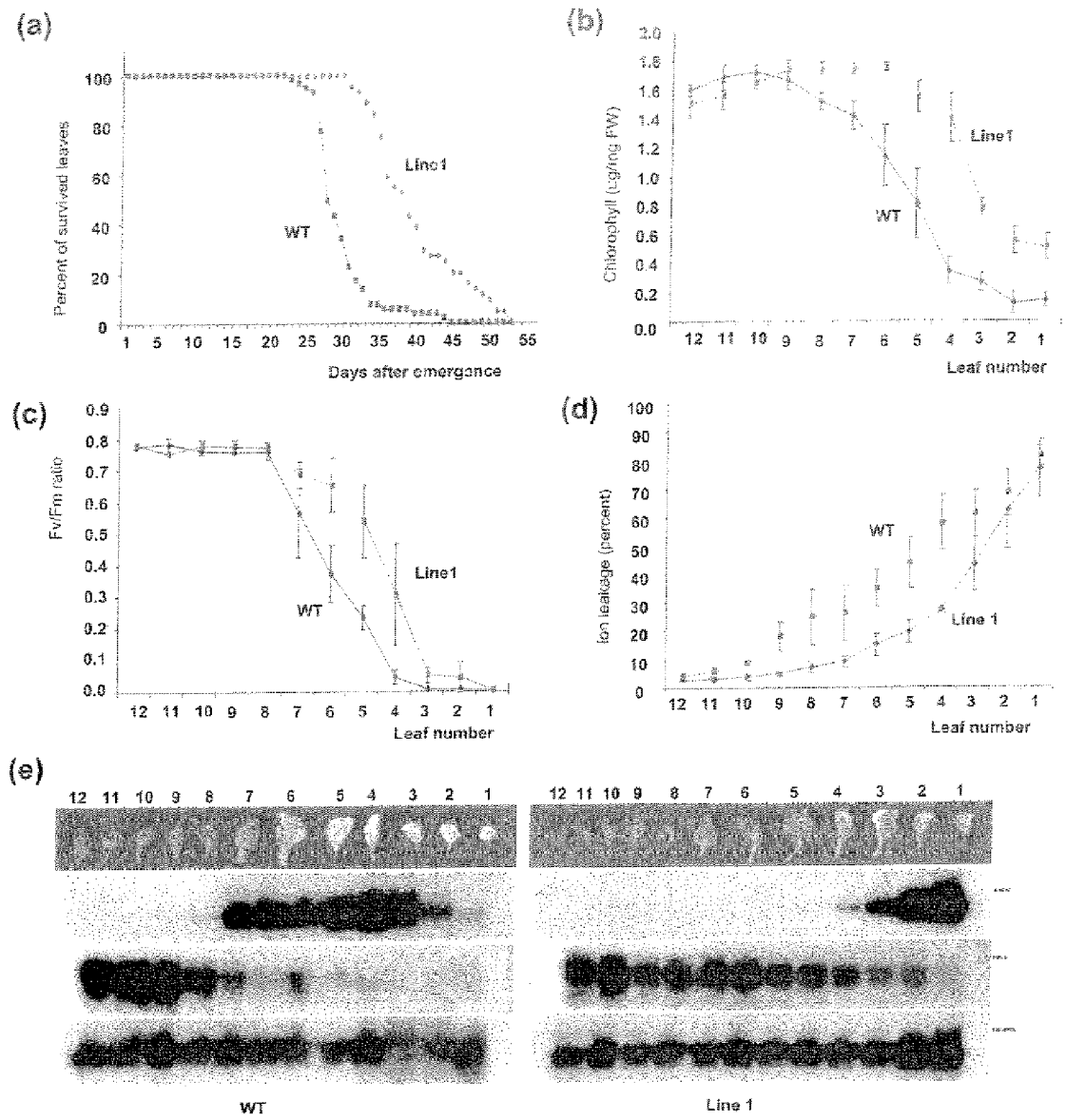
FIGS. 6(a)-(e) show the physiological and molecular analyses of atnap null mutant plants (line 1).

The expression of SAG12 and the Rubisco small subunit gene (RBCS) was also monitored. SAG12 is a highly senescence-specific gene in *Arabidopsis* and has been widely used as a molecular marker for leaf senescence, while RBCS is a typical senescence downregulated gene. As shown in FIG. 6(e), the expression of SAG12 was readily detectable in leaf number 7 of a 30-day-old wild-type plant, but it was barely detectable in leaf number 4 of an age-matched null plant.

All the data described above indicated that the leaf senescence process was dramatically delayed in the atnap mutant plants (approximately 10 days).

Example 16

AtNAP Restores the atnap Null Mutant Plants to Wild Type

Figure 7:
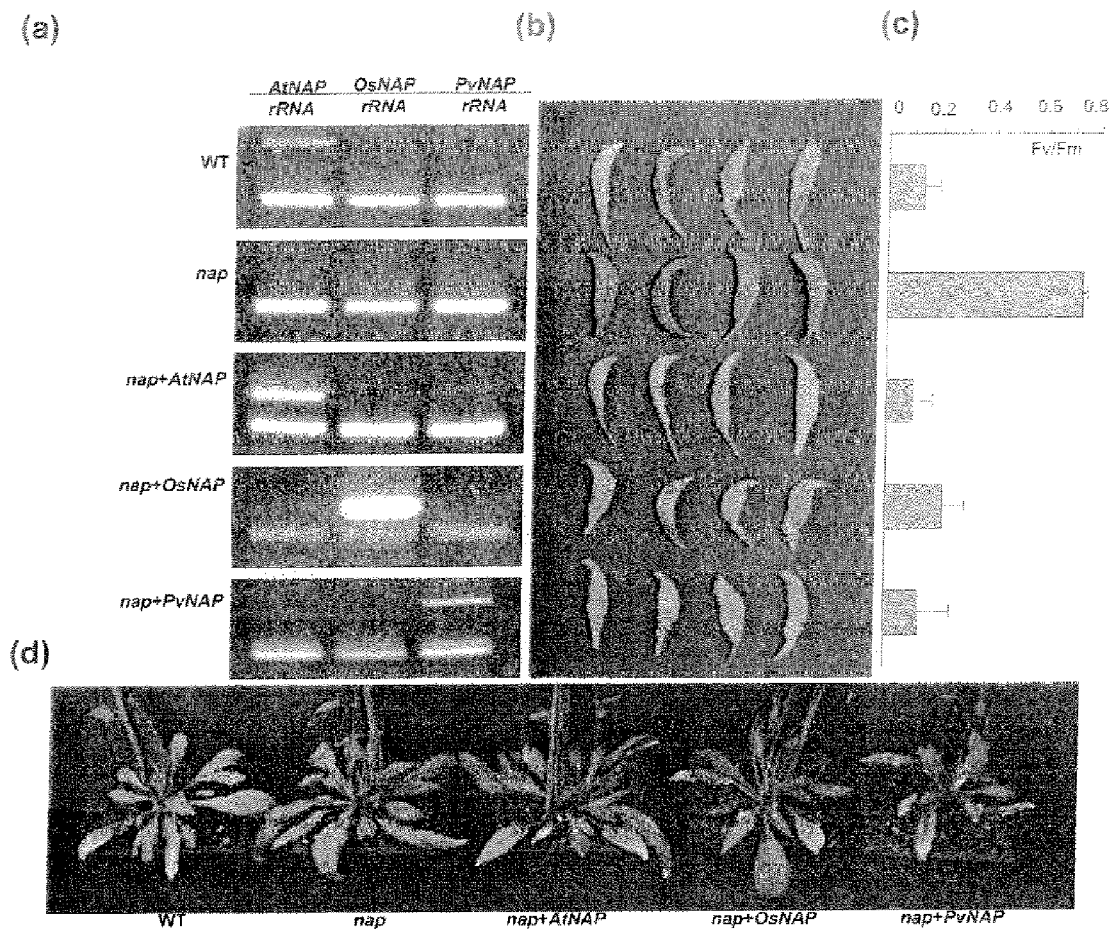
FIGS. 7(a)-(d) illustrate the complementation of *Arabidopsis* atnap null plants with AtNAP, OsNAP (rice), and PvNAP (kidney bean).

To confirm that the T-DNA insertional null mutation in AtNAP was responsible for the delayed senescence phenotype, a complementation test experiment was performed. The wild-type copy of AtNAP, including the 2 kb promoter region, was introduced into the atnap null mutant plants. The introduced AtNAP was expressed in senescing leaves (see "nap+ AtNAP" panel in FIG. 7(a)). The senescence phenotype in leaves that were either detached or in planta was characterized. The leaves detached from the AtNAP complemental lines senesced in the same manner as those leaves from wild type did, both phenotypically (FIG. 7(b)), and in terms of the $F_v/F_m$ ratio (FIG. 7(c)). In planta leaves of the complemental plants also senesced in the same manner as wild-type leaves (FIG. 7(d)). These data confirmed that loss of AtNAP expression in the atnap null mutant was the only cause of the delayed senescence phenotype.

Example 17

Inducible Overexpression of AtNAP Causes Precocious Senescence

Figure 8:
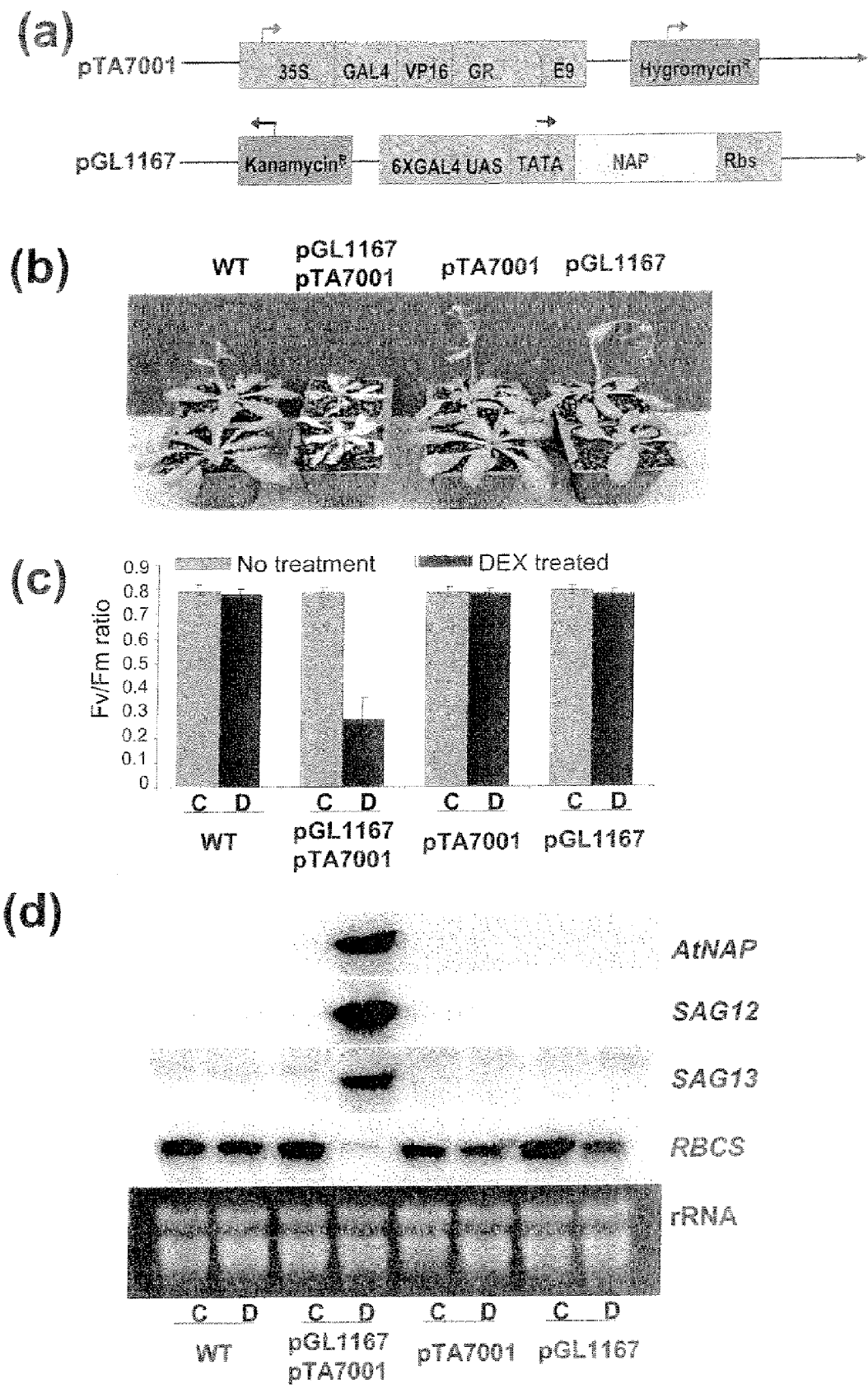
FIGS. 8(a)-(d) illustrate that inducible overexpression of AtNAP causes precocious senescence.

The role of AtNAP in leaf senescence was further investigated by performing gain-of-function analysis. Considering the fact that constitutive expression of this gene might be lethal, the chemical inducible gene expression system (Aoyama et al., "A Glucocorticoid-Mediated Transcriptional Induction System in Transgenic Plants," *Plant J* 11:605-612 (1997), which is hereby incorporated by reference in its entirety) was used. First, transgenic lines that harbored either the pTA7001 or pGL1167 constructs (FIG. 8(a)) were generated. pTA7001 contained the chimeric transcription factor GVG consisting of a DNA-binding domain of the yeast transcription factor GAL4, a transactivation domain of the herpes simplex virus transcriptional regulatory protein VP16 and a glucocorticoid receptor domain (FIG. 8(a)), while pGL1167 was a construct in which AtNAP is driven by a promoter containing six tandem copies of the GAL4 upstream activation sequence (FIG. 8(a)). Treatment with dexamethasone (DEX, a synthetic glucocorticoid) caused precocious leaf yellowing (FIG. 8(b)) and a significant reduction of the $F_v/F_m$ ratio (FIG. 8(c)) in F1 plants (pGL1167 homozygous plants× pTA7001 homozygous plants) but not in controls (wild type, plants containing pGL1167 or pTA7001 only). RNA blot analysis showed that AtNAP expression was strongly induced in the $F_1$ plants but not in the controls (FIG. 8(d)). The precocious leaf yellowing was a senescence process because SAG12 and SAG13 were both expressed (FIG. 8(d)). SAG12 and SAG13 are leaf senescence-specific marker genes. These data suggested that AtNAP was sufficient to promote leaf senescence.

Example 18

AtNAP Homologs in Rice and Kidney Bean are Specifically Expressed in Senescing Leaves The amino acid sequence of AtNAP was analyzed with the use of different genomic databases such as the GenBank (http://www.ncbi.nlm.nih.gov/BLAST/), the TIGR plant genome databases (http://www.tigr.org/plantProjects.shtml), and *Populus*DB (http://www.populus.db.umu.se/), and genes with high sequence similarity were identified from many different plant species (FIG. 9(*a*)). Among them are the NAC family transcription factor PvNAP (256 amino acids; AAK84884) from the dicot kidney bean (*Phaseolus vulgaris*) with 66% identity, and the NAC family transcription factor OsNAP (392 amino acids; NP_912423) from the monocot rice (*Oryza sativa*) with 70% identity (FIG. 9(*b*)). It was hypothesized that those homologs were functional orthologs of AtNAP. To test this hypothesis, it was first examined whether PvNAP and OsNAP shared the same leaf senescence-specific expression pattern as AtNAP. Kidney bean leaves at five distinct developmental stages, ranging from young leaves to entirely yellow leaves (FIG. 9(*c*)), were used for RNA gel blot analysis of PvNAP expression. As shown in FIG. 9(*c*), PvNAP transcript was detected in senescing leaves only. The expression of OsNAP was also shown to be senescence specific in rice leaves (FIG. 9(*d*)).

Example 19

AtNAP Homologs in Rice and Kidney Bean are Able to Restore the *Arabidopsis* atnap Null Mutant to Wild Type To further test the hypothesis that the homologs are functional orthologs of the *Arabidopsis* AtNAP, heterogeneous complementation tests were performed. The 2 kb AtNAP promoter was used to direct the expression of the coding region of OsNAP or PvNAP. These genes were expressed in senescent leaves of respective complementation lines (FIG. 7(*a*)). Phenotypically, fully expanded non-senescing leaves detached from wild-type plants became senescent after being incubated in darkness for 4 days. In contrast, age-matched leaves from atnap null mutant (line 1) remained green (FIG. 7(*b*)) and photosynthetically active (FIG. 7(*c*)). However, the leaves of the null plants complemented with OsNAP or PvNAP senesced like those of wild type (FIG. 7(*b*)). Similar observations were obtained when natural leaf senescence was examined in intact plants (FIG. 7(*d*)). Similarly to AtNAP, OsNAP and PvNAP were able to restore the *Arabidopsis* null mutant to wild type, which suggests that OsNAP and PvNAP are functional orthologs of AtNAP.

Example 20

RT-PCR Analysis of Soybean GmNAP and Maize ZmNAP During Leaf Senescence

Figure 10:
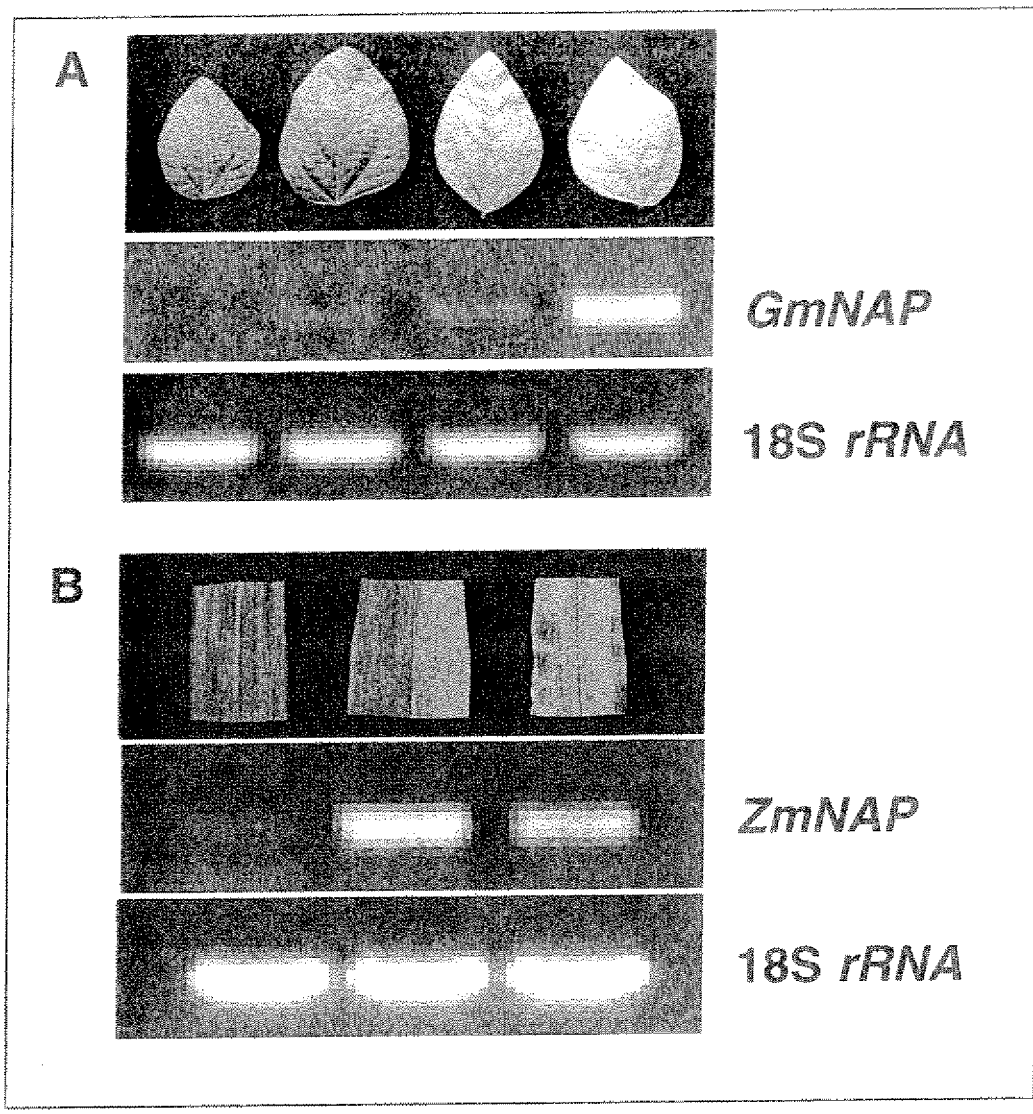
FIGS. 10(a)-(b) illustrate the RT-PCR analysis of the expression of soybean GmNAP (FIG. 10(a)) and maize ZmNAP (FIG. 10(b)) during leaf senescence. 18S rRNA was used as an internal standard for relative amount of total RNA that was used for each lane.

RT-PCR analysis of the expression of the AtNAP homologs in soybean (*Glycine max*) (AAY46121) (GmNAP) and maize (*Zea mays*) (AZM5_18141) (ZmNAP) was performed. As shown in FIGS. 10(*a*)-(*b*), both GmNAP and ZmNAP were upregulated during leaf senescence of soybean and maize, respectively.

Example 21

Use of RNA Interference to Suppress the AtNAP Homologs in Soybean (GmNAP) and Maize (ZmNAP)

The NAP gene is a master regulator that promotes leaf senescence. RNA interference (RNAi) approach was used to silence this gene in soybean and maize so that leaf senescence would be dramatically delayed. RNAi involves the use of double strand RNA (dsRNA) that can efficiently cause silencing of target gene and has, thus, been widely used in genetics. The dsRNA construct contains inverted repeats of a small fragment of the gene of interest, i.e., GmNAP or ZmNAP, so that, upon transcription, the RNA transcript will pair each other to form double strand between the inverted repeat sequences. The dsRNA triggers the cellular machinery to destroy any mRNA whose sequence matches with the repeat sequence. Therefore, RNAi constructs were prepared to suppress the expression of GmNAP and ZmNAP in soybean and maize, respectively, where the suppression of the homolog was expected to lead to the significant delay of leaf senescence in the respective crops.

For GmNAP RNAi, primers G2132 (5'-TCTAGAGGCAAAAGAGGA CTAC-3'; SEQ ID NO: 40; the underlined section is an engineered Xba I site) and G2133 (5'-GGATCCTGGTACTTCCCTGAATCT-3'; SEQ ID NO: 41; the underlined section is an engineered BamH I site) were used to PCR amplify a 271-bp fragment of the 3' end of GmNAP cDNA. The PCR product was cloned into pGEM-T (Promega, Madison, Wis.) to form plasmid pGL1818. pGL1818 was cut by Xba I after BamH I digestion and Klenow fill-in. The released GmNAP cDNA fragment was cloned into a binary vector pGL1100 at Xba I and Spe I (filled-in) sites, to form pGL1820. pGL1100 contains a 690-bp intron sequence of *Arabidopsis* AtWRKY75 between the 35S promoter and the RBS (Rubisco small subunit gene) terminator. Another copy of the GmNAP cDNA fragment released by Sac II and Xba I (filled-in) from pGL1818 was cloned into pGL1820 at Sac II and Hind III (filled-in) sites to form pGL1822 such that pGL1822 contains two copies of the 271-bp GmNAP cDNA in opposite orientation separated by the 690-bp intron. The 35S promoter-RNAi with intron-RBS terminator in pGL1822 was PCR amplified with primers G205 (5'-GGAATTCGCCCGGGGATCTCCTTTG-3'; SEQ ID NO: 45; the underlined section is an engineered EcoR I site) and G206 (5'-TAGGCCTTGATGCATGTTGTCAATC AATTG-3'; SEQ ID NO: 42; the underlined section is an engineered Stu I site). The PCR product was cut by EcoR I and Stu I and cloned into a binary vector at the EcoR I and Hind III (filled-in) sites, to form pGL1823 (FIG. 11(*a*)).

The above GmNAP RNAi silencing construct was used to transform soybean genotype Thome (Ohio State University) using the soybean cotyledonary-node *Agrobacterium*-mediated transformation system as described at the website (http://www.biotech.unl.edu/transgenic/protocols.html). Eighteen transgenic lines were generated.

For ZmNAP RNAi, primers G2136 (5'-TCTAGACGGAGCTGTTCA AC-3'; SEQ ID NO: 43; the underlined section is an engineered Xba I site) and G2137 (5'-AAGCTTAGAGTGAAGCGGCAT-3'; SEQ ID NO: 44; the underlined section is an engineered Hind III site) were used to PCR amplify a 410-bp fragment of the 3' end of ZmNAP cDNA. The PCR product was cloned into pGEM-T to form pGL1817. The plasmid of pGL1817 was cut by Xba I after Hind III digestion and Klenow fill-in. The released ZmNAP cDNA fragment was cloned into pGL1100 at Xba I and Spe I (filled-in) sites, to form pGL1819. Another copy of the ZmNAP cDNA fragment released by Sac II and Xba I (filled-in) from pGL1817 was cloned into pGL1819 at Sac II and Hind III (filled-in) sites to form pGL1821 such that pGL1821 contains two copies of the 410 bp ZmNAP cDNA in opposite orientation separated by the 690-bp intron sequence of *Arabidopsis* AtWRKY75 (FIG. 11(*b*)).

The above ZmNAP RNAi silencing construct was transferred into *Agrobacterium tumefaciens* strain ABI to prepare them for plant transformation.

Example 22

AtNAP Homologs in Maize and Soybean are Able to Restore the *Arabidopsis* atnap Null Mutant to Wild Type Using a similar strategy as described in Example 19 above, it was examined whether maize and soybean NAPs, i.e., ZmNAP and GmNAP, respectively, can complement the *Arabidopsis* atnap null mutant. The 2-kb AtNAP promoter was used to direct the expression of the coding region of ZmNAP or GmNAP. These genes were expressed in senescent leaves of respective complementation lines. Natural leaf senescence was examined in intact plants, where phenotypically leaves of wild-type plants became senescent (FIGS. 12(a)-(b)). In contrast, leaves of atnap null mutant remained green (FIGS. 12(a)-(b)). However, the leaves of the null plants complemented with ZmNAP or GmNAP senesced like those of wild type (FIGS. 12(a)-(b)). Therefore, ZmNAP and GmNAP were able to restore the *Arabidopsis* null mutant to wild type.

Leaf senescence limits crop yield and biomass accumulation. In soybean, insufficient phosphate (Pi) nutrient during soybean seed development promotes leaf senescence. When leaf senescence was significantly delayed (for eight days) by supplemental Pi via stem infusions, soybean grain yield was increased as much as 3-fold (Grabau et al., "P Nutrition During Seed Development: Leaf Senescence, Pod Retention, and Seed Weight of Soybean," *Plant Physiol.* 82:1008-1012 (1986), which is hereby incorporated by reference in its entirety). Both field and greenhouse experiments also proved that leaf senescence limits soybean yield by restricting the seed filling period (Hayati et al., "Carbon and Nitrogen Supply During Seed Filling and Leaf Senescence in Soybean," *Crop Sci.* 35:1063-1069 (1995), which is hereby incorporated by reference in its entirety).

The effect of delayed leaf senescence on yields has also been observed in maize and many other crops. For example, a retrospective analysis over 50 years (1930-1980) of hybrid maize data in US revealed that late onset of leaf senescence contributed to significant increases in maize yields (Duvick, "Genetic Contribution to Yield Gains of U.S. Hybrid Maize 1930-1980," in Fehr, ed., *Genetic Contributions to Yield Gains of Five Major Crop Plants*, vol. 7, Crop Science Society of America, Madison, Wis., pp. 15-47 (1984), which is hereby incorporated by reference in its entirety). Similar analysis of nearly 30 years (1959-1988) of maize hybrid yields in Ontario, Canada, also reached the same conclusion (Tollenaar, "Physiological-Basis of Genetic-Improvement of Maize Hybrids in Ontario from 1959 to 1988," *Crop Sci.* 31:119-124 (1991), which is hereby incorporated by reference in its entirety). Further physiological and genetic studies on the relationship between leaf senescence and maize yields have confirmed the correlation of delaying leaf senescence and yield enhancement (Valentinuz and Tollenaar, "Vertical Profile of Leaf Senescence During the Grain-Filling Period in Older and Newer Maize Hybrids," *Crop. Sci.* 44:827-835 (2004); Ougham et al., "The Genetic Control of Senescence Revealed by Mapping Quantitative Trait Loci," in Gan, ed., *Senescence Processes in Plants*, Blackwell Publishing, pp. 171-201 (2007), which are hereby incorporated by reference in their entirety).

Example 23

Use of NAP Gene to Manipulate Leaf Senescence in Crops

Various molecular, genetic and genomic strategies have been used to isolate genes that are differentially expressed during senescence, and as a result, thousands of SAGs have been identified. The structure and function of most SAGs have been predicted bioinformatically. There are only a few of those genes whose enzymatic activities have been shown biochemically, including several RNases (Lers et al., "Senescence-Induced RNases in Tomato," *Plant Molecular Biology* 36:439-449 (1998), which is hereby incorporated by reference in its entirety), a phospholipase D (Fan et al., "Antisense Suppression of Phospholipase D Alpha Retards Abscisic Acid- and Ethylene-Promoted Senescence of Postharvest *Arabidopsis* Leaves," *Plant Cell* 9:2183-2196 (1997), which is hereby incorporated by reference in its entirety), and an acyl hydrolase (He et al., "A Gene Encoding an Acyl Hydrolase is Involved in Leaf Senescence in *Arabidopsis*," *Plant Cell* 14:805-815 (2002), which is hereby incorporated by reference in its entirety). Similarly, there are only a few genes whose role in leaf senescence has been investigated genetically. For example, the ABA-promoted senescence in detached leaves of PLDa-antisense *Arabidopsis* plants was delayed (Fan et al., "Antisense Suppression of Phospholipase D Alpha Retards Abscisic Acid- and Ethylene-Promoted Senescence of Postharvest *Arabidopsis* Leaves," *Plant Cell* 9:2183-2196 (1997), which is hereby incorporated by reference in its entirety). The *Arabidopsis* F-box gene ORE9 has also been shown to play a role in leaf senescence because the ore9 mutant plants displayed increased leaf longevity (Woo et al., "ORE9, An F-Box Protein That Regulates Leaf Senescence in *Arabidopsis*," *Plant Cell* 13:1779-1790 (2001), which is hereby incorporated by reference in its entirety). It has previously shown that SAG101, a gene encoding an acyl hydrolase, plays a significant role in leaf senescence in *Arabidopsis*; leaf senescence is delayed for 4-5 days in the SAG101 antisense plants (He et al., "A Gene Encoding an Acyl Hydrolase is Involved in Leaf Senescence in *Arabidopsis*," *Plant Cell* 14:805-815 (2002), which is hereby incorporated by reference in its entirety). In the present application, it was shown that leaf senescence in the atnap null mutant line was delayed for up to 10 days (FIGS. 5(a)-(d) and FIGS. 6(a)-(e)). The null phenotype was rescued by the wild type AtNAP, confirming that the lack of AtNAP was responsible for the retardation in leaf senescence in the null mutant plants. The role of AtNAP in controlling leaf senescence was further confirmed by gain-of-function analysis. Young leaves began yellowing as early as 2 days after the initial induction of the AtNAP overexpression, and became completely senescent 4 days after the initial induction (FIGS. 8(a)-(d)), suggesting that AtNAP was sufficient to cause senescence.

The RNA gel blot analysis revealed that AtNAP was expressed in senescing leaf cells (FIGS. 2(a)-(c)). Microarray data currently available at Genevestigator (Zimmermann et al., "GENEVESTIGATOR. *Arabidopsis* Microarray Database and Analysis Toolbox," *Plant Physiol* 136:2621-2632 (2004), which is hereby incorporated by reference in its entirety) also showed that AtNAP is mainly expressed in senescent rosette leaves, cauline leaves, sepals and petals (FIG. 13(a)) although very low levels of the AtNAP expression in young seedlings and other parts of adult plants have been detected (FIG. 13(b)). The AtNAP expression can be strongly induced by inducer of programmed cell death (PCD) in cell suspension, a process similar to leaf senescence. In contrast, other senescence-promoting factors such as ethylene and ABA, osmotic and salt stress only moderately induced the expression of AtNAP while darkness, drought, oxidative stress, jasmonic acid and salicylic acid did not have significant effects on AtNAP expression levels (FIG. 13(b)). In the absence of external stressors, initiation of leaf senescence is dependent on age and developmental stage (Hensel et al., "Developmental and Age-Related Processes That Influence the Longevity and Senescence of Photosynthetic Tissues in Arabidoposis," Plant Cell 5:553-564 (1993); Nooden et al., "Correlative Controls of Senescence and Plant Death in Arabidopsis Thaliana (Brassicaceae)," Journal of Experimental Botany 52:2151-2159 (2001), which are hereby incorporated by reference in their entirety). The data disclosed herein and the microarray data suggest that AtNAP may be primarily up-regulated by age.

Although AtNAP is not readily induced by darkness (Buchanan-Wollaston et al., "Comparative Transcriptome Analysis Reveals Significant Differences in Gene Expression and Signalling Pathways Between Developmental and Dark/Starvation-Induced Senescence in Arabidopsis," The Plant Journal 42:567-585 (2005); Lin et al., "Molecular Events in Senescing Arabidopsis Leaves," Plant Journal 39:612-628 (2004), which are hereby incorporated by reference in their entirety), dark-induced senescence of detached leaves was delayed in the atnap null mutant (FIG. 7(b)-(c)), suggesting that AtNAP may function in dark-induced senescence downstream of the dark-responsive signaling pathway. During natural senescence of leaves on intact plants, AtNAP was only expressed in leaf tissues that are already senescent (FIGS. 2(a)-(c)). These data suggested that AtNAP is likely to play a key role in regulating the common execution process of leaf senescence downstream of various senescence-inducing pathways. Even though expression of AtNAP may not necessarily be responsive to a particular senescence-inducing factor, some of these factors may need AtNAP to trigger the senescence syndrome. As a transcription factor, AtNAP might control the leaf senescence process by transcriptionally activating/repressing genes involved in the execution of senescence.

Plant transcription factors of the same family often have similar functions. At some developmental stages or cellular processes, certain families of transcription factors may play predominant roles (Liu et al., "Transcription Factors and Their Genes in Higher Plants Functional Domains, Evolution and Regulation," Eur J Biochem 262:247-257 (1999); Riechmann et al., "A Genomic Perspective on Plant Transcription Factors," Curr Opin Plant Biol 3:423-434 (2000), which are hereby incorporated by reference in their entirety), such as the MADS box genes in flowering development (Saedler et al., "MADS-Box Genes are Involved in Floral Development and Evolution," Acta Biochim Pol 48:351-358 (2001), which is hereby incorporated by reference in its entirety) and the WRKY genes in defense response (Ulker et al., "WRKY Transcription Factors: From DNA Binding Towards Biological Function," Current Opinion in Plant Biology 7:491-498 (2004), which is hereby incorporated by reference in its entirety). The senescence-associated expression pattern of more than 20 other NAC family members (Buchanan-Wollaston et al., "Comparative Transcriptome Analysis Reveals Significant Differences in Gene Expression and Signalling Pathways Between Developmental and Dark/Starvation-Induced Senescence in Arabidopsis," The Plant Journal 42:567-585 (2005); Guo et al., "Transcriptome of Arabidopsis Leaf Senescence," Plant Cell and Environment 27:521-549 (2004), which are hereby incorporated by reference in their entirety) suggests a general role of the NAC family genes in leaf senescence. The evidence of transcriptional self-regulation (Xie et al., "Arabidopsis NAC1 Transduces Auxin Signal Downstream of TIR1 to Promote Lateral Root Development," Genes Dev 14:3024-3036 (2000), which is hereby incorporated by reference in its entirety) and inter-regulation (Vroemen et al., "The CUP-SHAPED COTYLEDON3 Gene is Required for Boundary and Shoot Meristem Formation in Arabidopsis," Plant Cell 15:1563-1577 (2003), which is hereby incorporated by reference in its entirety) between NAC members as well as homodimerization (Ernst et al., "Structure of the Conserved Domain of ANAC, a Member of the NAC Family of Transcription Factors," EMBO Rep 5:297-303 (2004); Xie et al., "Arabidopsis NAC1 Transduces Auxin Signal Downstream of TIR1 to Promote Lateral Root Development," Genes Dev 14:3024-3036 (2000), which are hereby incorporated by reference in their entirety) and heterodimerization (Hegedus et al., "Molecular Characterization of Brassica Napus NAC Domain Transcriptional Activators Induced in Response to Biotic and Abiotic Stress," Plant Mol Biol 53:383-397 (2003), which is hereby incorporated by reference in its entirety) among NAC proteins suggest possible regulatory networks of leaf senescence involving many NACs.

Sequence homologs of AtNAP in kidney bean (a dicot) and rice (a monocot) also displayed a leaf senescence-specific expression pattern (FIG. 9(c)-(d)). Pv NAP and Os NAP were able to restore the Arabidopsis atnap null mutant to wild type (FIGS. 7(a)-(d)). In addition to rice and kidney bean, sequence homologs exist in a variety of other plant species including soybean (Glycine max), nightshade (Solanum demissum), Medicago truncatula, Populus trichocarpa, wheat (Triticum aestivum), maize (Zea mays), peach (Prunus persica), tomato (Lycopersicon esculentum), potato (Solanum tuberosum), and petunia (Petunia×hybrida) (FIG. 9a). These suggest that NAP may be a universal regulator in plant leaf senescence. It is likely that knocking NAP out in other plant species will cause a significant delay of leaf senescence, which may be a new strategy for manipulating leaf senescence in agriculturally important crops.

AtNAP was previously identified as an immediate target of the floral homeotic genes APETALA3/PISTILLATAL that are essential for petal and stamen formation (Sablowski et al., "A Homolog of NO APICAL MERISTEM is an Immediate Target of the Floral Homeotic Genes APETALA3/PISTILLATA," Cell 92:93-103 (1998), which is hereby incorporated by reference in its entirety). In AtNAP antisense lines, the first 2-4 flowers of the main and lateral inflorescences had short stamens and their anthers often did not dehisce. No leaf senescence phenotype was described (Sablowski et al., "A Homolog of NO APICAL MERISTEM is an Immediate Target of the Floral Homeotic Genes APETALA3/PISTILLATA," Cell 92:93-103 (1998), which is hereby incorporated by reference in its entirety). In the experiments disclosed in the present application, no developmental abnormalities other than the delayed leaf senescence in the two T-DNA mutant lines were observed. This discrepancy may be due to different Arabidopsis ecotypes that were used: Landsberg erecta (Sablowski et al., "A Homolog of NO APICAL MERISTEM is an Immediate Target of the Floral Homeotic Genes APETALA3/PISTILLATA," Cell 92:93-103 (1998), which is hereby incorporated by reference in its entirety) vs. Columbia in the present application. Leaf senescence is a trait with great variations within Arabidopsis ecotypes and the molecular regulation of leaf senescence may differ in different genetic backgrounds (Levey et al., "Natural Variation in the Regulation of Leaf Senescence and Relation to Other Traits in Arabidopsis," Plant Cell and Environment 28:223-231 (2005), which is hereby incorporated by reference in its entirety). This discrepancy may also result from different research approaches employed; T-DNA insertion mutation and antisense approach have shown completely different roles of the phytochrome interacting factor 3 (Kim et al., "Functional Characterization of Phytochrome Interacting Factor 3 in Phytochrome-Mediated Light Signal Transduction," *Plant Cell* 15:2399-2407 (2003); Ni, et al., "PIF3, a Phytochrome-Interacting Factor Necessary for Normal Photoinduced Signal Transduction, is a Novel Basic Helix-Loop-Helix Protein," *Cell* 95:657-667 (1998), which are hereby incorporated by reference in their entirety).

Although the invention has been described in detail, for the purpose of illustration, it is understood that such detail is for that purpose and variations can be made therein by those skilled in the art without departing from the spirit and scope of the invention which is defined by the following claims.

What is claimed:

1. A transgenic plant having a reduced level of endogenous NAP protein capable of causing leaf senescence in a plant, compared to that of a non-transgenic plant, wherein the transgenic plant displays a delayed leaf senescence phenotype relative to a non-transgenic plant, and wherein the plant is transformed with a nucleic acid construct comprising:
   a nucleic acid molecule encoding a NAP protein having the amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13 or a portion thereof, or
   an antisense form of the nucleic acid molecule, wherein the nucleic acid molecule or the antisense form of the nucleic acid molecule is positioned in the nucleic acid construct to result in suppression or interference with endogenous mRNA encoding the endogenous NAP protein.

2. The transgenic plant according to claim 1, wherein the nucleic acid molecule encodes the NAP protein or a portion thereof and is in sense orientation.

3. The transgenic plant according to claim 1, wherein the nucleic acid molecule is an antisense form of the nucleic acid molecule encoding the NAP protein or a portion thereof.

4. The transgenic plant according to claim 1, wherein the plant is transformed with first and second of the nucleic acid constructs, with the first nucleic acid construct encoding the NAP protein or portion thereof in sense orientation and the second nucleic acid construct encoding the NAP protein or portion thereof in antisense form.

5. The transgenic plant according to claim 1, wherein the nucleic acid molecule comprises a first segment encoding the NAP protein or portion thereof, a second segment in an antisense form of the first segment, and a third segment linking the first and second segments.

6. The transgenic plant according to claim 1, wherein the plant is a crop plant.

7. The transgenic plant according to claim 6, wherein the crop plant is selected from the group consisting of alfalfa, rice, wheat, barley, rye, cotton, sunflower, peanut, corn, potato, sweet potato, kidney bean, pea, chicory, lettuce, endive, cabbage, bok choy, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, peach, strawberry, grape, raspberry, pineapple, soybean, *Medicago*, tobacco, tomato, sorghum, and sugarcane.

8. The transgenic plant according to claim 1, wherein the plant is an ornamental plant.

9. The transgenic plant according to claim 8, wherein the ornamental plant is selected from the group consisting of *Arabidopsis thaliana, Saintpaulia, Populus*, petunia, pelargonium, poinsettia, chrysanthemum, carnation, zinnia, turfgrass, lily, and nightshade.

10. A transgenic seed produced from the transgenic plant according to claim 1, wherein the transgenic seed comprises the nucleic acid molecule.

11. A method for delaying leaf senescence in a plant, said method comprising:
   providing a transgenic plant or plant seed transformed with
      a nucleic acid construct comprising a nucleic acid molecule encoding a NAP protein having the amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13 or a portion thereof, wherein said portion is sufficient to result in suppression or interference with endogenous mRNA encoding the endogenous NAP protein; or an antisense form of the nucleic acid molecule; and growing the transgenic plant or the plant grown from the transgenic plant seed under conditions effective to silence endogenous NAP protein expression in the transgenic plant by suppression or interference of endogenous mRNA encoding the endogenous NAP protein and delay leaf senescence in the transgenic plant or the plant grown from the transgenic plant seed.

12. The method according to claim 11, wherein a transgenic plant is provided.

13. The method according to claim 11, wherein a transgenic plant seed is provided.

14. The method according to claim 11, wherein said providing comprises:
providing the nucleic acid construct comprising:
the nucleic acid molecule or the antisense form of the nucleic acid molecule;
a 5' DNA promoter sequence; and
a 3' terminator sequence, wherein the nucleic acid molecule or the antisense form of the nucleic acid molecule, the promoter, and the terminator are operatively coupled to permit expression of the nucleic acid molecule or the antisense form of the nucleic acid molecule;
transforming a plant cell with the nucleic acid construct; and
regenerating a transgenic plant from the transformed plant cell.

15. The method according to claim 14, wherein the nucleic acid molecule encodes the NAP protein or portion thereof and is in sense orientation.

16. The method according to claim 14, wherein the nucleic acid molecule is an antisense form of the nucleic acid molecule encoding the NAP protein or portion thereof.

17. The method according to claim 14, wherein the plant cell is transformed with first and second of the nucleic acid constructs, with the first nucleic acid construct encoding the NAP protein or portion thereof in sense orientation and the second nucleic acid construct encoding the NAP protein or portion thereof in antisense form.

18. The method according to claim 14, wherein the nucleic acid molecule comprises a first segment encoding the NAP protein or portion thereof, a second segment in an antisense form of the first segment, and a third segment linking the first and second segments.

19. The method according to claim 14, wherein the plant cell is from a crop plant.

20. The method according to claim 19, wherein the crop plant is selected from the group consisting of alfalfa, rice, wheat, barley, rye, cotton, sunflower, peanut, corn, potato, sweet potato, kidney bean, pea, chicory, lettuce, endive, cabbage, bok choy, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, peach, strawberry, grape, raspberry, pineapple, soybean, *Medicago*, tobacco, tomato, sorghum, and sugarcane.

21. The method according to claim 14, wherein the plant cell is from an ornamental plant.

22. The method according to claim 21, wherein the ornamental plant is selected from the group consisting of *Arabidopsis thaliara, Saintpaulia, Populus*, petunia, pelargonium, poinsettia, chrysanthemum, carnation, zinnia, turfgrass, lily, and nightshade.

23. The method according to claim 14, wherein said transforming is carried out by a method selected from the group consisting of *Agrobacterium* mediated transformation, vacuum infiltration, biolistic gene transformation, electroporation, microinjection, chemical-mediated transformation, and laser-beam transformation.

24. The method according to claim 11, wherein leaf senescence is delayed in a plant before harvest.

25. The method according to claim 11, wherein leaf senescence is delayed in a plant after harvest.

26. A transgenic plant produced by the method of claim 14, wherein the transgenic plant comprises the nucleic acid molecule.

27. A method for delaying leaf senescence in a plant, said method comprising:
transforming a plant cell with a nucleic acid molecule or an antisense form thereof operably associated with a promoter to obtain a transformed plant cell, wherein the nucleic acid molecule encodes a NAP protein having the amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13 or a portion thereof, and wherein expression of the nucleic acid molecule or the antisense form thereof in the plant cell causes delayed leaf senescence by a form of post-transcriptional gene silencing of the endogenous mRNA encoding the endogenous NAP protein; and
regenerating a plant from the transformed plant cell under conditions effective to delay leaf senescence in the plant.

28. The method according to claim 27, wherein the form of post-transcriptional gene silencing is RNA interference.

29. A transgenic plant seed, wherein the plant seed is transformed with a nucleic acid construct comprising:
a nucleic acid molecule encoding a NAP protein having the amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13 or a portion thereof, or
an antisense form of the nucleic acid molecule, wherein the nucleic acid molecule or the antisense form of the nucleic acid molecule is positioned in the nucleic acid construct to result in suppression or interference with endogenous mRNA encoding an endogenous NAP protein.

* * * * *